United States Patent
Jackson et al.

(10) Patent No.: US 9,980,753 B2
(45) Date of Patent: May 29, 2018

(54) PIVOTAL ANCHOR WITH SNAP-IN-PLACE INSERT HAVING ROTATION BLOCKING EXTENSIONS

(75) Inventors: Roger P Jackson, Prairie Village, KS (US); James L Surber, Kansas City, KS (US)

(73) Assignee: Roger P Jackson, Prairie Village, KS (US)

(*) Notice: Subject to any disclaimer, the term of this patent is extended or adjusted under 35 U.S.C. 154(b) by 0 days. days.

(21) Appl. No.: 13/374,439

(22) Filed: Dec. 29, 2011

(65) Prior Publication Data

US 2012/0143266 A1    Jun. 7, 2012

Related U.S. Application Data

(63) Continuation-in-part of application No. 13/373,289, filed on Nov. 9, 2011, and a continuation-in-part of application No. 12/924,802, filed on Oct. 5, 2010, now Pat. No. 8,556,938, said application No. 13/374,439 is a continuation-in-part of application No. 12/802,849, filed on Jun. 15, 2010.

(60) Provisional application No. 61/460,267, filed on Dec. 29, 2010, provisional application No. 61/463,037, filed on Feb. 11, 2011, provisional application No.
(Continued)

(51) Int. Cl.
*A61B 17/70* (2006.01)

(52) U.S. Cl.
CPC ...... *A61B 17/7032* (2013.01); *A61B 17/7008* (2013.01); *A61B 17/7037* (2013.01); *A61B 17/7076* (2013.01)

(58) Field of Classification Search
CPC .......... A61B 17/7007; A61B 17/7032–17/704; A61B 17/8605–17/862

USPC ............... 606/246, 264–279, 300–321
See application file for complete search history.

(56) References Cited

U.S. PATENT DOCUMENTS

| | | | |
|---|---|---|---|
| 2,243,717 A | 5/1941 | Moreira |
| 2,346,346 A | 4/1944 | Anderson |

(Continued)

FOREIGN PATENT DOCUMENTS

| | | |
|---|---|---|
| DE | 92 02 745.8 | 4/1992 |
| DE | 9202745.8 | 4/1992 |

(Continued)

OTHER PUBLICATIONS

*VLS System Variable Locking Screw* Brochure, Interpore Cross International, 1999.
(Continued)

*Primary Examiner* — Eduardo C Robert
*Assistant Examiner* — Michelle C. Eckman
(74) *Attorney, Agent, or Firm* — Polsinelli PC

(57) ABSTRACT

A polyaxial bone screw assembly includes a threaded shank body having an integral upper portion receivable in an integral receiver, the receiver having an upper channel for receiving a longitudinal connecting member and a lower cavity cooperating with a lower opening. A friction fit compression insert (some with lock and release feature), a planar split retaining ring and a shank upper portion cooperate to provide for pop- or snap-on assembly of the shank with the receiver either prior to or after implantation of the shank into a vertebra. The shank and receiver once assembled cannot be disassembled and the receiver and insert may include aligned tool receiving apertures for lock and release of the polyaxial mechanism.

55 Claims, 29 Drawing Sheets

Related U.S. Application Data

61/456,649, filed on Nov. 10, 2010, provisional application No. 61/460,234, filed on Dec. 29, 2010, provisional application No. 61/278,240, filed on Oct. 5, 2009, provisional application No. 61/336,911, filed on Jan. 28, 2010, provisional application No. 61/343,737, filed on May 3, 2010, provisional application No. 61/395,564, filed on May 14, 2010, provisional application No. 61/395,752, filed on May 17, 2010, provisional application No. 61/396,390, filed on May 26, 2010, provisional application No. 61/398,807, filed on Jul. 1, 2010, provisional application No. 61/400,504, filed on Jul. 29, 2010, provisional application No. 61/402,959, filed on Sep. 8, 2010, provisional application No. 61/403,696, filed on Sep. 20, 2010, provisional application No. 61/403,915, filed on Sep. 23, 2010, provisional application No. 61/268,708, filed on Jun. 15, 2009, provisional application No. 61/270,754, filed on Jul. 13, 2009.

(56) References Cited

U.S. PATENT DOCUMENTS

| | | |
|---|---|---|
| 2,362,999 A | 11/1944 | Elmer |
| 2,531,892 A | 11/1950 | Reese |
| 2,813,450 A | 11/1957 | Dzus |
| 3,013,244 A | 12/1961 | Rudy |
| 3,236,275 A | 2/1966 | Smith |
| 3,604,487 A | 9/1971 | Gilbert |
| 3,640,416 A | 2/1972 | Temple |
| 4,033,139 A | 7/1977 | Frederick |
| 4,041,939 A | 8/1977 | Hall |
| 4,373,754 A | 2/1983 | Bollfrass et al. |
| 4,448,191 A | 5/1984 | Rodnyansky et al. |
| 4,484,570 A | 11/1984 | Sutter et al. |
| 4,600,224 A | 7/1986 | Blose |
| 4,653,486 A | 3/1987 | Coker |
| 4,703,954 A | 11/1987 | Ortloff et al. |
| 4,707,001 A | 11/1987 | Johnson |
| 4,743,260 A | 5/1988 | Burton |
| 4,748,260 A | 5/1988 | Marlett |
| 4,759,672 A | 7/1988 | Nilsen et al. |
| 4,790,297 A | 12/1988 | Luque |
| 4,836,196 A | 6/1989 | Park et al. |
| 4,887,596 A | 12/1989 | Sherman |
| 4,946,458 A | 8/1990 | Harms et al. |
| 4,950,269 A | 8/1990 | Gaines, Jr. |
| 5,005,562 A | 4/1991 | Cotrel |
| 5,019,080 A | 5/1991 | Hemer |
| 5,022,791 A | 6/1991 | Isler |
| 5,034,011 A | 7/1991 | Howland |
| 5,067,955 A | 11/1991 | Cotrel |
| 5,092,635 A | 3/1992 | DeLange et al. |
| 5,102,412 A | 4/1992 | Rogozinski |
| 5,129,388 A | 7/1992 | Vignaud et al. |
| 5,147,363 A | 7/1992 | Harle |
| 5,154,719 A | 10/1992 | Cotrel |
| 5,176,483 A | 1/1993 | Baumann et al. |
| 5,176,678 A | 1/1993 | Tsou |
| 5,176,680 A | 1/1993 | Vignaud et al. |
| 5,180,393 A | 1/1993 | Commarmond |
| 5,207,678 A | 5/1993 | Harms et al. |
| 5,217,497 A | 6/1993 | Mehdian |
| 5,257,993 A | 11/1993 | Asher et al. |
| 5,261,907 A | 11/1993 | Vignaud et al. |
| 5,261,912 A | 11/1993 | Frigg |
| 5,275,601 A | 1/1994 | Gogolewski et al. |
| 5,282,863 A | 2/1994 | Burton |
| 5,306,275 A | 4/1994 | Bryan |
| 5,312,404 A | 5/1994 | Asher et al. |
| 5,321,901 A | 6/1994 | Kelly |
| 5,346,493 A | 9/1994 | Stahurski et al. |
| 5,358,289 A | 10/1994 | Banker et al. |
| 5,360,431 A | 11/1994 | Puno et al. |
| 5,375,823 A | 12/1994 | Navas |
| 5,385,583 A | 1/1995 | Cotrel |
| 5,395,371 A | 3/1995 | Miller et al. |
| 5,415,661 A | 5/1995 | Holmes |
| 5,423,816 A | 6/1995 | Lin |
| 5,427,418 A | 6/1995 | Watts |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,480,401 A | 1/1996 | Navas |
| 5,487,742 A | 1/1996 | Cotrel |
| 5,489,307 A | 2/1996 | Kuslich et al. |
| 5,490,750 A | 2/1996 | Gundy |
| 5,499,892 A | 3/1996 | Reed |
| 5,501,684 A | 3/1996 | Schlapfer |
| 5,505,731 A | 4/1996 | Tornier |
| 5,507,745 A | 4/1996 | Logroscino et al. |
| 5,496,321 A | 5/1996 | Puno |
| 5,540,688 A | 7/1996 | Navas |
| 5,545,165 A | 8/1996 | Biedermann et al. |
| 5,549,607 A | 8/1996 | Olson et al. |
| 5,554,157 A | 9/1996 | Errico et al. |
| 5,562,660 A | 10/1996 | Grob |
| 5,562,663 A | 10/1996 | Wisnewski et al. |
| 5,569,247 A | 10/1996 | Morrison |
| 5,569,251 A | 10/1996 | Baker et al. |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,304 A | 3/1997 | Bailey et al. |
| 5,607,425 A | 3/1997 | Rogozinski |
| 5,607,426 A | 3/1997 | Ralph et al. |
| 5,607,428 A | 3/1997 | Lin |
| 5,611,800 A | 3/1997 | Davis et al. |
| 5,628,740 A | 5/1997 | Mullane |
| 5,630,817 A | 5/1997 | Rokegem |
| 5,641,256 A | 6/1997 | Gundy |
| 5,643,260 A | 7/1997 | Doherty |
| 5,643,261 A | 7/1997 | Schafer et al. |
| 5,647,873 A | 7/1997 | Errico et al. |
| 5,662,652 A | 9/1997 | Schafer et al. |
| 5,662,653 A | 9/1997 | Songer et al. |
| 5,669,909 A | 9/1997 | Zdeblick et al. |
| 5,669,911 A | 9/1997 | Errico et al. |
| 5,672,175 A | 9/1997 | Martin |
| 5,672,176 A | 9/1997 | Biedermann et al. |
| 5,676,703 A | 10/1997 | Gelbard |
| 5,681,319 A | 10/1997 | Biedermann et al. |
| 5,683,390 A | 11/1997 | Metz-Stavenhagen et al. |
| 5,683,392 A | 11/1997 | Richelsoph |
| 5,690,630 A | 11/1997 | Errico et al. |
| 5,697,929 A | 12/1997 | Mellinger |
| 5,711,709 A | 1/1998 | McCoy |
| 5,713,898 A | 2/1998 | Stucker et al. |
| 5,716,356 A | 2/1998 | Biedermann et al. |
| 5,723,013 A | 3/1998 | Jeanson et al. |
| 5,725,527 A | 3/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,735,853 A | 4/1998 | Olerud |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,435 A | 9/1998 | Errico et al. |
| 5,800,547 A | 9/1998 | Schafer et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |

(56) References Cited

U.S. PATENT DOCUMENTS

| | | |
|---|---|---|
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| RE36,221 E | 6/1999 | Breard et al. |
| 5,938,663 A | 8/1999 | Petreto |
| 5,944,465 A | 8/1999 | Janitzki |
| 5,951,553 A | 9/1999 | Betz |
| 5,954,725 A | 9/1999 | Sherman et al. |
| 5,961,517 A | 10/1999 | Biedermann et al. |
| 5,964,760 A | 10/1999 | Richelsoph |
| 6,001,098 A | 12/1999 | Metz-Stavenhagen et al. |
| 6,004,349 A | 12/1999 | Jackson |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,059,786 A | 5/2000 | Jackson |
| 6,063,090 A * | 5/2000 | Schlapfer ............... 606/270 |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,102,913 A | 8/2000 | Jackson |
| 6,110,172 A | 8/2000 | Jackson |
| 6,113,601 A | 9/2000 | Tatar |
| 6,117,137 A | 9/2000 | Halm et al. |
| 6,132,431 A | 10/2000 | Nilsson et al. |
| 6,132,432 A | 10/2000 | Richelsoph |
| 6,132,434 A | 10/2000 | Sherman et al. |
| 6,136,002 A | 10/2000 | Shih et al. |
| 6,143,032 A | 11/2000 | Schafer et al. |
| 6,146,383 A | 11/2000 | Studer et al. |
| 6,183,472 B1 | 2/2001 | Lutz |
| 6,186,718 B1 | 2/2001 | Fogard |
| 6,187,005 B1 | 2/2001 | Brace et al. |
| 6,214,012 B1 | 4/2001 | Karpman et al. |
| RE37,161 E | 5/2001 | Michelson et al. |
| 6,224,596 B1 | 5/2001 | Jackson |
| 6,224,598 B1 | 5/2001 | Jackson |
| 6,235,034 B1 | 5/2001 | Bray |
| 6,241,730 B1 | 6/2001 | Alby |
| 6,241,731 B1 | 6/2001 | Fiz |
| 6,248,105 B1 | 6/2001 | Schlapfer et al. |
| 6,254,146 B1 | 7/2001 | Church |
| 6,254,602 B1 | 7/2001 | Justis |
| 6,267,764 B1 | 7/2001 | Elberg |
| 6,267,765 B1 | 7/2001 | Taylor et al. |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,296,642 B1 | 10/2001 | Morrison et al. |
| 6,296,643 B1 | 10/2001 | Hopf et al. |
| 6,299,613 B1 | 10/2001 | Ogilvie et al. |
| 6,302,888 B1 | 10/2001 | Mellinger et al. |
| 6,309,391 B1 | 10/2001 | Crandall et al. |
| 6,315,564 B1 | 11/2001 | Levisman |
| 6,331,179 B1 | 12/2001 | Freid et al. |
| 6,355,040 B1 | 3/2002 | Richelsoph et al. |
| RE37,665 E | 4/2002 | Ralph et al. |
| 6,368,321 B1 | 4/2002 | Jackson |
| 6,371,957 B1 | 4/2002 | Amrein et al. |
| 6,402,752 B2 | 6/2002 | Schaffler-Wachter et al. |
| 6,402,757 B1 | 6/2002 | Moore et al. |
| 6,440,137 B1 | 8/2002 | Horvath et al. |
| 6,451,021 B1 | 9/2002 | Ralph et al. |
| 6,471,703 B1 | 10/2002 | Ashman |
| 6,471,705 B1 | 10/2002 | Biedermann et al. |
| 6,485,491 B1 | 11/2002 | Farris et al. |
| 6,485,492 B1 | 11/2002 | Halm et al. |
| 6,485,494 B1 | 11/2002 | Haider |
| 6,488,681 B2 | 12/2002 | Martin et al. |
| 6,508,818 B2 | 1/2003 | Steiner et al. |
| 6,520,962 B1 | 2/2003 | Taylor et al. |
| 6,527,804 B1 | 3/2003 | Gauchet et al. |
| 6,530,929 B1 | 3/2003 | Justis et al. |
| 6,533,786 B1 | 3/2003 | Needham et al. |
| 6,540,749 B2 | 4/2003 | Schafer et al. |
| 6,547,790 B2 | 4/2003 | Harkey, III et al. |
| 6,551,320 B2 | 4/2003 | Liebermann |
| 6,551,323 B2 | 4/2003 | Doubler et al. |
| 6,554,831 B1 | 4/2003 | Rivard et al. |
| 6,554,832 B2 | 4/2003 | Shluzas |
| 6,554,834 B1 | 4/2003 | Crozet et al. |
| 6,558,387 B2 | 5/2003 | Errico et al. |
| 6,562,040 B1 | 5/2003 | Wagner |
| 6,565,565 B1 | 5/2003 | Yuan et al. |
| 6,565,567 B1 | 5/2003 | Haider |
| 6,582,436 B2 | 6/2003 | Schlapfer et al. |
| 6,582,466 B1 | 6/2003 | Gauchet |
| 6,585,740 B2 | 7/2003 | Schlapfer et al. |
| 6,595,992 B1 | 7/2003 | Wagner et al. |
| 6,595,993 B2 | 7/2003 | Donno et al. |
| 6,610,063 B2 | 8/2003 | Kumar et al. |
| 6,613,050 B1 | 9/2003 | Wagner et al. |
| 6,623,485 B2 | 9/2003 | Doubler et al. |
| 6,626,907 B2 | 9/2003 | Campbell et al. |
| 6,626,908 B2 | 9/2003 | Cooper et al. |
| 6,635,059 B2 | 10/2003 | Randall et al. |
| 6,648,885 B1 | 11/2003 | Friesem |
| 6,648,887 B2 | 11/2003 | Ashman |
| 6,648,888 B1 | 11/2003 | Shluzas |
| 6,652,526 B1 | 11/2003 | Arafiles |
| 6,652,765 B1 | 11/2003 | Beaty |
| 6,656,179 B1 | 12/2003 | Schaefer et al. |
| 6,656,181 B2 | 12/2003 | Dixon et al. |
| 6,660,004 B2 | 12/2003 | Barker et al. |
| 6,663,632 B1 | 12/2003 | Frigg |
| 6,663,635 B2 | 12/2003 | Frigg et al. |
| 6,673,073 B1 | 1/2004 | Schaefer |
| 6,676,661 B1 | 1/2004 | Benlloch et al. |
| 6,679,833 B2 | 1/2004 | Smith et al. |
| 6,682,529 B2 | 1/2004 | Stahurski |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,695,843 B2 | 2/2004 | Biedermann et al. |
| 6,695,851 B2 | 2/2004 | Zdeblick et al. |
| 6,699,249 B2 | 3/2004 | Schlapfer et al. |
| 6,706,045 B2 | 3/2004 | Lin et al. |
| 6,712,818 B1 | 3/2004 | Michelson |
| 6,716,213 B2 | 4/2004 | Shitoto |
| 6,716,214 B1 | 4/2004 | Jackson |
| 6,716,247 B2 | 4/2004 | Michelson |
| 6,723,100 B2 | 4/2004 | Biedermann et al. |
| 6,730,093 B2 | 5/2004 | Saint Martin |
| 6,730,127 B2 | 5/2004 | Michelson |
| 6,733,502 B2 | 5/2004 | Altarac et al. |
| 6,736,816 B2 | 5/2004 | Ritland |
| 6,736,820 B2 | 5/2004 | Biedermann et al. |
| 6,740,086 B2 | 5/2004 | Richelsoph |
| 6,746,449 B2 | 6/2004 | Jones et al. |
| 6,755,829 B1 | 6/2004 | Bono et al. |
| 6,755,835 B2 | 6/2004 | Schultheiss et al. |
| 6,755,836 B1 | 6/2004 | Lewis |
| 6,761,723 B2 | 7/2004 | Buttermann et al. |
| 6,767,351 B2 | 7/2004 | Orbay et al. |
| 6,770,075 B2 | 8/2004 | Howland |
| 6,780,186 B2 | 8/2004 | Errico et al. |
| 6,783,527 B2 | 8/2004 | Drewry et al. |
| 6,790,209 B2 | 9/2004 | Beale et al. |
| 6,802,844 B2 | 10/2004 | Ferree |
| 6,827,719 B2 | 12/2004 | Ralph et al. |
| 6,830,571 B2 | 12/2004 | Lenke et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 6,843,791 B2 | 1/2005 | Serhan |
| 6,858,031 B2 | 2/2005 | Morrison et al. |
| 6,869,432 B2 | 3/2005 | Schlapfer et al. |

(56) References Cited

U.S. PATENT DOCUMENTS

| | | | |
|---|---|---|---|
| 6,869,433 B2 | 3/2005 | Glascott |
| 6,872,208 B1 | 3/2005 | McBride et al. |
| 6,896,676 B2 | 5/2005 | Zubok et al. |
| 6,896,677 B1 | 5/2005 | Lin |
| 6,932,817 B2 | 8/2005 | Baynham et al. |
| 6,932,820 B2 | 8/2005 | Osman |
| 6,945,972 B2 | 9/2005 | Frigg et al. |
| 6,953,462 B2 | 10/2005 | Liebermann |
| 6,955,677 B2 | 10/2005 | Dahners |
| 6,958,065 B2 | 10/2005 | Ueyama et al. |
| 6,964,664 B2 | 11/2005 | Freid et al. |
| 6,964,665 B2 | 11/2005 | Thomas et al. |
| 6,964,667 B2 | 11/2005 | Shaolian et al. |
| 6,966,910 B2 | 11/2005 | Ritland |
| 6,974,460 B2 | 12/2005 | Carbone et al. |
| 6,979,334 B2 | 12/2005 | Dalton |
| 6,981,973 B2 | 1/2006 | McKinley |
| 6,986,771 B2 | 1/2006 | Paul et al. |
| 6,989,011 B2 | 1/2006 | Paul et al. |
| 6,991,632 B2 | 1/2006 | Ritland |
| 7,001,389 B1 | 2/2006 | Navarro et al. |
| RE39,035 E | 3/2006 | Finn et al. |
| 7,008,424 B2 | 3/2006 | Teitelbaum |
| 7,018,378 B2 | 3/2006 | Biedermann et al. |
| 7,018,379 B2 | 3/2006 | Drewry et al. |
| 7,022,122 B2 | 4/2006 | Amrein et al. |
| 7,029,475 B2 | 4/2006 | Panjabi |
| RE39,089 E | 5/2006 | Ralph et al. |
| 7,066,062 B2 | 6/2006 | Flesher |
| 7,066,937 B2 | 6/2006 | Shluzas |
| 7,081,116 B1 | 7/2006 | Carly |
| 7,083,621 B2 | 8/2006 | Shaolian et al. |
| 7,087,057 B2 | 8/2006 | Konieczynski et al. |
| 7,090,674 B2 | 8/2006 | Doubler et al. |
| 7,121,755 B2 | 10/2006 | Schlapfer et al. |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,137,985 B2 | 11/2006 | Jahng |
| 7,141,051 B2 | 11/2006 | Janowski et al. |
| 7,144,396 B2 | 12/2006 | Shluzas |
| 7,163,538 B2 | 1/2007 | Altarac et al. |
| 7,163,539 B2 | 1/2007 | Abdelgany et al. |
| 7,166,108 B2 | 1/2007 | Mazda et al. |
| 7,186,255 B2 | 3/2007 | Baynham et al. |
| 7,207,992 B2 | 4/2007 | Ritland |
| 7,211,086 B2 | 5/2007 | Biedermann et al. |
| 7,211,087 B2 | 5/2007 | Young |
| 7,214,227 B2 | 5/2007 | Colleran et al. |
| 7,223,268 B2 | 5/2007 | Biedermann |
| 7,229,441 B2 | 6/2007 | Trieu et al. |
| 7,264,621 B2 | 9/2007 | Coates et al. |
| 7,270,665 B2 | 9/2007 | Morrison et al. |
| 7,291,151 B2 | 11/2007 | Alvarez |
| 7,291,153 B2 | 11/2007 | Glascott |
| 7,294,127 B2 | 11/2007 | Hawkins et al. |
| 7,294,128 B2 | 11/2007 | Alleyne et al. |
| 7,294,129 B2 | 11/2007 | Hawkins et al. |
| 7,306,603 B2 | 12/2007 | Boehm, Jr. et al. |
| 7,306,604 B2 | 12/2007 | Carli |
| 7,306,606 B2 | 12/2007 | Sasing |
| 7,314,467 B2 | 1/2008 | Howland |
| 7,316,684 B1 | 1/2008 | Baccelli et al. |
| 7,322,979 B2 | 1/2008 | Crandall et al. |
| 7,322,981 B2 | 1/2008 | Jackson |
| 7,329,258 B2 | 2/2008 | Studer |
| 7,335,201 B2 | 2/2008 | Doubler et al. |
| 7,335,202 B2 | 2/2008 | Matthis et al. |
| 7,338,490 B2 | 3/2008 | Ogilvie et al. |
| 7,338,491 B2 | 3/2008 | Baker et al. |
| 7,445,627 B2 | 11/2008 | Hawkes et al. |
| 7,476,228 B2 | 1/2009 | Abdou |
| 7,479,156 B2 | 1/2009 | Lourdel et al. |
| 7,491,218 B2 | 2/2009 | Landry et al. |
| 7,491,221 B2 | 2/2009 | David |
| 7,503,918 B2 | 3/2009 | Baccelli et al. |
| 7,503,924 B2 | 3/2009 | Lee et al. |
| 7,524,323 B2 | 4/2009 | Malandain |
| 7,527,640 B2 | 5/2009 | Ziolo et al. |
| 7,530,992 B2 * | 5/2009 | Biedermann et al. ........ 606/272 |
| 7,559,943 B2 | 7/2009 | Mujwid |
| 7,563,264 B2 | 7/2009 | Landry et al. |
| 7,563,275 B2 | 7/2009 | Falahee et al. |
| 7,569,061 B2 | 8/2009 | Colleran |
| 7,572,279 B2 | 8/2009 | Jackson |
| 7,572,280 B2 | 8/2009 | Dickinson et al. |
| 7,575,587 B2 | 8/2009 | Rezach et al. |
| 7,588,575 B2 | 9/2009 | Colleran et al. |
| 7,588,588 B2 | 9/2009 | Spitler et al. |
| 7,588,593 B2 | 9/2009 | Aferzon |
| 7,591,839 B2 | 9/2009 | Biedermann et al. |
| 7,601,166 B2 | 10/2009 | Biedermann et al. |
| 7,604,655 B2 | 10/2009 | Warnick |
| 7,604,656 B2 | 10/2009 | Shluzas |
| 7,611,518 B2 | 11/2009 | Walder et al. |
| 7,615,068 B2 | 11/2009 | Timm et al. |
| 7,621,941 B2 | 11/2009 | Schlapfer et al. |
| 7,625,394 B2 | 12/2009 | Molz, IV et al. |
| 7,625,396 B2 | 12/2009 | Jackson |
| 7,641,674 B2 | 1/2010 | Young |
| 7,645,294 B2 | 1/2010 | Kalfasetd |
| 7,648,522 B2 | 1/2010 | David |
| 7,648,552 B2 | 1/2010 | David |
| 7,658,739 B2 | 2/2010 | Shluzas |
| 7,662,172 B2 | 2/2010 | Warnick |
| 7,674,277 B2 | 3/2010 | Burd et al. |
| 7,678,136 B2 | 3/2010 | Doubler et al. |
| 7,678,139 B2 | 3/2010 | Garamszegi et al. |
| 7,682,377 B2 | 3/2010 | Konieczynski et al. |
| 7,686,833 B1 | 3/2010 | Muhanna et al. |
| 7,686,834 B2 | 3/2010 | Saint Martin |
| 7,686,835 B2 | 3/2010 | Warnick |
| 7,691,129 B2 | 4/2010 | Felix |
| 7,691,131 B2 | 4/2010 | Graf |
| 7,691,132 B2 | 4/2010 | Landry et al. |
| 7,695,497 B2 | 4/2010 | Cordaro et al. |
| 7,695,498 B2 | 4/2010 | Ritland |
| 7,699,872 B2 | 4/2010 | Farris et al. |
| 7,699,875 B2 | 4/2010 | Timm |
| 7,699,876 B2 | 4/2010 | Barry et al. |
| 7,704,271 B2 | 4/2010 | Abdou |
| 7,713,288 B2 | 5/2010 | Timm et al. |
| 7,717,941 B2 | 5/2010 | Petit |
| 7,717,942 B2 | 5/2010 | Schumacher |
| 7,717,943 B2 | 5/2010 | Kirschman |
| 7,722,646 B2 | 5/2010 | Ralph et al. |
| 7,722,649 B2 | 5/2010 | Biedermann et al. |
| 7,722,651 B2 | 5/2010 | Kwak et al. |
| 7,722,652 B2 | 5/2010 | Justis et al. |
| 7,722,654 B2 | 5/2010 | Taylor et al. |
| 7,727,261 B2 | 6/2010 | Barker et al. |
| 7,731,736 B2 | 6/2010 | Guenther et al. |
| 7,731,749 B2 | 6/2010 | Biedermann et al. |
| 7,749,258 B2 | 7/2010 | Biedermann et al. |
| 7,758,618 B2 | 7/2010 | Walder et al. |
| 7,763,057 B2 | 7/2010 | Abdelgany et al. |
| 7,766,943 B1 | 8/2010 | Fallin et al. |
| 7,766,944 B2 | 8/2010 | Metz-Stavenhagen |
| 7,766,945 B2 | 8/2010 | Nilsson et al. |
| 7,766,946 B2 | 8/2010 | Bailly |
| 7,776,067 B2 | 8/2010 | Jackson |
| 7,780,706 B2 | 8/2010 | Marino et al. |
| 7,785,351 B2 | 8/2010 | Gordon et al. |
| 7,785,354 B2 | 8/2010 | Biedermann et al. |
| 7,789,900 B2 | 9/2010 | Levy et al. |
| 7,794,477 B2 | 9/2010 | Melkent et al. |
| 7,794,480 B2 | 9/2010 | Gordon et al. |
| 7,806,913 B2 | 10/2010 | Fanger et al. |
| 7,811,288 B2 | 10/2010 | Jones et al. |
| 7,811,310 B2 | 10/2010 | Baker et al. |
| 7,819,902 B2 | 10/2010 | Abdelgany et al. |
| 7,833,251 B1 * | 11/2010 | Ahlgren et al. ............ 606/279 |
| 7,857,834 B2 * | 12/2010 | Boschert ................... 606/269 |
| 7,875,065 B2 | 1/2011 | Jackson |

(56) References Cited

U.S. PATENT DOCUMENTS

| | | |
|---|---|---|
| 7,922,748 B2 | 4/2011 | Hoffman |
| 7,947,065 B2 | 5/2011 | Hammill et al. |
| RE42,545 E | 7/2011 | Ralph et al. |
| 7,972,364 B2 | 7/2011 | Biedermann et al. |
| 7,985,242 B2 | 7/2011 | Forton et al. |
| 7,985,248 B2 | 7/2011 | Walder et al. |
| RE42,626 E | 8/2011 | Taylor et al. |
| 7,988,694 B2 | 8/2011 | Barrus et al. |
| 7,988,711 B2 | 8/2011 | Erricksone et al. |
| 8,002,806 B2 | 8/2011 | Justis |
| 8,012,183 B2 | 9/2011 | Alain |
| 8,012,186 B2 | 9/2011 | Pham et al. |
| 8,012,188 B2 | 9/2011 | Melent et al. |
| 8,016,862 B2 | 9/2011 | Felix et al. |
| 8,016,866 B2 | 9/2011 | Warnick |
| 8,021,097 B2 | 9/2011 | Farris et al. |
| 8,021,397 B2 | 9/2011 | Farris et al. |
| 8,022,806 B2 | 9/2011 | Nishimura et al. |
| 8,025,681 B2 | 9/2011 | Colleran et al. |
| 8,029,539 B2 | 10/2011 | Kirschman |
| 8,034,084 B2 | 10/2011 | Landry et al. |
| 8,034,089 B2 | 10/2011 | Matthis et al. |
| 8,043,340 B1 | 10/2011 | Law |
| 8,048,112 B2 | 11/2011 | Suziki et al. |
| 8,048,126 B2 | 11/2011 | Altarac et al. |
| 8,066,744 B2 | 11/2011 | Justis et al. |
| 8,133,262 B2 | 3/2012 | Whipple |
| 8,137,386 B2 | 3/2012 | Jackson |
| 8,206,422 B2 | 6/2012 | Hestad et al. |
| 8,277,485 B2 | 10/2012 | Krishna et al. |
| 8,361,129 B2 | 1/2013 | Chao |
| 8,430,914 B2 | 4/2013 | Spratt et al. |
| 8,506,609 B2 | 8/2013 | Biedermann et al. |
| 8,591,558 B2 | 11/2013 | Matthis et al. |
| 9,168,069 B2 | 10/2015 | Jackson |
| 9,393,047 B2 | 9/2016 | Jackson et al. |
| 9,480,517 B2 | 11/2016 | Jackson et al. |
| 9,504,496 B2 | 11/2016 | Jackson et al. |
| 2001/0001119 A1 | 5/2001 | Lombardo |
| 2001/0010000 A1 | 7/2001 | Gertzbein |
| 2001/0016193 A1 | 8/2001 | Ritland |
| 2001/0029375 A1 | 10/2001 | Betz |
| 2001/0037111 A1 | 11/2001 | Dixon et al. |
| 2002/0007184 A1 | 1/2002 | Ogilvie et al. |
| 2002/0013586 A1 | 1/2002 | Justis et al. |
| 2002/0026193 A1 | 2/2002 | Barker et al. |
| 2002/0035366 A1 | 3/2002 | Walder et al. |
| 2002/0045898 A1 | 4/2002 | Freid et al. |
| 2002/0058942 A1 | 5/2002 | Biedermann et al. |
| 2002/0072751 A1 | 6/2002 | Jackson |
| 2002/0082602 A1 | 6/2002 | Biedermann et al. |
| 2002/0111626 A1 | 8/2002 | Ralph et al. |
| 2002/0133159 A1 | 9/2002 | Jackson |
| 2002/0203511 | 9/2002 | Wilson-MacDonald et al. |
| 2002/0143341 A1 | 10/2002 | Biedermann et al. |
| 2002/0173789 A1 | 11/2002 | Howland |
| 2002/0193795 A1 | 12/2002 | Gertzbein et al. |
| 2003/0023240 A1 | 1/2003 | Amrein et al. |
| 2003/0023243 A1 | 1/2003 | Biedermann et al. |
| 2003/0073996 A1 | 4/2003 | Doubler et al. |
| 2003/0083657 A1 | 5/2003 | Drewry et al. |
| 2003/0093078 A1 | 5/2003 | Ritland |
| 2003/0100896 A1 | 5/2003 | Biedermann et al. |
| 2003/0105460 A1 | 6/2003 | Crandall et al. |
| 2003/0109880 A1 | 6/2003 | Shirado et al. |
| 2003/0114852 A1 | 6/2003 | Biedermann et al. |
| 2003/0125741 A1 | 7/2003 | Biedermann et al. |
| 2003/0149432 A1 | 8/2003 | Frigg et al. |
| 2003/0153911 A1 | 8/2003 | Shluzas |
| 2003/0163133 A1 | 8/2003 | Altarac et al. |
| 2003/0171749 A1 | 9/2003 | Le Couedic et al. |
| 2003/0176862 A1 | 9/2003 | Taylor et al. |
| 2003/0191470 A1 | 10/2003 | Ritland |
| 2003/0199873 A1 | 10/2003 | Richelsoph |
| 2003/0208204 A1 | 11/2003 | Bailey et al. |
| 2003/0216735 A1 | 11/2003 | Altarac et al. |
| 2003/0220642 A1 | 11/2003 | Freudiger |
| 2003/0220643 A1 | 11/2003 | Ferree |
| 2004/0002708 A1 | 1/2004 | Ritland |
| 2004/0006342 A1 | 1/2004 | Altarac et al. |
| 2004/0049189 A1 | 3/2004 | Le Couedic et al. |
| 2004/0049190 A1 | 3/2004 | Biedermann et al. |
| 2004/0073215 A1 | 4/2004 | Carli |
| 2004/0078082 A1 | 4/2004 | Lange |
| 2004/0087949 A1 | 5/2004 | Bono et al. |
| 2004/0087952 A1 | 5/2004 | Borgstrom et al. |
| 2004/0092934 A1 | 5/2004 | Howland |
| 2004/0097933 A1 | 5/2004 | Lourdel et al. |
| 2004/0116929 A1 | 6/2004 | Barker et al. |
| 2004/0138662 A1 | 7/2004 | Landry et al. |
| 2004/0143265 A1 | 7/2004 | Landry et al. |
| 2004/0147928 A1 | 7/2004 | Landry et al. |
| 2004/0147929 A1 | 7/2004 | Biedermann et al. |
| 2004/0158247 A1 | 8/2004 | Sitiso et al. |
| 2004/0172022 A1 | 9/2004 | Landry et al. |
| 2004/0176766 A1 | 9/2004 | Shluzas |
| 2004/0186473 A1 | 9/2004 | Cournoyer et al. |
| 2004/0210216 A1 | 10/2004 | Farris et al. |
| 2004/0225289 A1 | 11/2004 | Biedermann et al. |
| 2004/0236327 A1 | 11/2004 | Paul et al. |
| 2004/0236328 A1 | 11/2004 | Paul et al. |
| 2004/0236329 A1 | 11/2004 | Panjabi |
| 2004/0236330 A1 | 11/2004 | Purcell et al. |
| 2004/0249380 A1 | 12/2004 | Glascott |
| 2004/0260283 A1 | 12/2004 | Wu et al. |
| 2004/0267264 A1* | 12/2004 | Konieczynski et al. ........ 606/73 |
| 2005/0027296 A1 | 2/2005 | Thramann et al. |
| 2005/0033298 A1 | 2/2005 | Hawkes et al. |
| 2005/0038432 A1 | 2/2005 | Shaolian et al. |
| 2005/0049708 A1 | 3/2005 | Atkinson et al. |
| 2005/0055026 A1 | 3/2005 | Biedermann et al. |
| 2005/0065515 A1 | 3/2005 | Jahng |
| 2005/0065516 A1 | 3/2005 | Jahng |
| 2005/0070899 A1 | 3/2005 | Doubler et al. |
| 2005/0080415 A1 | 4/2005 | Keyer et al. |
| 2005/0085815 A1 | 4/2005 | Harms et al. |
| 2005/0085816 A1 | 4/2005 | Michelson |
| 2005/0096652 A1 | 5/2005 | Burton |
| 2005/0096654 A1 | 5/2005 | Lin |
| 2005/0107788 A1 | 5/2005 | Beaurain et al. |
| 2005/0113927 A1 | 5/2005 | Malek |
| 2005/0124991 A1 | 6/2005 | Jahng |
| 2005/0131404 A1 | 6/2005 | Mazda et al. |
| 2005/0131407 A1 | 6/2005 | Sicvol et al. |
| 2005/0131413 A1 | 6/2005 | O'Driscoll et al. |
| 2005/0137597 A1 | 6/2005 | Butler et al. |
| 2005/0143737 A1 | 6/2005 | Pafford et al. |
| 2005/0143823 A1 | 6/2005 | Boyd et al. |
| 2005/0144389 A1 | 6/2005 | Trika et al. |
| 2005/0149020 A1 | 7/2005 | Jahng |
| 2005/0149023 A1 | 7/2005 | Ritland |
| 2005/0154389 A1 | 7/2005 | Selover et al. |
| 2005/0154390 A1 | 7/2005 | Biedermann et al. |
| 2005/0154391 A1 | 7/2005 | Doherty et al. |
| 2005/0159750 A1 | 7/2005 | Doherty |
| 2005/0165396 A1 | 7/2005 | Fortin et al. |
| 2005/0165400 A1 | 7/2005 | Fernandez |
| 2005/0171540 A1 | 8/2005 | Lim et al. |
| 2005/0171543 A1 | 8/2005 | Timm et al. |
| 2005/0177157 A1 | 8/2005 | Jahng |
| 2005/0182401 A1 | 8/2005 | Timm et al. |
| 2005/0187548 A1 | 8/2005 | Butler et al. |
| 2005/0187555 A1 | 8/2005 | Biedermann et al. |
| 2005/0192580 A1 | 9/2005 | Dalton |
| 2005/0203511 A1 | 9/2005 | Wilson-MacDonald et al. |
| 2005/0203513 A1 | 9/2005 | Jahng et al. |
| 2005/0203514 A1 | 9/2005 | Jahng et al. |
| 2005/0203516 A1 | 9/2005 | Harms et al. |
| 2005/0203517 A1 | 9/2005 | Jahng et al. |
| 2005/0203518 A1 | 9/2005 | Biedermann et al. |
| 2005/0203519 A1 | 9/2005 | Harms et al. |
| 2005/0216001 A1 | 9/2005 | David |
| 2005/0216003 A1 | 9/2005 | Biedermann et al. |
| 2005/0228501 A1 | 10/2005 | Miller et al. |

(56) References Cited

U.S. PATENT DOCUMENTS

| | | |
|---|---|---|
| 2005/0234450 A1 | 10/2005 | Barker |
| 2005/0234451 A1 | 10/2005 | Markworth |
| 2005/0234452 A1 | 10/2005 | Malandain |
| 2005/0234453 A1 | 10/2005 | Shaolian et al. |
| 2005/0234454 A1 | 10/2005 | Chin |
| 2005/0234456 A1 | 10/2005 | Malandain |
| 2005/0240181 A1 | 10/2005 | Boomer et al. |
| 2005/0240183 A1 | 10/2005 | Vaughan |
| 2005/0245930 A1 | 11/2005 | Timm et al. |
| 2005/0251137 A1 | 11/2005 | Ball |
| 2005/0251140 A1 | 11/2005 | Shaolian et al. |
| 2005/0251141 A1 | 11/2005 | Frigg et al. |
| 2005/0260058 A1 | 11/2005 | Casagne, III |
| 2005/0261685 A1 | 11/2005 | Fortin et al. |
| 2005/0261687 A1 | 11/2005 | Garamszegi et al. |
| 2005/0267470 A1 | 12/2005 | McBride |
| 2005/0267471 A1 | 12/2005 | Biedermann et al. |
| 2005/0267474 A1 | 12/2005 | Dalton |
| 2005/0273099 A1 | 12/2005 | Baccelli et al. |
| 2005/0273101 A1 | 12/2005 | Schumacher |
| 2005/0277919 A1 | 12/2005 | Slivka et al. |
| 2005/0277922 A1 | 12/2005 | Trieu et al. |
| 2005/0277923 A1 | 12/2005 | Sweeney |
| 2005/0277925 A1 | 12/2005 | Mujwid |
| 2005/0277927 A1 | 12/2005 | Guenther et al. |
| 2005/0277928 A1 | 12/2005 | Boschert |
| 2005/0283152 A1 | 12/2005 | Lindemann et al. |
| 2005/0283157 A1 | 12/2005 | Coates et al. |
| 2005/0283238 A1 | 12/2005 | Reiley |
| 2005/0283244 A1 | 12/2005 | Gordon et al. |
| 2005/0288669 A1 | 12/2005 | Abdou |
| 2005/0288670 A1 | 12/2005 | Panjabi et al. |
| 2005/0288671 A1 | 12/2005 | Yuan et al. |
| 2005/0288672 A1 | 12/2005 | Ferree |
| 2005/0288673 A1 | 12/2005 | Catbagan et al. |
| 2006/0004357 A1 | 1/2006 | Lee et al. |
| 2006/0004359 A1 | 1/2006 | Kramer et al. |
| 2006/0004360 A1 | 1/2006 | Kramer et al. |
| 2006/0004363 A1 | 1/2006 | Brockmeyer et al. |
| 2006/0009767 A1 | 1/2006 | Kiester |
| 2006/0009768 A1 | 1/2006 | Ritland |
| 2006/0009769 A1 | 1/2006 | Lieberman |
| 2006/0009770 A1 | 1/2006 | Speirs et al. |
| 2006/0009846 A1 | 1/2006 | Trieu et al. |
| 2006/0015099 A1 | 1/2006 | Cannon et al. |
| 2006/0015104 A1 | 1/2006 | Dalton |
| 2006/0025767 A1 | 2/2006 | Khalili |
| 2006/0025768 A1 | 2/2006 | Iott et al. |
| 2006/0025770 A1 | 2/2006 | Schlapfer et al. |
| 2006/0036240 A1 | 2/2006 | Colleran et al. |
| 2006/0036242 A1 | 2/2006 | Nilsson et al. |
| 2006/0036244 A1 | 2/2006 | Spitler et al. |
| 2006/0036246 A1 | 2/2006 | Carl et al. |
| 2006/0036252 A1 | 2/2006 | Baynham et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0041259 A1 | 2/2006 | Paul et al. |
| 2006/0052780 A1 | 3/2006 | Errico et al. |
| 2006/0052783 A1 | 3/2006 | Dant et al. |
| 2006/0052784 A1 | 3/2006 | Dant et al. |
| 2006/0052786 A1 | 3/2006 | Dant et al. |
| 2006/0058788 A1 | 3/2006 | Hammer et al. |
| 2006/0058790 A1 | 3/2006 | Carl et al. |
| 2006/0064090 A1 | 3/2006 | Park |
| 2006/0064091 A1 | 3/2006 | Ludwig et al. |
| 2006/0064092 A1 | 3/2006 | Howland |
| 2006/0069390 A1 | 3/2006 | Frigg |
| 2006/0074419 A1 | 4/2006 | Taylor et al. |
| 2006/0079894 A1 | 4/2006 | Colleran et al. |
| 2006/0079895 A1 | 4/2006 | McLeer |
| 2006/0079896 A1 | 4/2006 | Kwak |
| 2006/0079898 A1 | 4/2006 | Ainsworth |
| 2006/0079899 A1 | 4/2006 | Ritland |
| 2006/0084981 A1 | 4/2006 | Shluzas |
| 2006/0084982 A1 | 4/2006 | Kim |
| 2006/0084983 A1 | 4/2006 | Kim |
| 2006/0084984 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0084989 A1 | 4/2006 | Dickinson et al. |
| 2006/0084991 A1 | 4/2006 | Borgstrom |
| 2006/0084993 A1 | 4/2006 | Landry et al. |
| 2006/0084995 A1 | 4/2006 | Biedermann et al. |
| 2006/0085069 A1 | 4/2006 | Kim |
| 2006/0089643 A1 | 4/2006 | Mujwid |
| 2006/0089644 A1 | 4/2006 | Felix |
| 2006/0095037 A1 | 5/2006 | Jones et al. |
| 2006/0106380 A1 | 5/2006 | Colleran et al. |
| 2006/0106381 A1 | 5/2006 | Ferree |
| 2006/0106383 A1 | 5/2006 | Biedermann et al. |
| 2006/0116677 A1 | 6/2006 | Burd et al. |
| 2006/0122599 A1 | 6/2006 | Drewry |
| 2006/0129147 A1 | 6/2006 | Biedermann et al. |
| 2006/0129149 A1 | 6/2006 | Iott et al. |
| 2006/0129239 A1 | 6/2006 | Kwak |
| 2006/0142758 A1 | 6/2006 | Petit |
| 2006/0142760 A1 | 6/2006 | McDonnell |
| 2006/0142761 A1 | 6/2006 | Landry et al. |
| 2006/0149228 A1 | 7/2006 | Schlapfer |
| 2006/0149229 A1 | 7/2006 | Kwak |
| 2006/0149232 A1 | 7/2006 | Sasing |
| 2006/0149241 A1 | 7/2006 | Richelsoph et al. |
| 2006/0149244 A1 | 7/2006 | Amrein et al. |
| 2006/0155277 A1 | 7/2006 | Metz-Stavenhagen |
| 2006/0155278 A1 | 7/2006 | Warnick |
| 2006/0161152 A1 | 7/2006 | Ensign et al. |
| 2006/0166535 A1 | 7/2006 | Brumfield et al. |
| 2006/0167455 A1 | 7/2006 | Clement et al. |
| 2006/0173454 A1 | 8/2006 | Spitler et al. |
| 2006/0173456 A1 | 8/2006 | Hawkes et al. |
| 2006/0184171 A1 | 8/2006 | Biedermann |
| 2006/0184180 A1 | 8/2006 | Augostino |
| 2006/0189983 A1 | 8/2006 | Fallin |
| 2006/0189984 A1 | 8/2006 | Fallin |
| 2006/0189985 A1 | 8/2006 | Lewis |
| 2006/0195090 A1 | 8/2006 | Suddaby |
| 2006/0195093 A1 | 8/2006 | Jahng |
| 2006/0195198 A1 | 8/2006 | James |
| 2006/0200123 A1 | 9/2006 | Mueller |
| 2006/0200130 A1 | 9/2006 | Hawkins |
| 2006/0200131 A1 | 9/2006 | Chao et al. |
| 2006/0200149 A1 | 9/2006 | Hoy et al. |
| 2006/0212033 A1 | 9/2006 | Rothman |
| 2006/0212034 A1 | 9/2006 | Triplett et al. |
| 2006/0217716 A1 | 9/2006 | Baker et al. |
| 2006/0229608 A1 | 10/2006 | Foster |
| 2006/0229609 A1 | 10/2006 | Wang |
| 2006/0229612 A1 | 10/2006 | Rothman |
| 2006/0229613 A1 | 10/2006 | Timm |
| 2006/0229614 A1 | 10/2006 | Foley et al. |
| 2006/0229615 A1 | 10/2006 | Abdou |
| 2006/0235389 A1 | 10/2006 | Albert et al. |
| 2006/0235392 A1 | 10/2006 | Hammer et al. |
| 2006/0235393 A1 | 10/2006 | Bono et al. |
| 2006/0241593 A1 | 10/2006 | Sherman et al. |
| 2006/0241595 A1 | 10/2006 | Molz, IV et al. |
| 2006/0241599 A1 | 10/2006 | Konieczynski et al. |
| 2006/0241600 A1 | 10/2006 | Ensign et al. |
| 2006/0241769 A1 | 10/2006 | Gordon |
| 2006/0241771 A1 | 10/2006 | Gordon |
| 2006/0247624 A1 | 11/2006 | Banouskou et al. |
| 2006/0247631 A1 | 11/2006 | Ahn et al. |
| 2006/0247632 A1 | 11/2006 | Winslow |
| 2006/0247633 A1 | 11/2006 | Winslow |
| 2006/0247635 A1 | 11/2006 | Gordon |
| 2006/0247636 A1 | 11/2006 | Yuan et al. |
| 2006/0247637 A1 | 11/2006 | Colleran |
| 2006/0247779 A1 | 11/2006 | Gordon |
| 2006/0264933 A1 | 11/2006 | Baker et al. |
| 2006/0264935 A1 | 11/2006 | White |
| 2006/0264936 A1 | 11/2006 | Partin et al. |

(56) References Cited

U.S. PATENT DOCUMENTS

| | | |
|---|---|---|
| 2006/0264937 A1 | 11/2006 | White |
| 2006/0264940 A1 | 11/2006 | Hartmannt |
| 2006/0276787 A1 | 12/2006 | Zubok et al. |
| 2006/0276789 A1 | 12/2006 | Jackson |
| 2006/0276791 A1 | 12/2006 | Shluzas |
| 2006/0276792 A1 | 12/2006 | Ensign et al. |
| 2006/0282074 A1 | 12/2006 | Renaud et al. |
| 2006/0282075 A1 | 12/2006 | Labrom |
| 2006/0282076 A1 | 12/2006 | Labrom |
| 2006/0282077 A1 | 12/2006 | Labrom |
| 2006/0282078 A1 | 12/2006 | Labrom |
| 2006/0282079 A1 | 12/2006 | Labrom |
| 2006/0282080 A1 | 12/2006 | Albert |
| 2006/0293657 A1 | 12/2006 | Hartmann |
| 2006/0293659 A1 | 12/2006 | Alvarez |
| 2006/0293663 A1 | 12/2006 | Walkenhorst |
| 2006/0293665 A1 | 12/2006 | Shluzas |
| 2006/0293666 A1 | 12/2006 | Matthis et al. |
| 2007/0005062 A1 | 1/2007 | Lange |
| 2007/0005063 A1 | 1/2007 | Bruneau |
| 2007/0005137 A1 | 1/2007 | Kwak |
| 2007/0016188 A1 | 1/2007 | Boehm, Jr. et al. |
| 2007/0016190 A1 | 1/2007 | Martinez |
| 2007/0016198 A1 | 1/2007 | Boehm, Jr. et al. |
| 2007/0021750 A1 | 1/2007 | Shluzas et al. |
| 2007/0043355 A1 | 2/2007 | Bette et al. |
| 2007/0043356 A1 | 2/2007 | Timm |
| 2007/0043357 A1 | 2/2007 | Kirschman |
| 2007/0043358 A1 | 2/2007 | Molz, IV et al. |
| 2007/0043359 A1 | 2/2007 | Altarac et al. |
| 2007/0043364 A1 | 2/2007 | Cawley et al. |
| 2007/0049933 A1 | 3/2007 | Ahn et al. |
| 2007/0049936 A1 | 3/2007 | Colleran |
| 2007/0055235 A1 | 3/2007 | Janowski et al. |
| 2007/0055236 A1 | 3/2007 | Hudgins |
| 2007/0055238 A1 | 3/2007 | Biedermann et al. |
| 2007/0055239 A1 | 3/2007 | Sweeney et al. |
| 2007/0055240 A1 | 3/2007 | Matthis et al. |
| 2007/0055241 A1 | 3/2007 | Matthis et al. |
| 2007/0055242 A1 | 3/2007 | Bailly |
| 2007/0055244 A1 | 3/2007 | Jackson |
| 2007/0055247 A1 | 3/2007 | Jahng |
| 2007/0073289 A1 | 3/2007 | Kwak |
| 2007/0073291 A1 | 3/2007 | Cordaro et al. |
| 2007/0073293 A1 | 3/2007 | Martz |
| 2007/0078460 A1 | 4/2007 | Frigg et al. |
| 2007/0078461 A1 | 4/2007 | Shluzas |
| 2007/0083199 A1 | 4/2007 | Baccelli |
| 2007/0088357 A1 | 4/2007 | Johnson et al. |
| 2007/0088359 A1 | 4/2007 | Woods et al. |
| 2007/0090238 A1 | 4/2007 | Justis |
| 2007/0093813 A1 | 4/2007 | Callahan, II et al. |
| 2007/0093814 A1 | 4/2007 | Callahan, II et al. |
| 2007/0093815 A1 | 4/2007 | Callahan, II et al. |
| 2007/0093817 A1 | 4/2007 | Barrus et al. |
| 2007/0093818 A1 | 4/2007 | Biedermann et al. |
| 2007/0093819 A1 | 4/2007 | Albert |
| 2007/0093826 A1 | 4/2007 | Hawkes et al. |
| 2007/0093827 A1 | 4/2007 | Warnick |
| 2007/0093831 A1 | 4/2007 | Abdelgany et al. |
| 2007/0100341 A1 | 5/2007 | Reglos et al. |
| 2007/0118117 A1 | 5/2007 | Altarac et al. |
| 2007/0118118 A1 | 5/2007 | Kwak et al. |
| 2007/0118119 A1 | 5/2007 | Hestad |
| 2007/0118122 A1 | 5/2007 | Butler et al. |
| 2007/0118123 A1* | 5/2007 | Strausbaugh ...... A61B 17/7032 606/272 |
| 2007/0118124 A1 | 5/2007 | Biedermann et al. |
| 2007/0123862 A1* | 5/2007 | Warnick ............. A61B 17/7032 606/261 |
| 2007/0123864 A1 | 5/2007 | Walder et al. |
| 2007/0123865 A1 | 5/2007 | Schlapfer et al. |
| 2007/0123866 A1 | 5/2007 | Gerbec et al. |
| 2007/0123867 A1 | 5/2007 | Kirschman |
| 2007/0123870 A1 | 5/2007 | Jeon et al. |
| 2007/0123871 A1 | 5/2007 | Jahng |
| 2007/0124249 A1 | 5/2007 | Aerrabotu et al. |
| 2007/0129729 A1 | 6/2007 | Petit et al. |
| 2007/0135815 A1 | 6/2007 | Gerbec et al. |
| 2007/0161986 A1 | 7/2007 | Levy |
| 2007/0161991 A1 | 7/2007 | Altarac et al. |
| 2007/0161994 A1 | 7/2007 | Lowrey et al. |
| 2007/0161995 A1 | 7/2007 | Trautwein et al. |
| 2007/0161996 A1 | 7/2007 | Biedermann et al. |
| 2007/0161997 A1 | 7/2007 | Thramann et al. |
| 2007/0161999 A1 | 7/2007 | Biedermann et al. |
| 2007/0167948 A1 | 7/2007 | Abdou |
| 2007/0167949 A1 | 7/2007 | Altarac et al. |
| 2007/0173818 A1 | 7/2007 | Hestad et al. |
| 2007/0173819 A1 | 7/2007 | Sandlin |
| 2007/0173820 A1 | 7/2007 | Trieu |
| 2007/0173822 A1 | 7/2007 | Bruneau et al. |
| 2007/0173828 A1 | 7/2007 | Firkins et al. |
| 2007/0173832 A1 | 7/2007 | Tebbe et al. |
| 2007/0191839 A1 | 8/2007 | Justis et al. |
| 2007/0191841 A1 | 8/2007 | Justis et al. |
| 2007/0191846 A1 | 8/2007 | Bruneau et al. |
| 2007/0198014 A1 | 8/2007 | Graf et al. |
| 2007/0208344 A1 | 9/2007 | Young |
| 2007/0213720 A1 | 9/2007 | Gordon et al. |
| 2007/0225707 A1 | 9/2007 | Wisnewski et al. |
| 2007/0225708 A1 | 9/2007 | Biedermann et al. |
| 2007/0225710 A1 | 9/2007 | Jahng et al. |
| 2007/0225711 A1 | 9/2007 | Ensign |
| 2007/0233064 A1 | 10/2007 | Holt |
| 2007/0233073 A1 | 10/2007 | Wisnewski et al. |
| 2007/0233075 A1 | 10/2007 | Dawson |
| 2007/0233078 A1 | 10/2007 | Justis et al. |
| 2007/0233080 A1 | 10/2007 | Na et al. |
| 2007/0233085 A1 | 10/2007 | Biedermann et al. |
| 2007/0233086 A1 | 10/2007 | Harms et al. |
| 2007/0233087 A1 | 10/2007 | Schlapfer |
| 2007/0233092 A1 | 10/2007 | Falahee |
| 2007/0233094 A1 | 10/2007 | Colleran et al. |
| 2007/0233095 A1 | 10/2007 | Schlaepfer |
| 2007/0250061 A1 | 10/2007 | Chin et al. |
| 2007/0260243 A1 | 11/2007 | Kagami |
| 2007/0270806 A1 | 11/2007 | Foley et al. |
| 2007/0270807 A1 | 11/2007 | Armstrong et al. |
| 2007/0270810 A1 | 11/2007 | Sanders |
| 2007/0270813 A1 | 11/2007 | Garamszegi |
| 2007/0270814 A1 | 11/2007 | Lim et al. |
| 2007/0270815 A1 | 11/2007 | Johnson et al. |
| 2007/0270830 A1 | 11/2007 | Morrison |
| 2007/0270831 A1* | 11/2007 | Dewey et al. .................. 606/61 |
| 2007/0270832 A1 | 11/2007 | Moore |
| 2007/0270835 A1 | 11/2007 | Wisnewski |
| 2007/0270837 A1 | 11/2007 | Eckhardt et al. |
| 2007/0270838 A1 | 11/2007 | Bruneau et al. |
| 2007/0270839 A1 | 11/2007 | Jeon et al. |
| 2007/0270843 A1 | 11/2007 | Matthis et al. |
| 2007/0276380 A1 | 11/2007 | Jahng et al. |
| 2007/0288004 A1 | 12/2007 | Alvarez |
| 2007/0288008 A1 | 12/2007 | Park |
| 2007/0288009 A1 | 12/2007 | Brown et al. |
| 2007/0288011 A1 | 12/2007 | Logan |
| 2007/0288012 A1 | 12/2007 | Colleran et al. |
| 2008/0009862 A1 | 1/2008 | Hoffman |
| 2008/0009864 A1 | 1/2008 | Forton et al. |
| 2008/0015578 A1 | 1/2008 | Erickson et al. |
| 2008/0015579 A1 | 1/2008 | Whipple |
| 2008/0015580 A1 | 1/2008 | Chao |
| 2008/0015584 A1 | 1/2008 | Richelsoph |
| 2008/0015586 A1 | 1/2008 | Krishna et al. |
| 2008/0015597 A1 | 1/2008 | Whipple |
| 2008/0021454 A1 | 1/2008 | Chao et al. |
| 2008/0021455 A1 | 1/2008 | Chao et al. |
| 2008/0021458 A1 | 1/2008 | Lim |
| 2008/0021459 A1 | 1/2008 | Lim |
| 2008/0021462 A1 | 1/2008 | Trieu |
| 2008/0021464 A1 | 1/2008 | Morin et al. |
| 2008/0021465 A1 | 1/2008 | Shadduck et al. |
| 2008/0021466 A1 | 1/2008 | Shadduck et al. |
| 2008/0021473 A1 | 1/2008 | Butler et al. |

(56) References Cited

U.S. PATENT DOCUMENTS

| | | |
|---|---|---|
| 2008/0027432 A1 | 1/2008 | Strauss et al. |
| 2008/0033435 A1 | 2/2008 | Studer et al. |
| 2008/0039838 A1 | 2/2008 | Landry et al. |
| 2008/0039843 A1 | 2/2008 | Abdou |
| 2008/0045951 A1 | 2/2008 | Fanger et al. |
| 2008/0045955 A1 | 2/2008 | Berrevoets et al. |
| 2008/0045957 A1 | 2/2008 | Landry et al. |
| 2008/0051780 A1 | 2/2008 | Vaidya et al. |
| 2008/0051787 A1 | 2/2008 | Remington et al. |
| 2008/0058811 A1 | 3/2008 | Alleyne et al. |
| 2008/0058812 A1 | 3/2008 | Zehnder |
| 2008/0065071 A1 | 3/2008 | Park |
| 2008/0065073 A1 | 3/2008 | Perriello et al. |
| 2008/0065075 A1 | 3/2008 | Dant |
| 2008/0065077 A1 | 3/2008 | Ferree |
| 2008/0065079 A1 | 3/2008 | Bruneau et al. |
| 2008/0071273 A1 | 3/2008 | Hawkes et al. |
| 2008/0071274 A1 | 3/2008 | Ensign |
| 2008/0071277 A1 | 3/2008 | Warnick |
| 2008/0077139 A1 | 3/2008 | Landry et al. |
| 2008/0086131 A1 | 4/2008 | Daly et al. |
| 2008/0086132 A1 | 4/2008 | Biedermann et al. |
| 2008/0097441 A1 | 4/2008 | Hayes et al. |
| 2008/0097457 A1 | 4/2008 | Warnick |
| 2008/0108992 A1 | 5/2008 | Barry et al. |
| 2008/0114362 A1* | 5/2008 | Justis et al. ............... 606/72 |
| 2008/0119857 A1 | 5/2008 | Potash |
| 2008/0119858 A1 | 5/2008 | Potash |
| 2008/0132957 A1 | 6/2008 | Matthis et al. |
| 2008/0140075 A1 | 6/2008 | Ensign et al. |
| 2008/0140135 A1* | 6/2008 | Konieczynski et al. ...... 606/309 |
| 2008/0140136 A1 | 6/2008 | Jackson |
| 2008/0147129 A1 | 6/2008 | Biedermann et al. |
| 2008/0154315 A1 | 6/2008 | Jackson |
| 2008/0161859 A1 | 7/2008 | Nilsson |
| 2008/0161863 A1 | 7/2008 | Arnold et al. |
| 2008/0177321 A1 | 7/2008 | Drewry et al. |
| 2008/0177322 A1 | 7/2008 | Davis et al. |
| 2008/0177332 A1 | 7/2008 | Reiley et al. |
| 2008/0183215 A1 | 7/2008 | Altarac et al. |
| 2008/0183223 A1 | 7/2008 | Jeon et al. |
| 2008/0195159 A1 | 8/2008 | Kloss et al. |
| 2008/0200956 A1 | 8/2008 | Beckwith et al. |
| 2008/0215095 A1 | 9/2008 | Biedermann et al. |
| 2008/0215100 A1 | 9/2008 | Matthis et al. |
| 2008/0228229 A1 | 9/2008 | Walder et al. |
| 2008/0234734 A1 | 9/2008 | Walder et al. |
| 2008/0234756 A1 | 9/2008 | Sutcliffe et al. |
| 2008/0234759 A1 | 9/2008 | Marino |
| 2008/0234761 A1 | 9/2008 | Jackson |
| 2008/0249570 A1 | 10/2008 | Carson et al. |
| 2008/0249576 A1 | 10/2008 | Hawkes et al. |
| 2008/0262548 A1 | 10/2008 | Lange et al. |
| 2008/0262556 A1 | 10/2008 | Jacofsky et al. |
| 2008/0269742 A1 | 10/2008 | Levy et al. |
| 2008/0269809 A1 | 10/2008 | Garamszegi |
| 2008/0287994 A1 | 11/2008 | Perez-Cruet et al. |
| 2008/0288002 A1 | 11/2008 | Crall et al. |
| 2008/0306528 A1 | 12/2008 | Winslow et al. |
| 2008/0306533 A1 | 12/2008 | Winslow et al. |
| 2008/0306539 A1 | 12/2008 | Cain et al. |
| 2008/0312655 A1 | 12/2008 | Kirschman et al. |
| 2008/0312692 A1 | 12/2008 | Brennan et al. |
| 2008/0312696 A1 | 12/2008 | Butters et al. |
| 2008/0312701 A1 | 12/2008 | Butters et al. |
| 2008/0319490 A1 | 12/2008 | Jackson |
| 2009/0005787 A1 | 1/2009 | Crall et al. |
| 2009/0005813 A1 | 1/2009 | Crall et al. |
| 2009/0005814 A1 | 1/2009 | Miller et al. |
| 2009/0012567 A1 | 1/2009 | Biedermann et al. |
| 2009/0018591 A1 | 1/2009 | Hawkes et al. |
| 2009/0024169 A1 | 1/2009 | Triplett et al. |
| 2009/0030457 A1 | 1/2009 | Janowski et al. |
| 2009/0036929 A1 | 2/2009 | Reglos et al. |
| 2009/0036932 A1 | 2/2009 | Rouyer et al. |
| 2009/0036934 A1 | 2/2009 | Biedermann et al. |
| 2009/0062860 A1 | 3/2009 | Fraiser et al. |
| 2009/0062865 A1 | 3/2009 | Schumacher |
| 2009/0062867 A1* | 3/2009 | Schumacher ............... 606/308 |
| 2009/0062914 A1 | 3/2009 | Marino |
| 2009/0069849 A1 | 3/2009 | Oh et al. |
| 2009/0069852 A1 | 3/2009 | Farris et al. |
| 2009/0069853 A1 | 3/2009 | Schumacher |
| 2009/0076550 A1 | 3/2009 | Bernhardt, Jr. et al. |
| 2009/0076552 A1 | 3/2009 | Tornier |
| 2009/0082809 A1 | 3/2009 | Nguyen et al. |
| 2009/0082812 A1 | 3/2009 | Lewis |
| 2009/0082815 A1 | 3/2009 | Zylber et al. |
| 2009/0082819 A1 | 3/2009 | Blain et al. |
| 2009/0088799 A1 | 4/2009 | Yeh |
| 2009/0088807 A1 | 4/2009 | Castaneda et al. |
| 2009/0093843 A1 | 4/2009 | Lemoine et al. |
| 2009/0105769 A1 | 4/2009 | Rock et al. |
| 2009/0105770 A1 | 4/2009 | Berrevoets et al. |
| 2009/0105771 A1 | 4/2009 | Lei et al. |
| 2009/0118772 A1 | 5/2009 | Diederich et al. |
| 2009/0131983 A1 | 5/2009 | Biedermann et al. |
| 2009/0138044 A1 | 5/2009 | Bergeron et al. |
| 2009/0138052 A1 | 5/2009 | Biedermann et al. |
| 2009/0143827 A1 | 6/2009 | Levy et al. |
| 2009/0143829 A1 | 6/2009 | Shluzas |
| 2009/0149887 A1 | 6/2009 | Schlaepfer et al. |
| 2009/0163955 A1 | 6/2009 | Moumene et al. |
| 2009/0163956 A1 | 6/2009 | Biedermann et al. |
| 2009/0163961 A1 | 6/2009 | Kirschman |
| 2009/0163963 A1 | 6/2009 | Berrevoets |
| 2009/0182380 A1 | 7/2009 | Abdelgany |
| 2009/0192548 A1 | 7/2009 | Jeon et al. |
| 2009/0192551 A1 | 7/2009 | Cianfrani et al. |
| 2009/0198280 A1 | 8/2009 | Spratt et al. |
| 2009/0198289 A1 | 8/2009 | Manderson |
| 2009/0198291 A1 | 8/2009 | Kevin et al. |
| 2009/0204155 A1 | 8/2009 | Aschmann |
| 2009/0216280 A1 | 8/2009 | Hutchinson |
| 2009/0248030 A1 | 10/2009 | Butler et al. |
| 2009/0248075 A1 | 10/2009 | Ogilvie et al. |
| 2009/0248088 A1 | 10/2009 | Biedermann |
| 2009/0254125 A1 | 10/2009 | Predick |
| 2009/0259254 A1 | 10/2009 | Pisharodi |
| 2009/0264896 A1 | 10/2009 | Biedermann et al. |
| 2009/0264933 A1 | 10/2009 | Carls et al. |
| 2009/0270916 A1 | 10/2009 | Ramsay et al. |
| 2009/0270917 A1 | 10/2009 | Boehm |
| 2009/0281571 A1 | 11/2009 | Weaver et al. |
| 2009/0281572 A1 | 11/2009 | White |
| 2009/0281573 A1 | 11/2009 | Biedermann et al. |
| 2009/0287253 A1 | 11/2009 | Felix et al. |
| 2009/0299415 A1 | 12/2009 | Pimenta |
| 2009/0306719 A1 | 12/2009 | Meyer, III et al. |
| 2009/0306720 A1 | 12/2009 | Doubler et al. |
| 2009/0312804 A1 | 12/2009 | Gamache et al. |
| 2009/0326582 A1 | 12/2009 | Songer et al. |
| 2009/0326587 A1 | 12/2009 | Matthis et al. |
| 2010/0004692 A1 | 1/2010 | Biedermann et al. |
| 2010/0010540 A1 | 1/2010 | Park |
| 2010/0016898 A1 | 1/2010 | Shluzas |
| 2010/0023061 A1 | 1/2010 | Randol et al. |
| 2010/0030224 A1 | 2/2010 | Winslow et al. |
| 2010/0030271 A1 | 2/2010 | Winslow et al. |
| 2010/0030283 A1 | 2/2010 | King et al. |
| 2010/0036417 A1 | 2/2010 | James et al. |
| 2010/0036420 A1 | 2/2010 | Kalfas et al. |
| 2010/0036422 A1 | 2/2010 | Flynn et al. |
| 2010/0036432 A1 | 2/2010 | Ely |
| 2010/0042155 A1 | 2/2010 | Biedermann et al. |
| 2010/0049254 A1 | 2/2010 | Biedermann et al. |
| 2010/0057125 A1 | 3/2010 | Viker |
| 2010/0057126 A1 | 3/2010 | Hestad |
| 2010/0063545 A1 | 3/2010 | Richelsoph |
| 2010/0063546 A1 | 3/2010 | Miller et al. |
| 2010/0063550 A1 | 3/2010 | Felix et al. |
| 2010/0063551 A1 | 3/2010 | Richelsoph |
| 2010/0063553 A1 | 3/2010 | Warnick |
| 2010/0069963 A1 | 3/2010 | Eckman |

(56) References Cited

U.S. PATENT DOCUMENTS

| | | |
|---|---|---|
| 2010/0069969 A1 | 3/2010 | Ampuero et al. |
| 2010/0087861 A1 | 4/2010 | Lechmann et al. |
| 2010/0087865 A1 | 4/2010 | Biedermann et al. |
| 2010/0094343 A1 | 4/2010 | Pham et al. |
| 2010/0094345 A1 | 4/2010 | Saidha et al. |
| 2010/0094348 A1 | 4/2010 | Biedermann et al. |
| 2010/0094349 A1* | 4/2010 | Hammer et al. .............. 606/264 |
| 2010/0094352 A1 | 4/2010 | Ioft et al. |
| 2010/0094353 A1 | 4/2010 | Shim et al. |
| 2010/0100136 A1 | 4/2010 | Kaufman et al. |
| 2010/0100137 A1 | 4/2010 | Justis et al. |
| 2010/0106189 A1 | 4/2010 | Miller |
| 2010/0114170 A1* | 5/2010 | Barrus ............... A61B 17/7037 606/264 |
| 2010/0114171 A1 | 5/2010 | Boachie-Adjei et al. |
| 2010/0114180 A1 | 5/2010 | Rock et al. |
| 2010/0125302 A1 | 5/2010 | Hammill, Sr. et al. |
| 2010/0131017 A1 | 5/2010 | Farris et al. |
| 2010/0131018 A1 | 5/2010 | Konieczynski et al. |
| 2010/0137918 A1 | 6/2010 | Wilcox et al. |
| 2010/0137920 A1 | 6/2010 | Hammill, Sr. et al. |
| 2010/0145390 A1 | 6/2010 | McCarthy et al. |
| 2010/0152776 A1 | 6/2010 | Keyer et al. |
| 2010/0152785 A1 | 6/2010 | Forton et al. |
| 2010/0152787 A1* | 6/2010 | Walsh et al. .................. 606/308 |
| 2010/0152788 A1 | 6/2010 | Warnick |
| 2010/0160965 A1 | 6/2010 | Viker |
| 2010/0160974 A1 | 6/2010 | Viker |
| 2010/0160980 A1 | 6/2010 | Walsh et al. |
| 2010/0168796 A1 | 7/2010 | Eliasen et al. |
| 2010/0168800 A1 | 7/2010 | Biedermann et al. |
| 2010/0168801 A1 | 7/2010 | Biedermann et al. |
| 2010/0174322 A1 | 7/2010 | Abdelgany et al. |
| 2010/0179603 A1 | 7/2010 | Warnick |
| 2010/0185247 A1 | 7/2010 | Richelsoph |
| 2010/0191290 A1 | 7/2010 | Felix |
| 2010/0198269 A1 | 8/2010 | Taylor et al. |
| 2010/0198270 A1 | 8/2010 | Barker et al. |
| 2010/0198272 A1 | 8/2010 | Keyer et al. |
| 2010/0204735 A1 | 8/2010 | Gephart et al. |
| 2010/0222822 A1 | 9/2010 | Farris et al. |
| 2010/0228293 A1 | 9/2010 | Courtney et al. |
| 2010/0234891 A1 | 9/2010 | Freeman et al. |
| 2010/0234902 A1* | 9/2010 | Biedermann et al. ........ 606/305 |
| 2010/0241170 A1 | 9/2010 | Cammisa et al. |
| 2010/0249846 A1 | 9/2010 | Simonson |
| 2010/0249856 A1 | 9/2010 | Iott et al. |
| 2010/0256681 A1 | 10/2010 | Hammer et al. |
| 2010/0256682 A1 | 10/2010 | Fallin et al. |
| 2010/0256686 A1 | 10/2010 | Fisher |
| 2010/0262195 A1 | 10/2010 | Jackson |
| 2010/0262196 A1 | 10/2010 | Barrus et al. |
| 2010/0274288 A1 | 10/2010 | Prevost et al. |
| 2010/0305621 A1 | 12/2010 | Wang et al. |
| 2011/0166606 A1 | 7/2011 | Stihl et al. |
| 2011/0172715 A1 | 7/2011 | Pond, Jr. et al. |
| 2011/0178558 A1 | 7/2011 | Barry |
| 2011/0184471 A1 | 7/2011 | Foley et al. |
| 2011/0190822 A1 | 8/2011 | Spitler et al. |
| 2011/0190823 A1 | 8/2011 | Bergeron et al. |
| 2011/0190826 A1 | 8/2011 | Ogilvie et al. |
| 2011/0196427 A1 | 8/2011 | Trautwein et al. |
| 2011/0202095 A1 | 8/2011 | Semler et al. |
| 2011/0208251 A1 | 8/2011 | Hammill, Sr. et al. |
| 2011/0230917 A1 | 9/2011 | Carson et al. |
| 2011/0251644 A1 | 10/2011 | Hestad et al. |
| 2011/0257687 A1 | 10/2011 | Trieu et al. |
| 2011/0257689 A1 | 10/2011 | Fiechter et al. |
| 2011/0257690 A1 | 10/2011 | Rezach |
| 2012/0010661 A1 | 1/2012 | Farris et al. |
| 2012/0046700 A1 | 2/2012 | Jackson et al. |
| 2012/0059426 A1 | 3/2012 | Jackson et al. |
| 2013/0023941 A1 | 1/2013 | Jackson et al. |
| 2014/0128927 A1 | 5/2014 | Jackson |
| 2016/0051290 A1 | 2/2016 | Jackson et al. |
| 2016/0354121 A1 | 12/2016 | Jackson |
| 2017/0042586 A1 | 2/2017 | Jackson et al. |
| 2017/0296234 A1 | 10/2017 | Jackson et al. |
| 2017/0333086 A1 | 11/2017 | Jackson |

FOREIGN PATENT DOCUMENTS

| | | |
|---|---|---|
| DE | G9202745.8 | 4/1992 |
| DE | 4239716 | 8/1994 |
| DE | 4425392 | 11/1995 |
| DE | 195 07 141 | 9/1996 |
| DE | 19507141 | 9/1996 |
| DE | 19509331 | 9/1996 |
| DE | 29806563 | 7/1998 |
| DE | 29810798 | 12/1999 |
| DE | 19951145 | 5/2001 |
| DE | 10236691 | 2/2004 |
| EP | 0667127 | 8/1995 |
| EP | 0669109 | 8/1995 |
| EP | 0677277 | 10/1995 |
| EP | 0885598 | 12/1998 |
| EP | 1 121 902 | 8/2001 |
| EP | 1121902 | 8/2001 |
| EP | 1190678 | 3/2002 |
| EP | 1210914 | 6/2002 |
| EP | 1570795 | 2/2005 |
| EP | 1570795 | 9/2005 |
| EP | 1579816 | 9/2005 |
| EP | 1634537 | 3/2006 |
| EP | 1925263 | 5/2008 |
| EP | 2380513 | 10/2011 |
| FR | 2717370 | 9/1995 |
| FR | 2718946 | 10/1995 |
| FR | 2729291 | 7/1996 |
| FR | 2796545 | 1/2001 |
| FR | 2799949 | 4/2001 |
| FR | 2814936 | 4/2002 |
| FR | 2856578 | 6/2003 |
| FR | 2865373 | 1/2004 |
| FR | 2865375 | 1/2004 |
| FR | 2865377 | 1/2004 |
| FR | 2857850 | 4/2004 |
| FR | 2865378 | 10/2004 |
| FR | 2925288 | 6/2009 |
| GB | 2365345 | 2/2002 |
| GB | 2382304 | 5/2003 |
| JP | 10277070 | 10/1998 |
| JP | 2000325358 | 3/2000 |
| WO | WO 92/03100 | 3/1992 |
| WO | WO 94/10927 | 5/1994 |
| WO | WO 94/26191 | 11/1994 |
| WO | 9501132 | 1/1995 |
| WO | WO 95/01132 | 1/1995 |
| WO | WO95/01132 | 1/1995 |
| WO | WO9641582 | 12/1996 |
| WO | WO 01/10317 | 2/2001 |
| WO | WO01/10317 | 2/2001 |
| WO | WO2001/45576 | 6/2001 |
| WO | WO02/054966 | 7/2002 |
| WO | WO2002/102259 | 12/2002 |
| WO | WO2003/026523 | 4/2003 |
| WO | WO03/068088 | 8/2003 |
| WO | 2004041100 | 5/2004 |
| WO | WO2004/041100 | 5/2004 |
| WO | WO2004/075778 | 9/2004 |
| WO | 2004089245 | 10/2004 |
| WO | WO2004/089245 | 10/2004 |
| WO | 2004107997 | 12/2004 |
| WO | WO2004/107997 | 12/2004 |
| WO | 2005000136 | 1/2005 |
| WO | 2005000137 | 1/2005 |
| WO | WO2005/000136 | 1/2005 |
| WO | WO2005/000137 | 1/2005 |
| WO | 2005020829 | 3/2005 |
| WO | WO2005/020829 | 3/2005 |
| WO | WO2005/065374 | 7/2005 |
| WO | WO2005/065375 | 7/2005 |
| WO | 2005072632 | 8/2005 |
| WO | WO2005/072632 | 8/2005 |

(56) References Cited

FOREIGN PATENT DOCUMENTS

| | | |
|---|---|---|
| WO | 2005082262 | 9/2005 |
| WO | WO2005/082262 | 9/2005 |
| WO | WO2005/099400 | 10/2005 |
| WO | WO2005/104969 | 11/2005 |
| WO | 2006005198 | 1/2006 |
| WO | WO2006/005198 | 1/2006 |
| WO | WO2006/012088 | 2/2006 |
| WO | WO2006/017616 | 2/2006 |
| WO | WO2006/028537 | 3/2006 |
| WO | WO2006/045094 | 4/2006 |
| WO | WO2006/119241 | 11/2006 |
| WO | 2007118045 | 10/2007 |
| WO | WO2007/118045 | 10/2007 |
| WO | 2007124222 | 11/2007 |
| WO | 2007130840 | 11/2007 |
| WO | 2007130941 | 11/2007 |
| WO | WO2007/124222 | 11/2007 |
| WO | WO2007/0130835 | 11/2007 |
| WO | WO2007/130840 | 11/2007 |
| WO | WO2007/130941 | 11/2007 |
| WO | WO2008/088731 | 7/2008 |
| WO | 2009015100 | 1/2009 |
| WO | WO2009/015100 | 1/2009 |
| WO | WO2010/017631 | 2/2010 |

OTHER PUBLICATIONS

*Silhouette Spinal Fixation System* Brochure, Sulzer Medica Spine-Tech, no publish date.
*The Strength of Innovation* Advertisement, Blackstone Medical Inc., no publish date.
*Spine*, Lipcott, Williams & Wilkins, Inc. vol. 24, No. 15, p. 1495
Brochure of Tyco/Healthcare/Surgical Dynamics on Spiral Radius 90D, Publication Date: Sep. 2001, pp. 1-8.
Claris Instrumentation Brochure, G Med, pub. 1997.
EBI Omega 21 Brochure, EBI Spine Systems, pub. 1999.
SDRS Surgical Dynamics Rod System Brochure, Surgical Dynamics, pub. 1998-99.
The Rod Plate System Brochure, Stryker Howmedica Osteonics, pub. Oct. 1999.
Versalok Low Back Fixation System Brochure, Wright Medical Technology, Inc., pub. 1997.
Brochure of DePuySpine on Surgical Technique, Published 2004, pp. 1-36.

\* cited by examiner

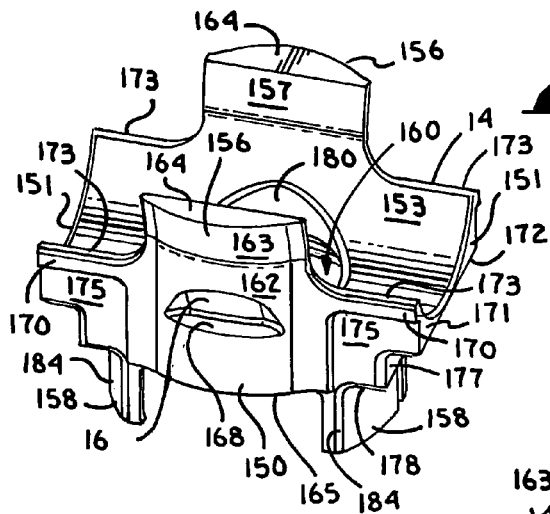
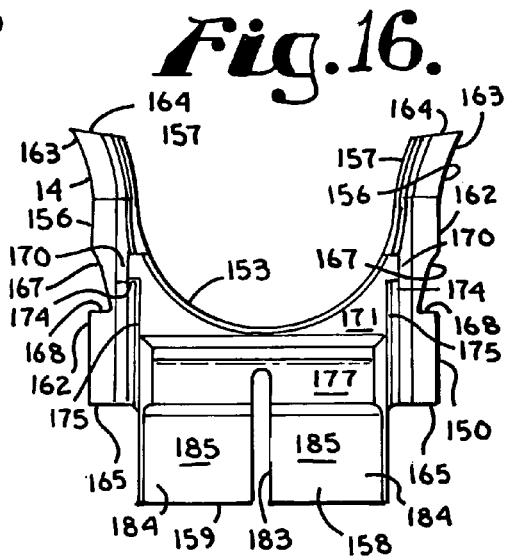
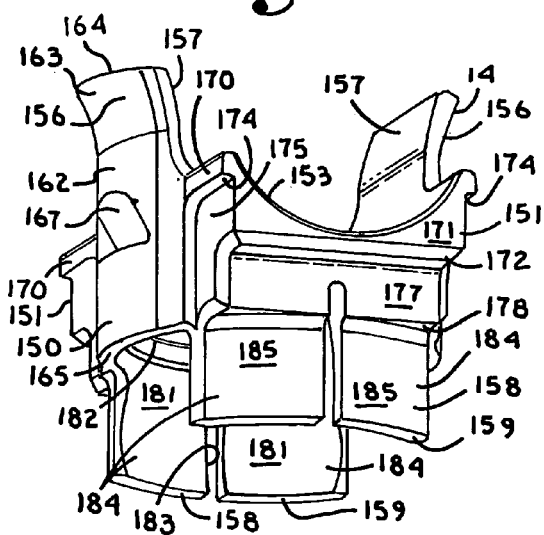

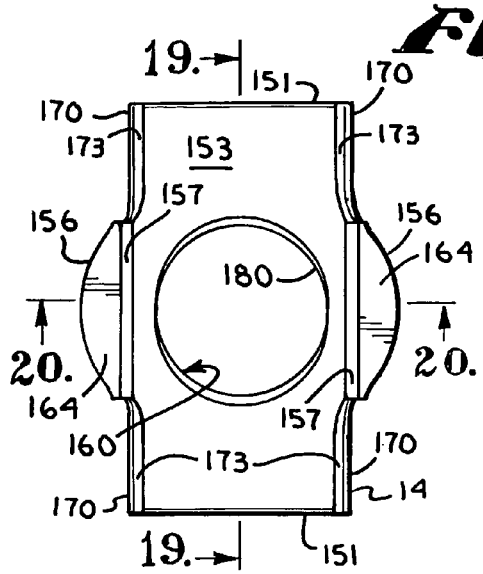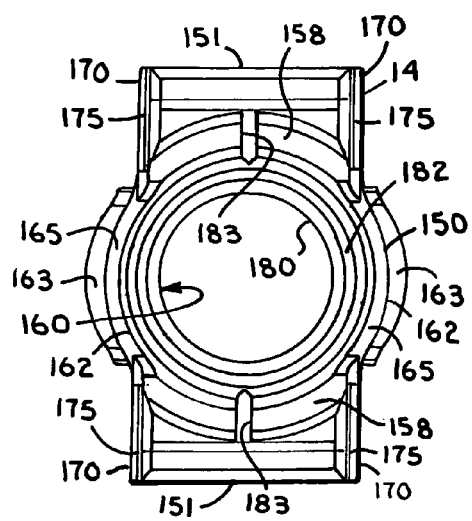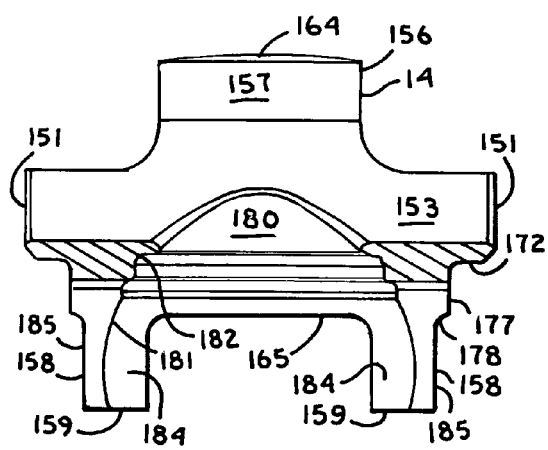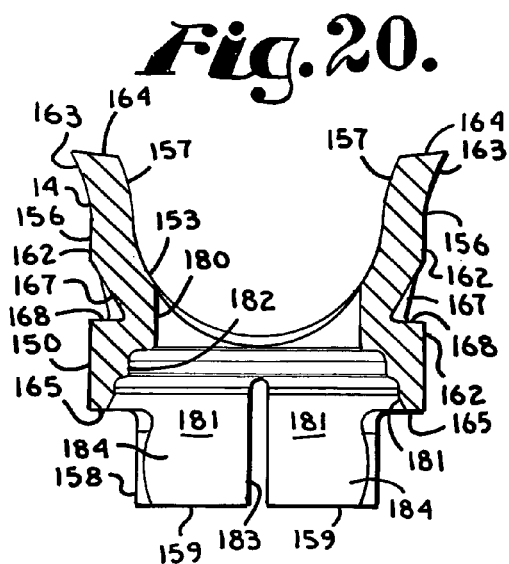

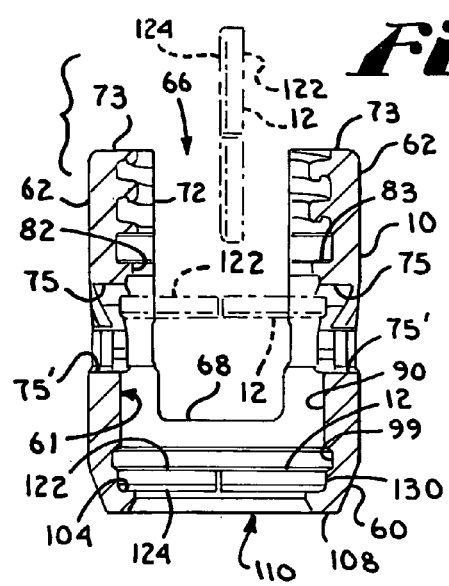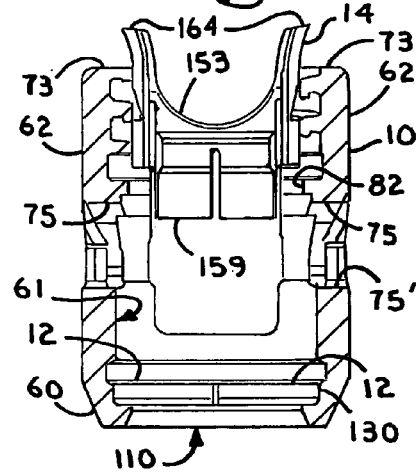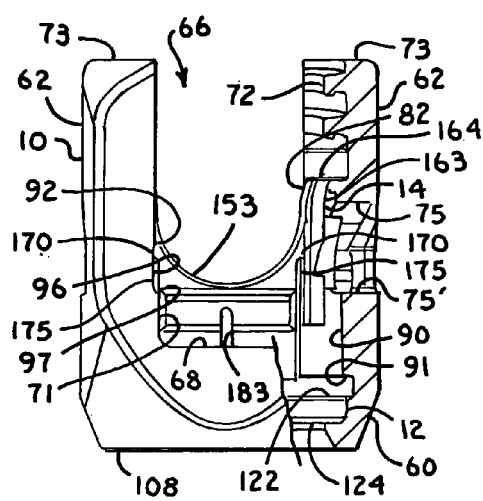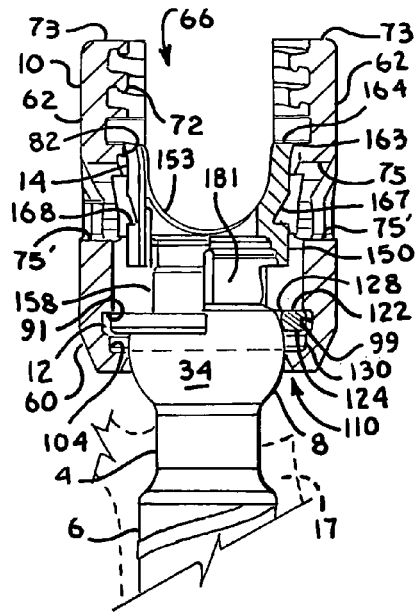

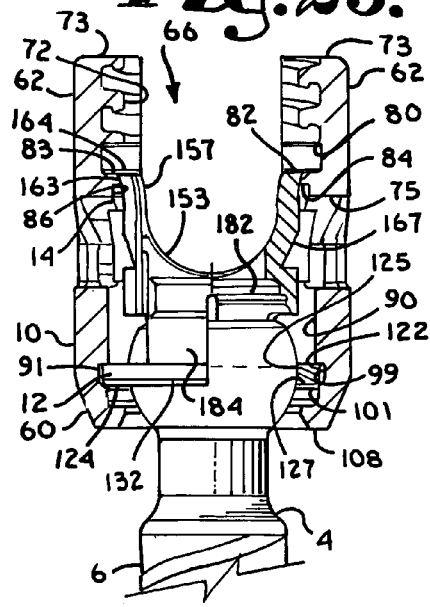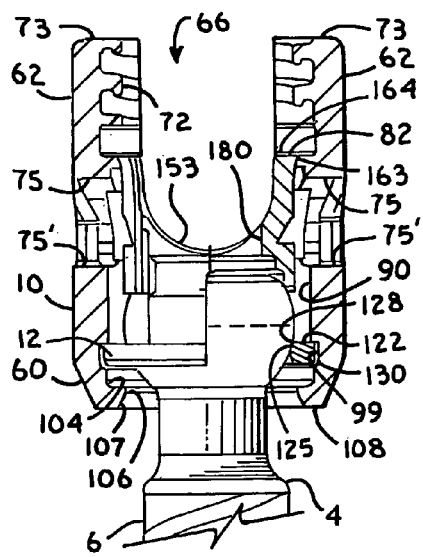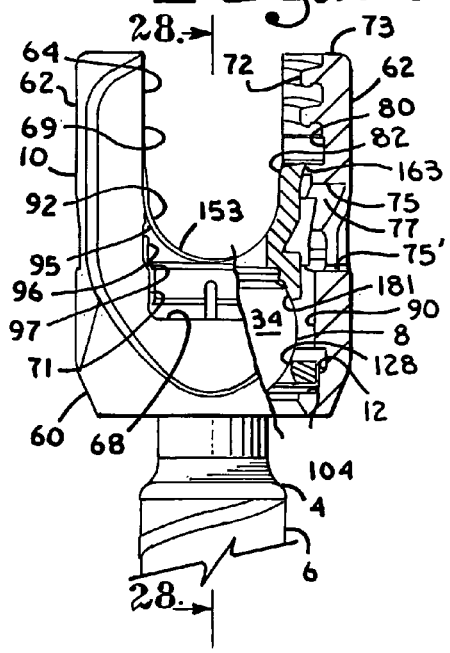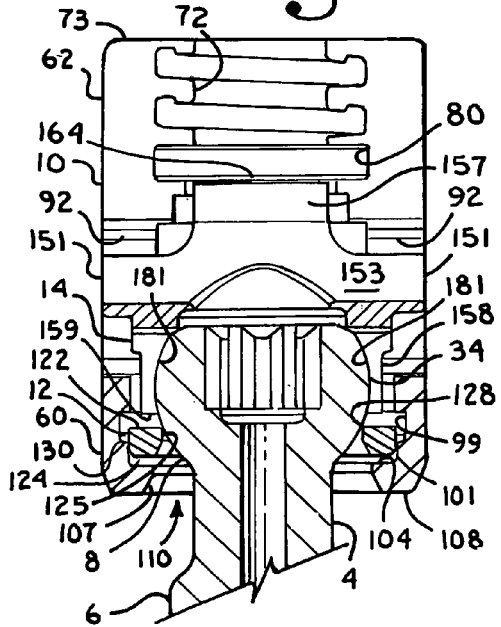

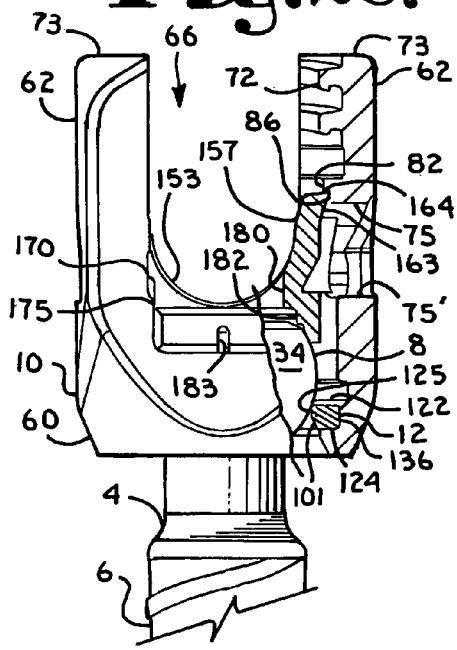
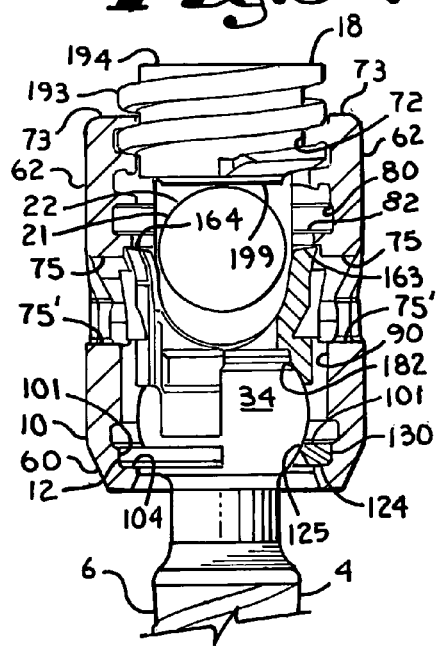
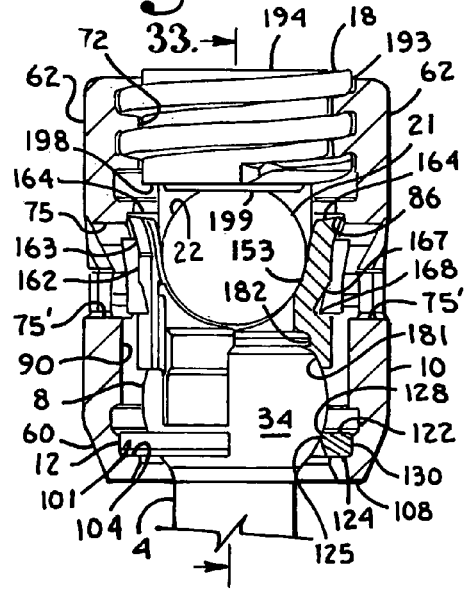
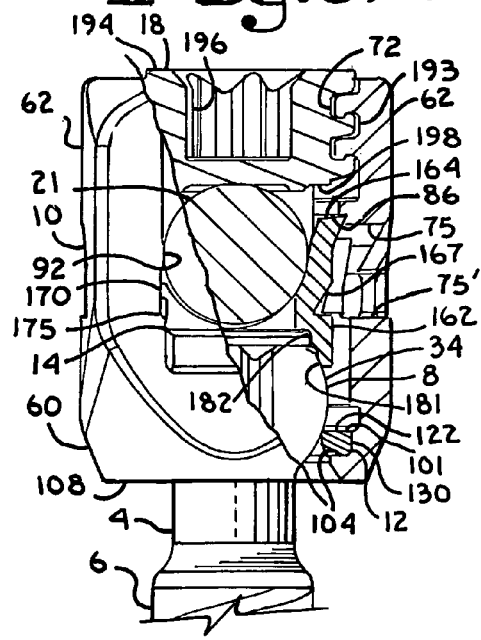

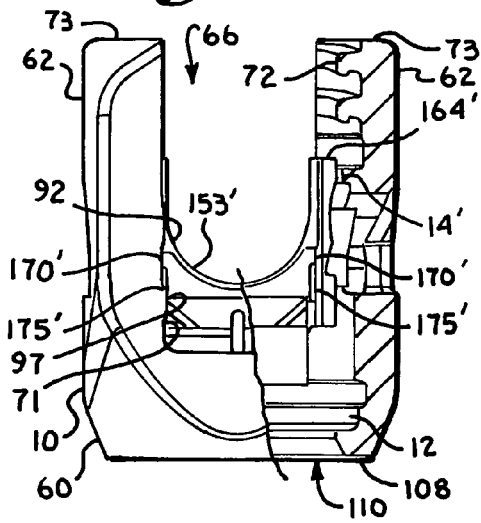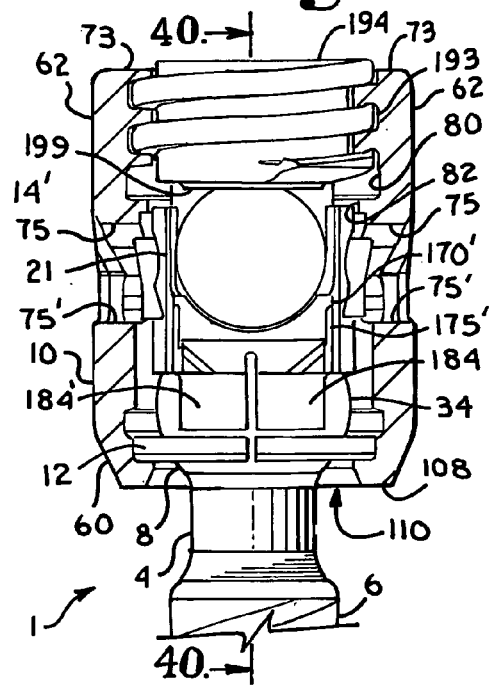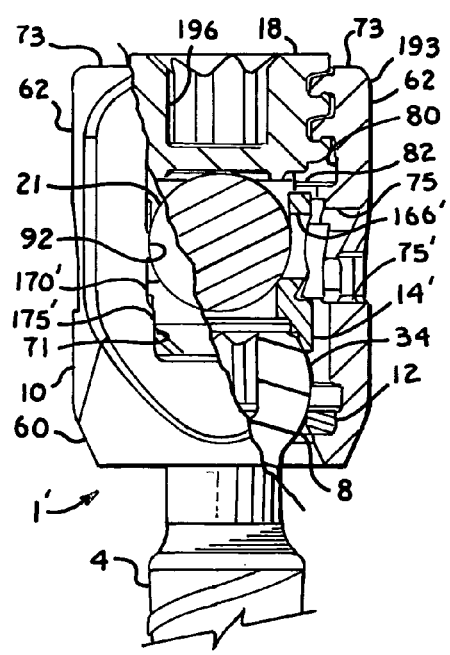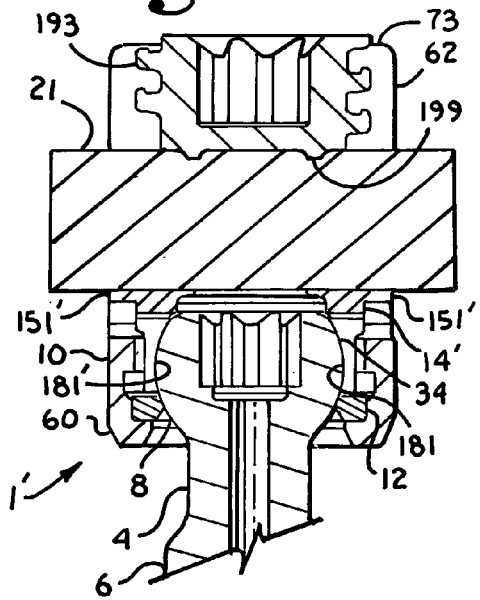

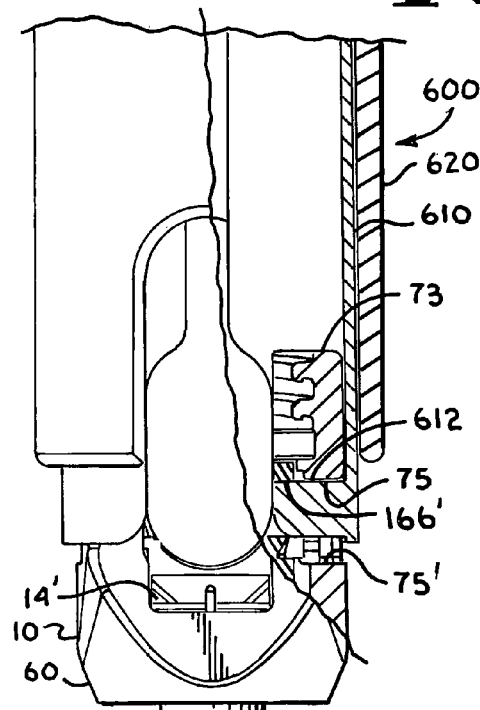
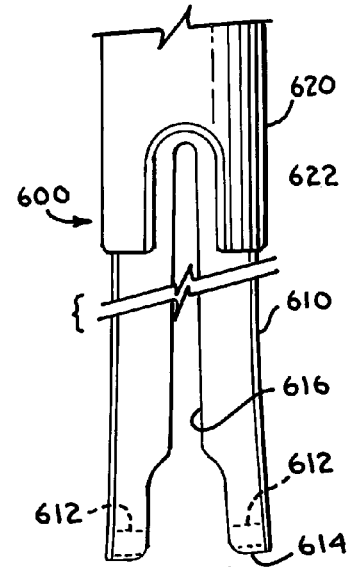
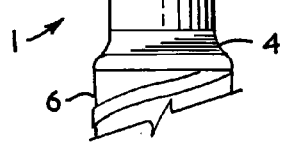
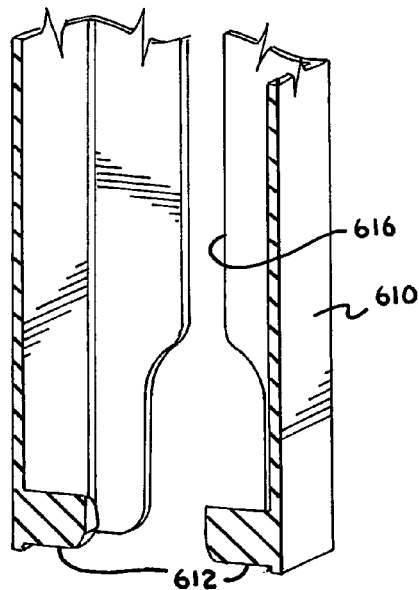

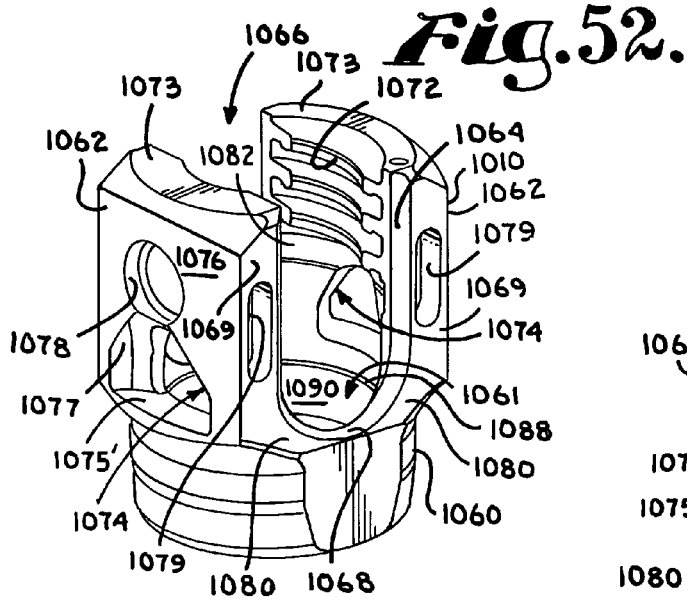//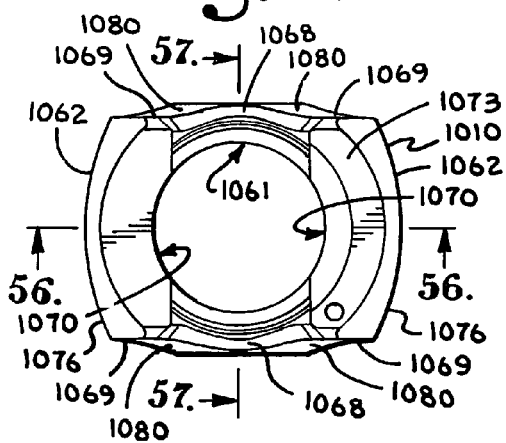//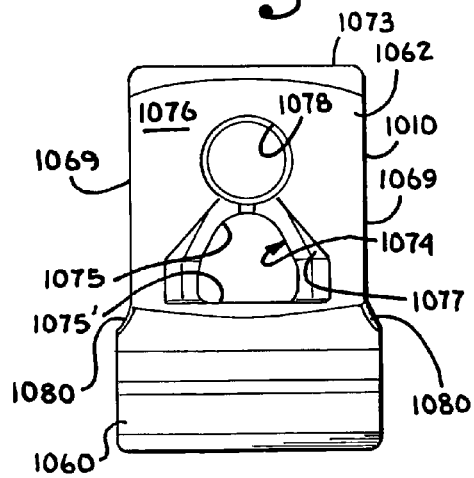//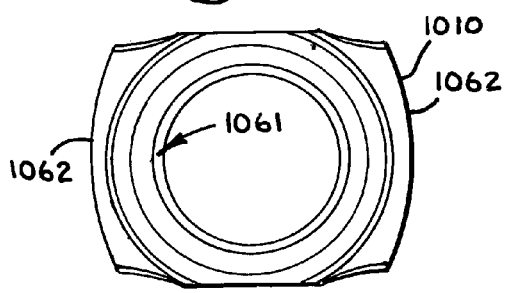

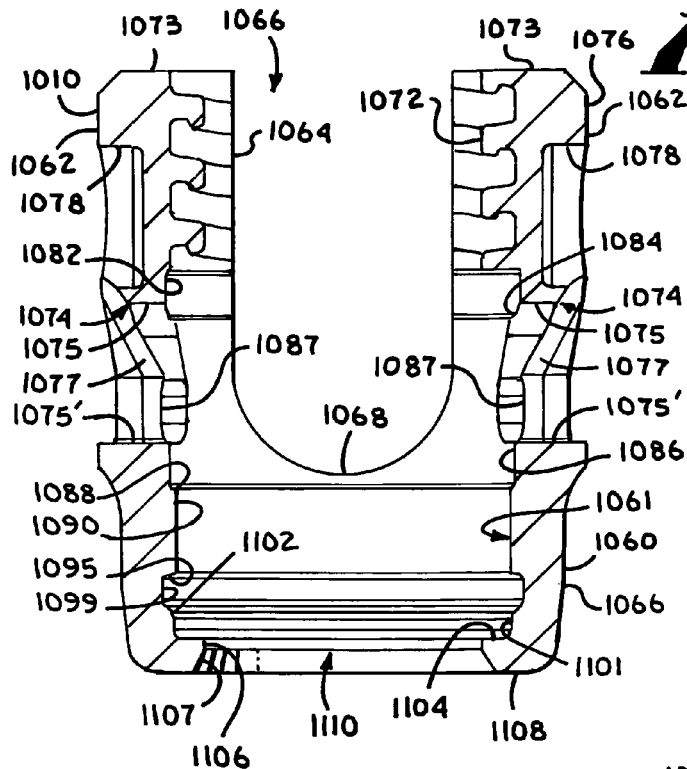
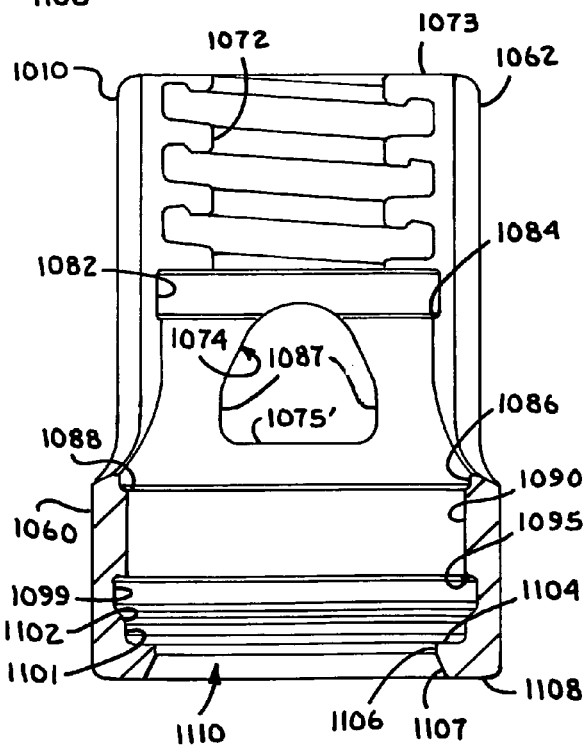

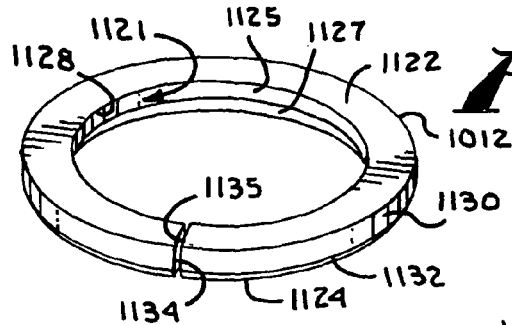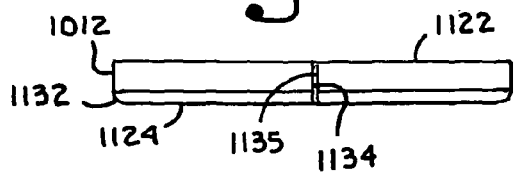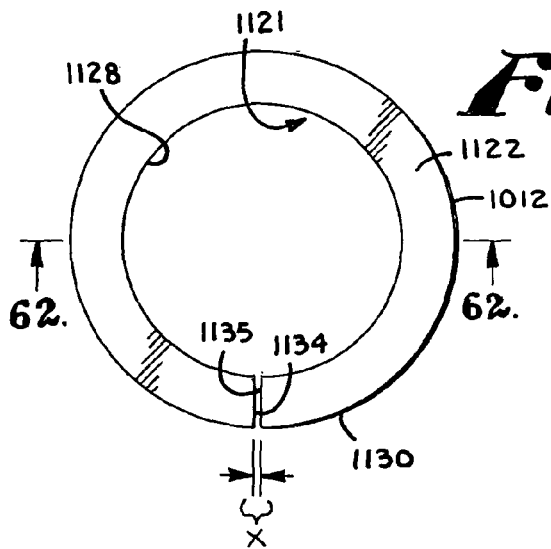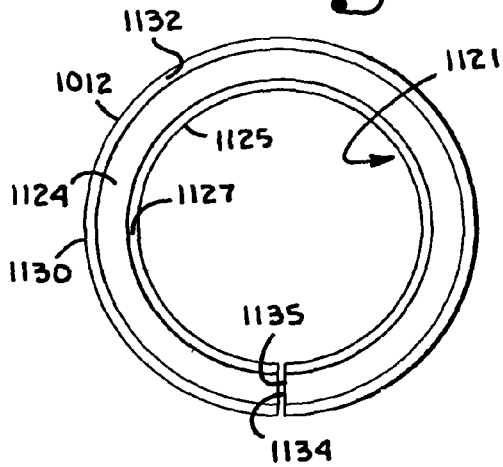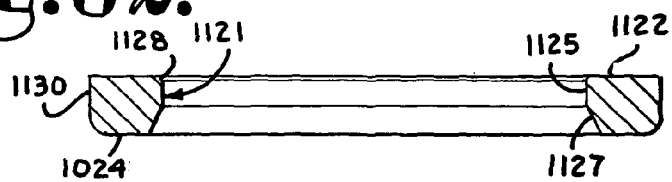

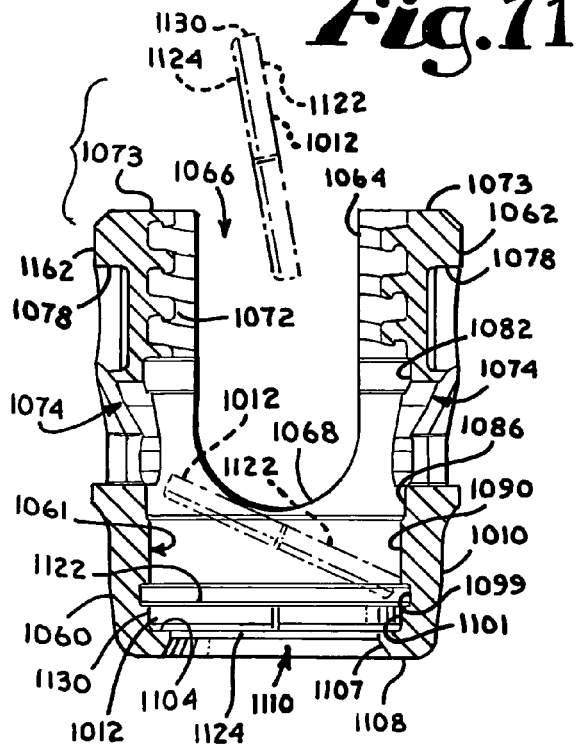
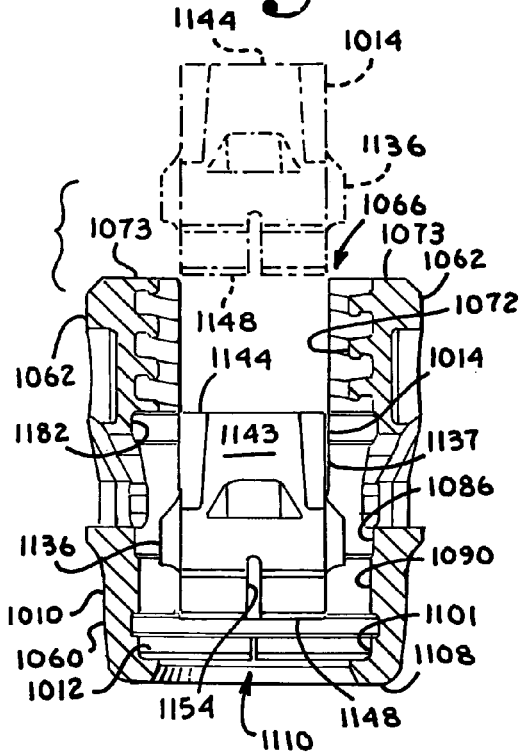
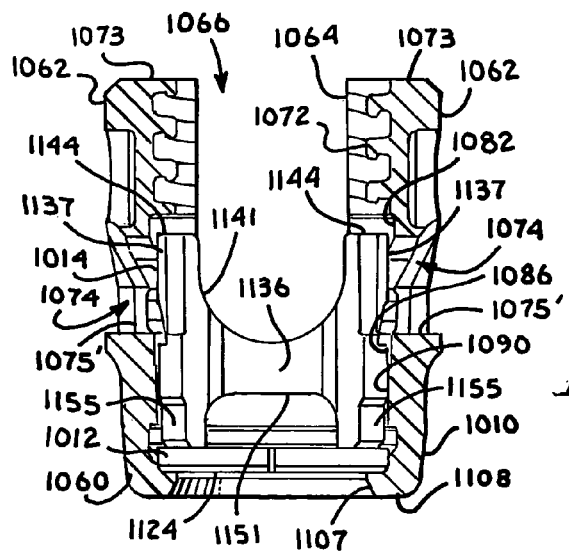

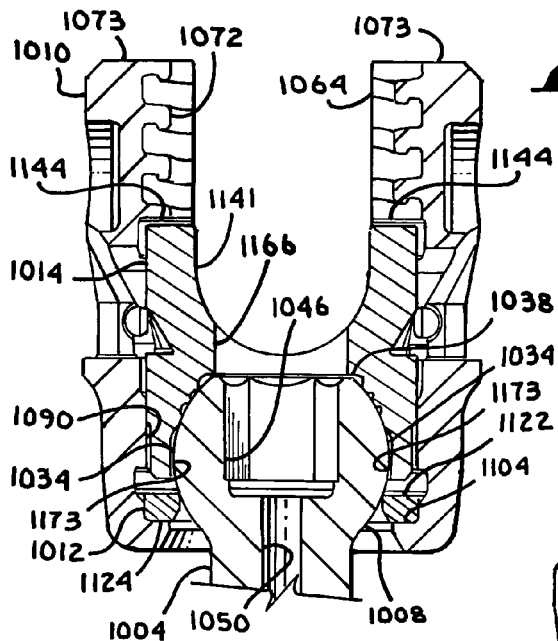
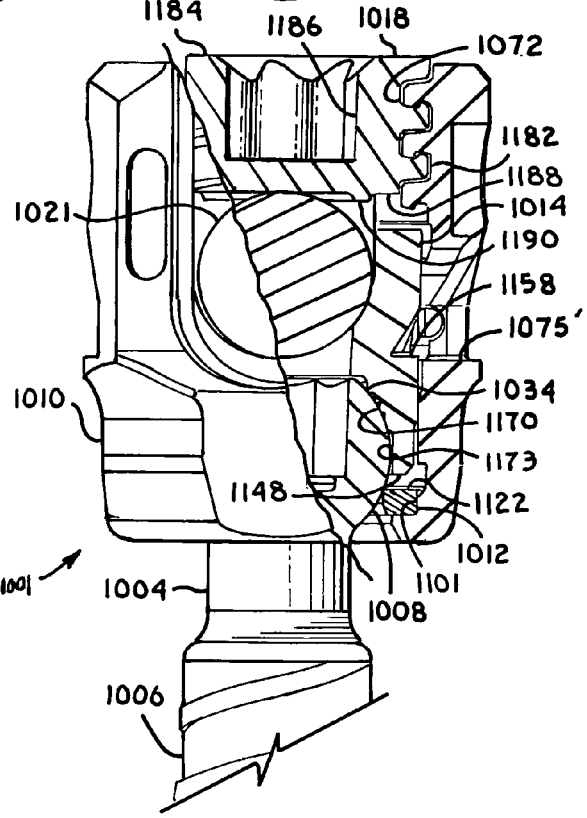
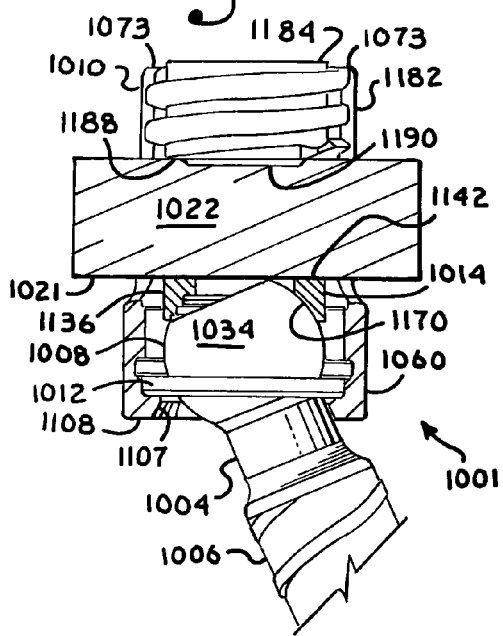

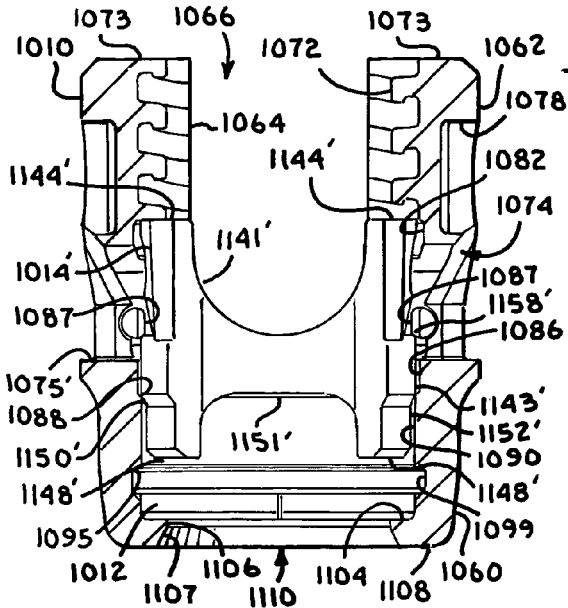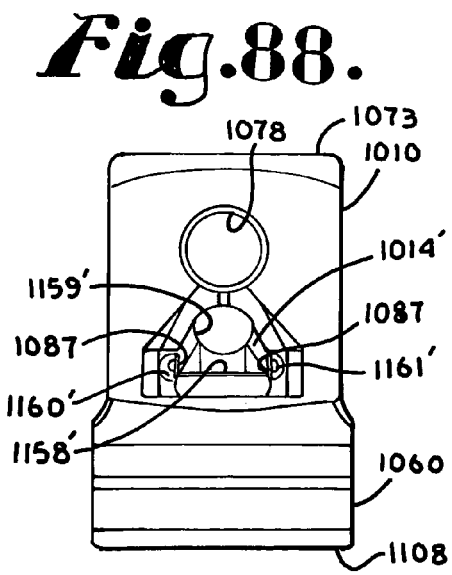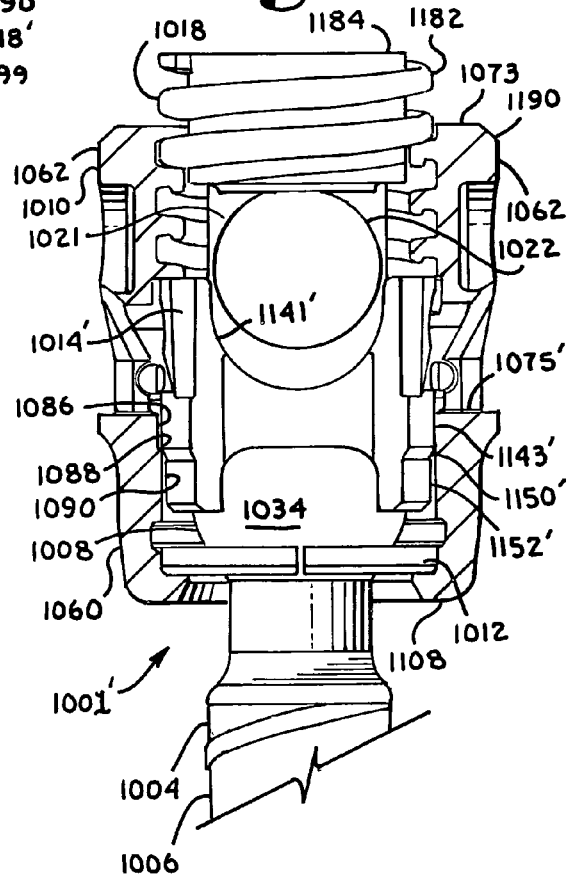

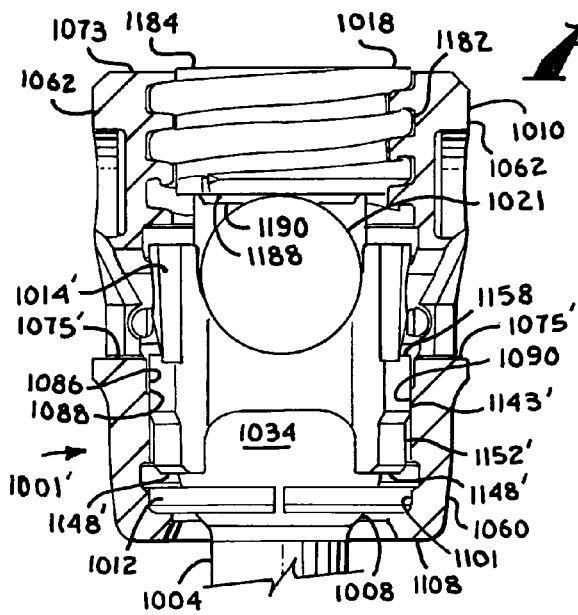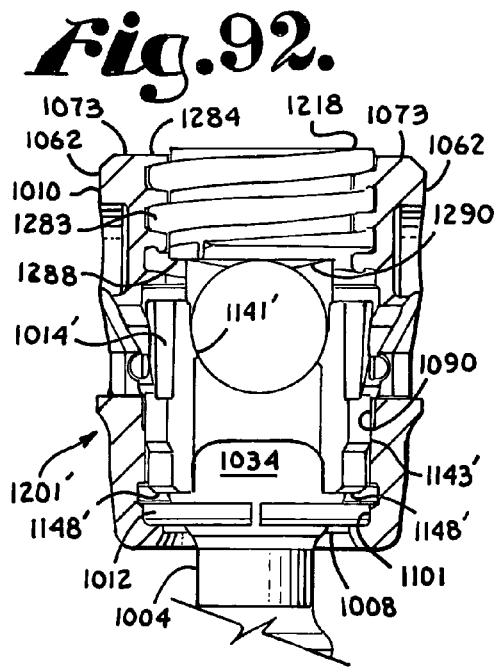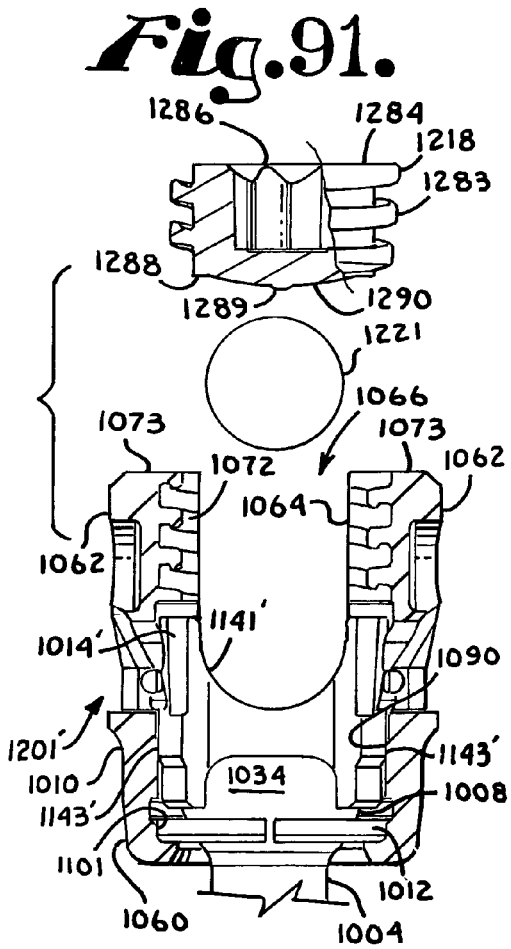

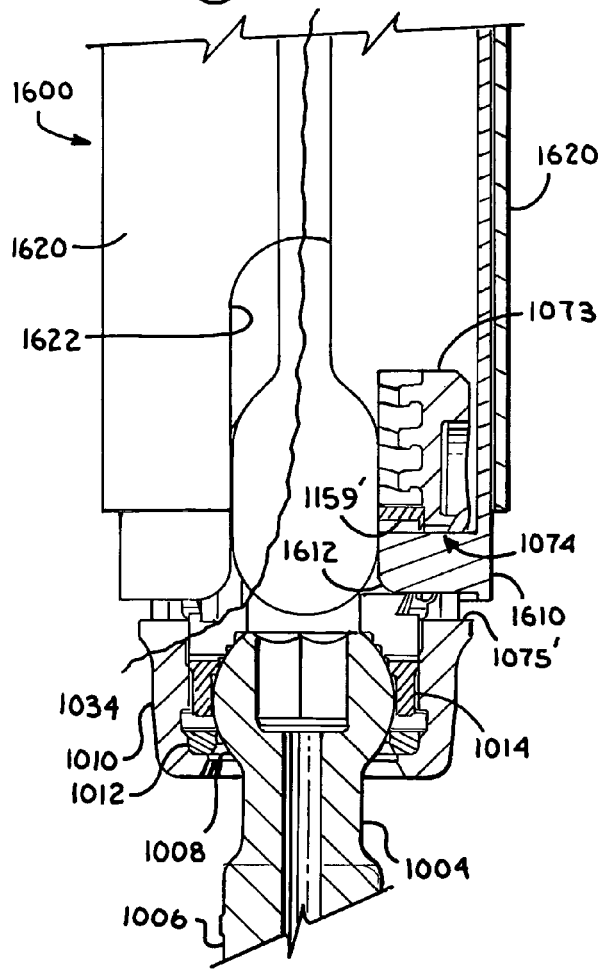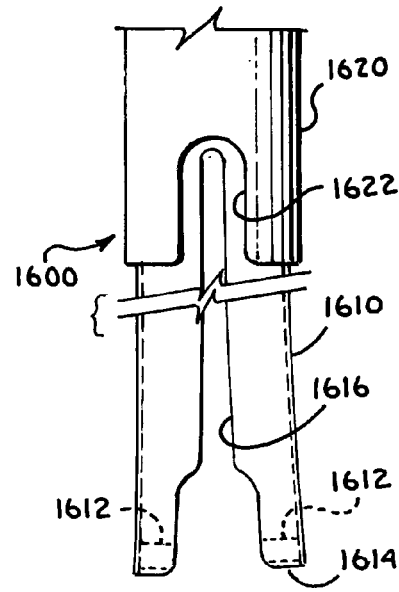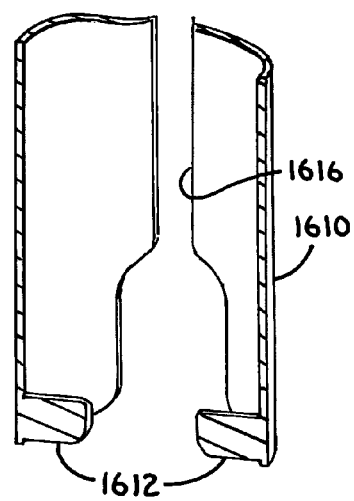

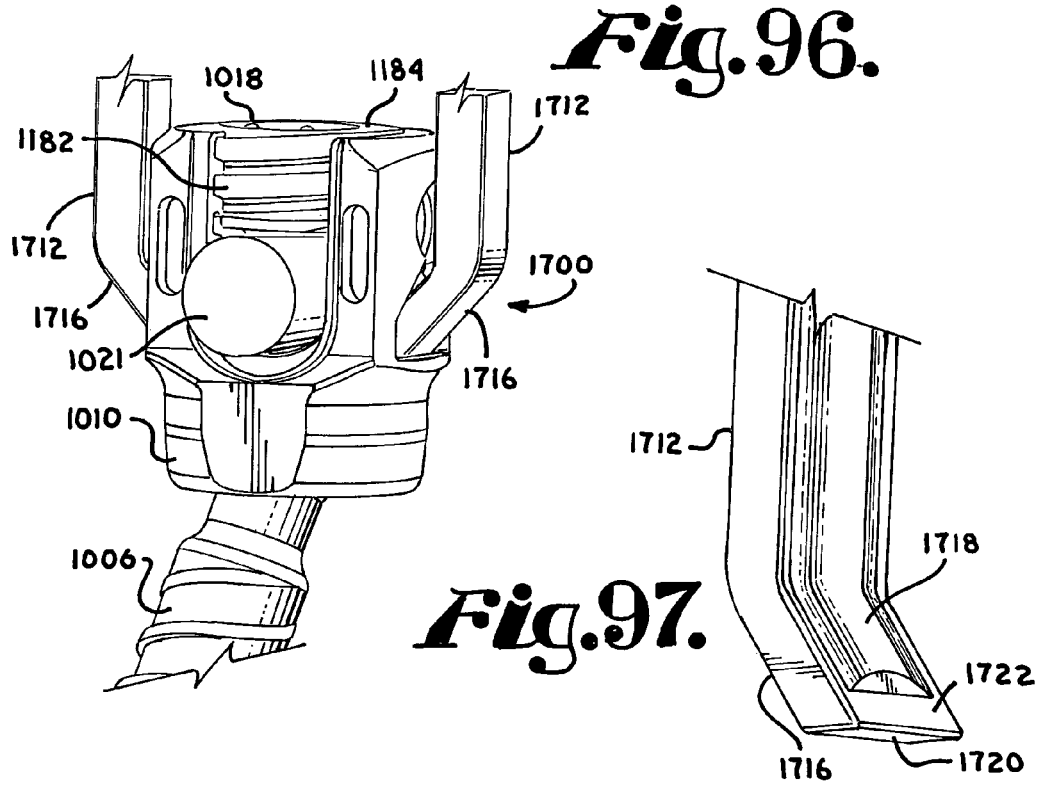
*Fig.96.*
*Fig.97.*
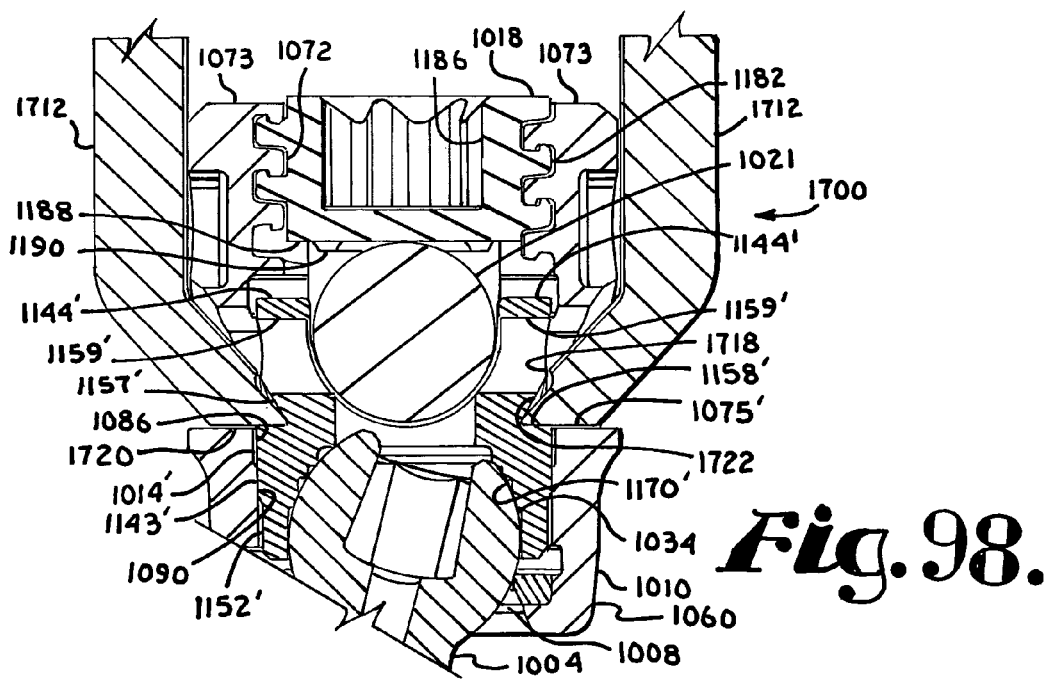
*Fig.98.*

US 9,980,753 B2

PIVOTAL ANCHOR WITH SNAP-IN-PLACE INSERT HAVING ROTATION BLOCKING EXTENSIONS

This application claims the benefit of U.S. Provisional Patent Application Ser. No. 61/460,267 filed Dec. 29, 2010 and U.S. Provisional Patent Application Ser. No. 61/463,037 filed Feb. 11, 2011, both of which are incorporated by reference herein. This applications is also a continuation-in-part of U.S. patent application Ser. No. 13/373,289 filed Nov. 9, 2011 that claims the benefit of U.S. Provisional Patent Application Ser. No. 61/456,649 filed Nov. 10, 2010 and U.S. Provisional Patent Application Ser. No. 61/460,234 filed Dec. 29, 2010, all of which are incorporated by reference herein. This application is also a continuation-in-part of U.S. patent application Ser. No. 12/924,802 filed Oct. 5, 2010 that claims the benefit of the following U.S. Provisional Patent Application Ser. Nos. 61/278,240, filed Oct. 5, 2009; 61/336,911, filed Jan. 28, 2010; 61/343,737 filed May 3, 2010; 61/395,564 filed May 14, 2010; 61/395,752 filed May 17, 2010; 61/396,390 filed May 26, 2010; 61/398,807 filed Jul. 1, 2010; 61/400,504 filed Jul. 29, 2010; 61/402,959 filed Sep. 8, 2010; 61/403,696 filed Sep. 20, 2010; and 61/403,915 filed Sep. 23, 2010, all of which are incorporated by reference herein. This application is also a continuation-in-part of U.S. patent application Ser. No. 12/802,849 filed Jun. 15, 2010 that claims the benefit of U.S. Provisional Patent Application Ser. No. 61/268,708 filed Jun. 15, 2009, both of which are incorporated by reference herein. U.S. patent application Ser. No. 12/802,849 also claims the benefit of U.S. Provisional Patent Application Ser. Nos. 61/268,708, filed Jun. 15, 2009; 61/270,754, filed Jul. 13, 2009; 61/336,911, filed Jan. 28, 2010; 61/395,564, filed May 14, 2010; 61/395,752, filed May 17, 2010; 61/396,390 filed May 26, 2010.

BACKGROUND OF THE INVENTION

The present invention is directed to polyaxial bone screw shanks with heads for use in bone surgery, more specifically to spinal surgery and particularly to such screws with receiver member assemblies including compression or pressure inserts and expansion-only split retainers to snap over, capture and retain the bone screw shank head in the receiver member assembly and later fix the bone screw shank with respect to the receiver assembly.

Bone screws are utilized in many types of spinal surgery in order to secure various implants to vertebrae along the spinal column for the purpose of stabilizing and/or adjusting spinal alignment. Although both closed-ended and open-ended bone screws are known, open-ended screws are particularly well suited for connections to rods and connector arms, because such rods or arms do not need to be passed through a closed bore, but rather can be laid or urged into an open channel within a receiver or head of such a screw. Generally, the screws must be inserted into the bone as an integral unit along with the head, or as a preassembled unit in the form of a shank and pivotal receiver, such as a polyaxial bone screw assembly.

Typical open-ended bone screws include a threaded shank with a pair of parallel projecting branches or arms which form a yoke with a U-shaped slot or channel to receive a rod. Hooks and other types of connectors, as are used in spinal fixation techniques, may also include similar open ends for receiving rods or portions of other fixation and stabilization structure.

A common approach for providing vertebral column support is to implant bone screws into certain bones which then in turn support a longitudinal structure such as a rod, or are supported by such a rod. Bone screws of this type may have a fixed head or receiver relative to a shank thereof, or may be of a polyaxial screw nature. In the fixed bone screws, the rod receiver head cannot be moved relative to the shank and the rod must be favorably positioned in order for it to be placed within the receiver head. This is sometimes very difficult or impossible to do. Therefore, polyaxial bone screws are commonly preferred. Open-ended polyaxial bone screws typically allow for a loose or floppy rotation of the head or receiver about the shank until a desired rotational position of the receiver is achieved by fixing such position relative to the shank during a final stage of a medical procedure when a rod or other longitudinal connecting member is inserted into the receiver, followed by a locking screw or other closure. This floppy feature can be, in some cases, undesirable and make the procedure more difficult. Also, it is often desirable to insert the bone screw shank separate from the receiver or head due to its bulk which can get in the way of what the surgeon needs to do. Such screws that allow for this capability are sometimes referred to as modular polyaxial screws.

With specific reference to modular snap-on or pop-on polyaxial pedicle screw systems having shank receiver assemblies, the prior art has shown and taught the concept of the receiver and certain retainer parts forming an assembly wherein a contractile locking engagement between the parts is created to fix the shank head with respect to the receiver and retainer. The receiver and shank head retainer assemblies in the prior art have included a contractile retainer ring and/or a lower pressure insert with an expansion and contraction collet-type of structure having contractile locking engagement for the shank head due to direct contact between the retainer and/or the collet structure with the receiver resulting in contraction of the retainer ring and/or the collet-type structure of the insert against the shank head.

The prior art for modular polyaxial screw assemblies has also shown and taught that the contact surfaces on the outside of the collect and/or retainer and the inside of the receiver can be tapered, conical, radiused, spherical, curvate, multi-curvate, rounded, as well as other configurations to create a contractile type of locking engagement for the shank head with respect to the receiver.

In addition, the prior art for modular polyaxial screw assemblies has shown and taught that the shank head can both enter and escape from a collet-like structure on the insert or from the retainer when the insert or retainer is in the up position and within an expansion recess or chamber of the receiver. This is the case unless the insert and/or the retainer are blocked from being able to be pushed back up into receiver bore or cavity.

SUMMARY OF THE INVENTION

The present invention differentiates from the prior art by not allowing the receiver to be removed from the shank head once the parts are snapped-on and connected. This is true even if the retainer can go back up into the expansion chamber. This approach or design has been found to be more secure and to provide more resistance to pull-out forces compared to the prior art for modular polyaxial screw designs. Collect-like structures extending downwardly from lower pressure inserts, when used in modular polyaxial screw designs, as shown in the prior art, have been found to be somewhat weak with respect to pull-out forces encountered during some spinal reduction procedures. The present invention is designed to solve these problems.

The present invention also differentiates from all of the prior art by providing a split retainer ring and a cooperating insert with a collet-like lower super structure portion, wherein the super structure does not participate at all in the locking engagement for the shank head with respect to the receiver. The expansion-only split or open retainer ring in the present invention is positioned entirely below the shank head hemisphere in the receiver and can be a stronger, more substantial structure to resist larger pull out forces on the assembly. The retainer ring base can also be better supported on a generally horizontal loading surface near the lower opening in the bottom of the receiver. This design has been found to be stronger and more secure when compared to that of the prior art which uses some type of contractile locking engagement between the parts, as described above; and, again, once assembled it cannot be disassembled.

Thus, a polyaxial bone screw assembly according to the invention includes a shank having an integral upper portion or head and a body for fixation to a bone; a separate receiver defining an upper open channel, a central bore, a lower cavity and a lower opening; one of (a) a top drop and rotate friction fit lower compression insert having super structure providing temporary friction fit with the shank head and (b) a top drop, non-rotatable friction fit insert having a seating surface extending between front and rear faces of arms of the receiver and super structure providing temporary friction fit with the shank head; and a resilient expansion-only split retainer for capturing the shank head in the receiver lower cavity, the shank head being frictionally engaged with, but still movable in a non-floppy manner with respect to the friction fit insert and the receiver prior to locking of the shank into a desired configuration. In some embodiments the insert completely extends between receiver arms that define the receiver channel and thus remains aligned with and cannot rotate with respect to the receiver at any stage of assembly. In other embodiments, the top drop and rotate insert is fixed with respect to the receiver by pressing or crimping portions of the receiver against the insert. The insert operatively engages the shank head and is spaced from the retainer by the shank head that is snapped into insert super structure illustrated as resilient panels. The shank is finally locked into a fixed position relative to the receiver by frictional engagement between a portion of the insert located above the super structure and the split retainer, as described previously, due to a downward force placed on the compression insert by a closure top pressing on a rod, or other longitudinal connecting member, captured within the receiver bore and channel. In the illustrated embodiments, retainers and inserts are downloaded into the receiver, but uploaded retainer embodiments are also foreseen. The shank head can be positioned into the receiver lower cavity at the lower opening thereof prior to or after insertion of the shank into bone. Some compression inserts include a lock and release feature for independent locking of the polyaxial mechanism so the screw can be used like a fixed monoaxial screw. The shank can be cannulated for minimally invasive surgery applications. The receiver is devoid of any type of spring tabs or collet-like structures. The pressure insert and/or the retainer are both devoid of any type of receiver-retainer contractile locking engagements with respect to the shank head. In some embodiments, the insert can also have resilient outwardly and upwardly extending arms which are deployed into openings in the receiver cavity so that the retainer and captured shank head are stabilized and retained in the region of the receiver locking chamber once they enter into such lower portion of the receiver cavity. In this way, the shank head and retainer cannot go back up into the receiver cavity.

Again, a pre-assembled receiver, friction fit compression insert and split retainer may be "pushed-on", "snapped-on" or "popped-on" to the shank head prior to or after implantation of the shank into a vertebra. Such a "snapping on" procedure includes the steps of uploading the shank head into the receiver lower opening, the shank head pressing against the base of the split retainer ring and expanding the resilient retainer out into an expansion portion or chamber of the receiver cavity followed by an elastic return of the retainer back to an original or near nominal shape thereof after the hemisphere of the shank head or upper portion passes through the ring-like retainer. The shank head also enters into the friction fit lower portion of the insert, the panels of the friction fit portion of the insert snapping onto the shank head as the retainer returns to a neutral or close to neutral orientation, providing a non-floppy connection between the insert and the shank head. The friction fit between the shank head and the insert is temporary and not part of the final locking mechanism. In the illustrated embodiment, when the shank is ultimately locked between the compression insert and the lower portion of the retainer, the friction fit collet-like panels of the insert are no longer in a tight friction fit engagement with the shank head and they are not in contact with the receiver. The final fixation occurs as a result of a locking expansion-type of contact between the shank head and the split retainer and an expansion-type of non-tapered locking engagement between the retainer ring and the locking chamber in the lower portion of the receiver cavity. The retainer can expand more in the upper portion or expansion chamber of the receiver cavity to allow the shank head to pass through, but has restricted expansion to retain the shank head when the retainer is against the locking chamber surfaces in the lower portion of the receiver cavity and the shank head is forced down against the retainer ring during final locking. In some embodiments, when the polyaxial mechanism is locked, portions of the insert are forced or wedged against opposing surfaces of the receiver resulting in an interference, non-contractile locking engagement, allowing for adjustment or removal of the rod or other connecting member without loss of a desired angular relationship between the shank and the receiver. This independent, non-contractile locking feature allows the polyaxial screw to function like a fixed monoaxial screw.

The lower pressure insert may also be configured to be independently locked by a tool or instrument, thereby allowing the pop-on polyaxial screw to be distracted, compressed and/or rotated along and around the rod to provide for improved spinal correction techniques. Such a tool engages the pop-on receiver from the sides and then engages the insert to force the insert down into a locked position within the receiver. With the tool still in place and the correction maintained, the rod is then locked within the receiver channel by a closure top followed by removal of the tool. This process may involve multiple screws all being manipulated simultaneously with multiple tools to achieve the desired correction.

Objects of the invention further include providing apparatus and methods that are easy to use and especially adapted for the intended use thereof and wherein the tools are comparatively inexpensive to produce. Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 14 is an enlarged perspective view of the insert of FIG. 1.

FIG. 15 is another enlarged perspective view of the insert of FIG. 1.

FIG. 16 is a front elevational view of the insert of FIG. 14.

FIG. 17 is a reduced top plan view of the insert of FIG. 14.

FIG. 18 is a bottom plan view of the insert of FIG. 14.

FIG. 19 is an enlarged cross-sectional view taken along the line 19-19 of FIG. 17.

FIG. 20 is an enlarged cross-sectional view taken along the line 20-20 of FIG. 17.

FIG. 21 is an enlarged front elevational view of the retainer and receiver of FIG. 1 with portions of the receiver broken away to show the detail thereof, the retainer being shown downloaded into the receiver (in phantom) to an inserted stage of assembly.

FIG. 22 is a front elevational view of the retainer and receiver with portions broken away, similar to what is shown in FIG. 21, showing the insert of FIG. 1, also in front elevational view, in an initial stage of assembly.

FIG. 23 is an enlarged front elevational view of the retainer, receiver and insert with portions broken away, similar to what is shown in FIG. 22, showing the insert in a subsequent stage of assembly, resilient arms of the insert pressing against inner surfaces of the receiver.

FIG. 24 is a reduced front elevational view with portions broken away, similar to FIG. 23, and further showing an enlarged and partial shank of FIG. 1 in a first stage of assembly with the retainer, a hemisphere of the shank head and a vertebra portion both being shown in phantom.

FIG. 25 is a partial front elevational view with portions broken away, similar to FIG. 24, showing the retainer in an expanded state about a mid-portion of the shank head, the head hemisphere shown in phantom.

FIG. 26 is a partial front elevational view with portions broken away, similar to FIG. 25, the shank upper portion or head fully captured by the retainer.

FIG. 27 is another partial front elevational view with portions broken away, similar to FIG. 26, the shank upper portion or head being in frictional engagement with lower panels of the insert.

FIG. 28 is an enlarged and partial cross-sectional view taken along the line 28-28 of FIG. 27.

FIG. 29 is a partial front elevational view with portions broken away, similar to FIG. 27, the shank upper portion and retainer being shown pulled down into a seated position within the lower receiver cavity, the insert arms in a substantially neutral state, capturing the insert below a ledge of the receiver.

FIG. 30 is a partial front elevational view with portions broken away of all of the components shown in FIG. 1, the assembly as in FIG. 29 being shown in a stage of assembly with the rod and closure top.

FIG. 31 is an enlarged and partial front elevational view with portions broken away, similar to FIG. 30, shown in a final locking position.

FIG. 32 is another enlarged and partial front elevational view with portions broken away, similar to FIG. 31.

FIG. 37 is an enlarged front elevational view with portions broken away of the receiver and retainer of FIG. 1 and the insert of FIG. 34 in reduced front elevation, the insert shown captured within the receiver and in an un-locked shipping position.

FIG. 38 is a partial front elevational view of the shank, receiver, retainer, rod and closure of FIG. 1, with portions broken away and assembled with the locking insert as shown in FIG. 37, but in a locked stage of assembly.

FIG. 39 is an enlarged and partial front elevational view, similar to FIG. 38, illustrating the interference locking of the insert against the receiver.

FIG. 40 is an enlarged and partial cross-sectional view taken along the line 40-40 of FIG. 38.

FIG. 43 is a reduced and partial front elevational view with portions broken away of the assembly of FIG. 42 without the alternative rod and closure top, and further showing unlocking of the insert from the receiver with a two-piece tool having an inner insert engaging portion and an outer tubular holding portion.

FIG. 44 is a reduced and partial front elevational view of the two-piece tool of FIG. 43, holding prongs of the inner insert engaging portion being shown in phantom.

FIG. 45 is an enlarged and partial perspective view of the inner insert engaging portion of the tool shown in FIG. 44 with portions broken away to show the detail thereof.

FIG. 52 is an enlarged perspective view of the receiver of FIG. 49.

FIG. 53 is a side elevational view of the receiver of FIG. 52.

FIG. 54 is a top plan view of the receiver of FIG. 52.

FIG. 55 is a bottom plan view of the receiver of FIG. 52.

FIG. 56 is an enlarged cross-sectional view taken along the line 56-56 of FIG. 54.

FIG. 57 is an enlarged cross-sectional view taken along the line 57-57 of FIG. 54.

FIG. 58 is an enlarged perspective view of the retainer of FIG. 49.

FIG. 59 is a front elevational view of the retainer of FIG. 58.

FIG. 60 is a top plan view of the retainer of FIG. 58.

FIG. 61 is a bottom plan view of the retainer of FIG. 58.

FIG. 62 is an enlarged cross-sectional view taken along the line 62-62 of FIG. 60.

FIG. 71 is an enlarged front elevational view of the retainer and receiver of FIG. 49 with portions of the receiver broken away to show the detail thereof and intermediate positions of the retainer while being downloaded into the receiver being shown in phantom.

FIG. 72 is a front elevational view with portions broken away, similar to FIG. 71, further showing the insert of FIG. 49 in enlarged side elevation, with an early stage of assembly of the insert being shown in phantom.

FIG. 73 is a front elevational view with portions broken away, similar to FIG. 72, showing the insert rotated within the receiver during an assembly stage subsequent to that shown in FIG. 72.

FIG. 81 is an enlarged partial front elevational view of the assembly as shown in FIG. 80, with further portions broken away to show the engagement between the shank upper portion and the insert.

FIG. 82 is a reduced partial front elevational view with portions broken away, similar to FIGS. 80 and 81, showing the assembly in a locked position with the rod and closure top of FIG. 49, also shown in front elevation with portions broken away.

FIG. 83 is a reduced and partial side elevational view of the assembly of FIG. 82.

FIG. 87 is an enlarged front elevational view of the receiver and retainer of FIG. 49 shown assembled with the insert of FIG. 84, also in front elevation, with portions broken away to show the detail thereof.

FIG. 88 is a reduced side elevational view of the assembly of FIG. 87.

FIG. 89 is a reduced front elevational view of the receiver (with portions broken away), retainer and insert of FIG. 87 further shown assembled with a shank of FIG. 49, shown in partial front elevation, and in a stage of assembly with the rod and closure top of FIG. 49, also shown in front elevation.

FIG. 90 is an enlarged and partial front elevational view with portions broken away, similar to FIG. 89 but showing the insert in locked assembly with the receiver, retainer, rod and closure top.

FIG. 91 is a reduced partial front elevational view with portions broken away, similar to FIG. 90, but shown with the rod and closure top removed, the locking insert remaining in locked relation with respect to the receiver, and further being shown with an alternative deformable rod and cooperating closure top, shown in exploded view.

FIG. 92 is a partial front elevational view with portions broken away, similar to FIG. 91 showing the alternative deformable rod and closure top in locked relationship with the rest of the assembly.

FIG. 93 is a reduced and partial front elevational view with portions broken away of the assembly of FIG. 91 without the alternative rod and closure top, and further showing unlocking of the insert from the receiver with a two-piece tool having an inner insert engaging portion and an outer tubular holding portion.

FIG. 94 is a reduced and partial front elevational view of the two-piece tool of FIG. 93, holding prongs of the inner insert engaging portion being shown in phantom.

FIG. 95 is an enlarged and partial perspective view of the inner insert engaging portion of the tool shown in FIG. 94 with portions broken away to show the detail thereof.

FIG. 96 is an enlarged and partial perspective view of an assembly identical to that shown in FIG. 90 with the exception of the shank being at an angle with respect to the receiver and further showing an alternative locking tool for independently locking the shank with respect to the receiver when the closure top and rod are in a loose, unlocked relationship with the receiver.

FIG. 97 is a partial perspective view of a portion of the locking tool of FIG. 96.

FIG. 98 is an enlarged and partial front elevational view of the assembly and locking tool of FIG. 96 with portions broken away to show the detail thereof.

DETAILED DESCRIPTION OF THE INVENTION

Figure 1:
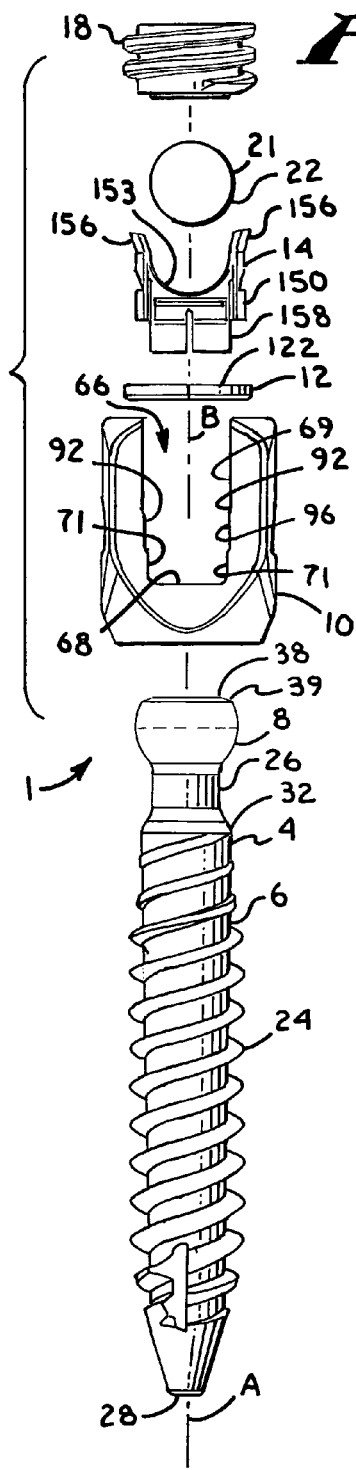
FIG. 1 is an exploded front elevational view of a polyaxial bone screw assembly according to the present invention including a shank, a receiver, an open expansion-only retainer and a friction fit lower compression insert, further shown with a portion of a longitudinal connecting member in the form of a rod and a closure top.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of the bone attachment structures in actual use.

With reference to FIGS. 1-33 the reference number 1 generally represents a polyaxial bone screw apparatus or assembly according to the present invention. The assembly 1 includes a shank 4, that further includes a body 6 integral with an upwardly extending upper portion or head structure 8; a receiver 10; an open ring retainer 12, and a compression or pressure insert 14 having structure for friction fit non-locking engagement with the shank head 8. The receiver 10, retainer 12 and compression insert 14 are initially assembled and may be further assembled with the shank 4 either prior or subsequent to implantation of the shank body 6 into a vertebra 17 (see FIG. 24), as will be described in greater detail below. FIGS. 1 and 31-33 further show a closure structure 18 for capturing a longitudinal connecting member, for example, a rod 21 which in turn engages the compression insert 14 that presses against the shank upper portion 8 into fixed frictional contact with the retainer 12, so as to capture, and fix the longitudinal connecting member 21 within the receiver 10 and thus fix the member 21 relative to the vertebra 17. The illustrated rod 21 is hard, stiff, non-elastic and cylindrical, having an outer cylindrical surface 22. It is foreseen that in other embodiments, the rod 21 may be elastic, deformable and/or of different materials and cross-sectional geometries. The receiver 10 and the shank 4 cooperate in such a manner that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure.

Figure 2:
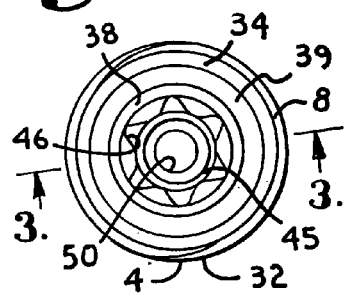
FIG. 2 is an enlarged top plan view of the shank of FIG. 1.
Figure 3:
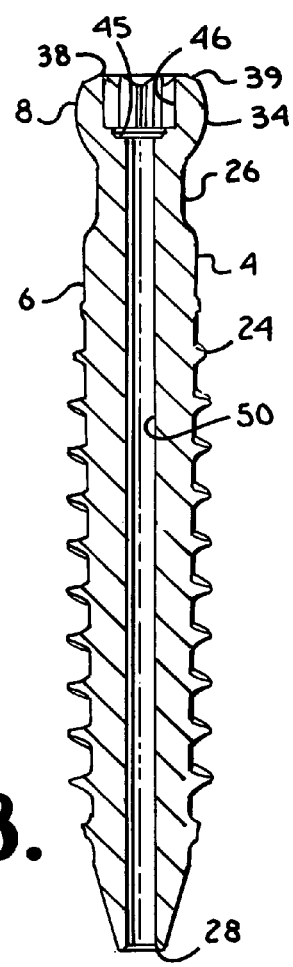
FIG. 3 is reduced cross-sectional view taken along the line 3-3 of FIG. 2.
Figure 4:
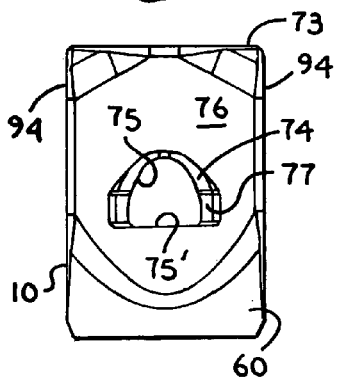
FIG. 4 is an enlarged side elevational view of the receiver of FIG. 1.
Figure 5:
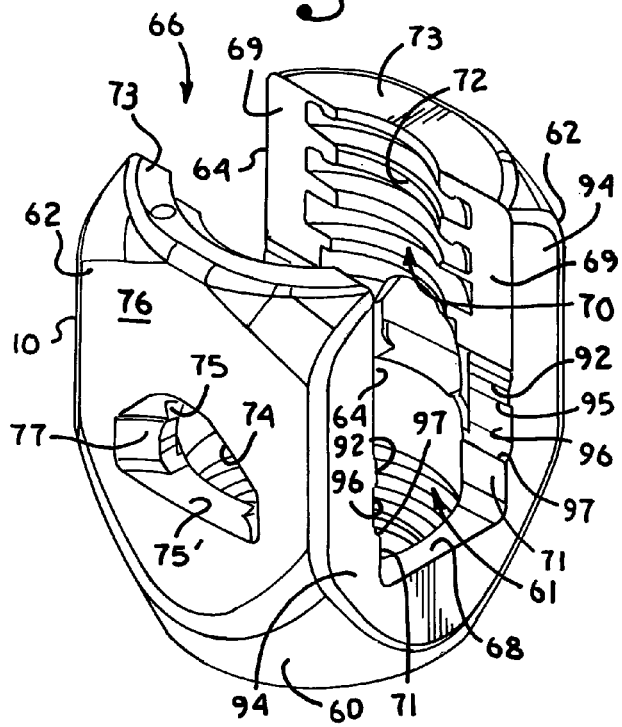
FIG. 5 is an enlarged perspective view of the receiver of FIG. 4.
Figure 6:
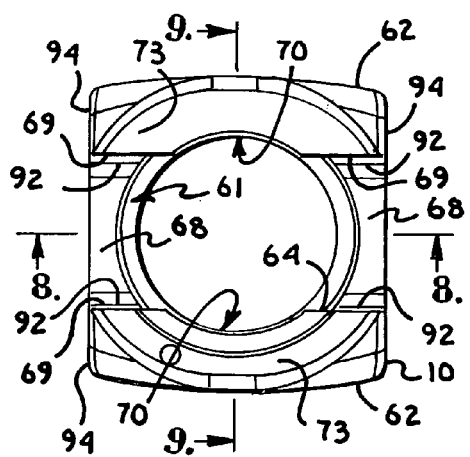
FIG. 6 is an enlarged top plan view of the receiver of FIG. 4.
Figure 7:
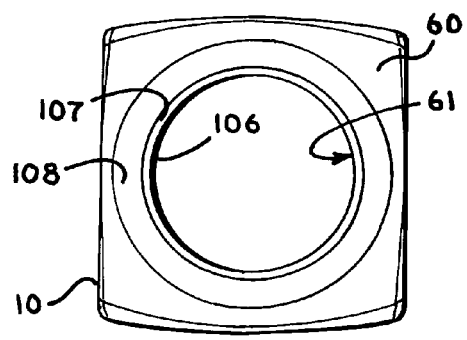
FIG. 7 is an enlarged bottom plan view of the receiver of FIG. 4.
Figure 8:
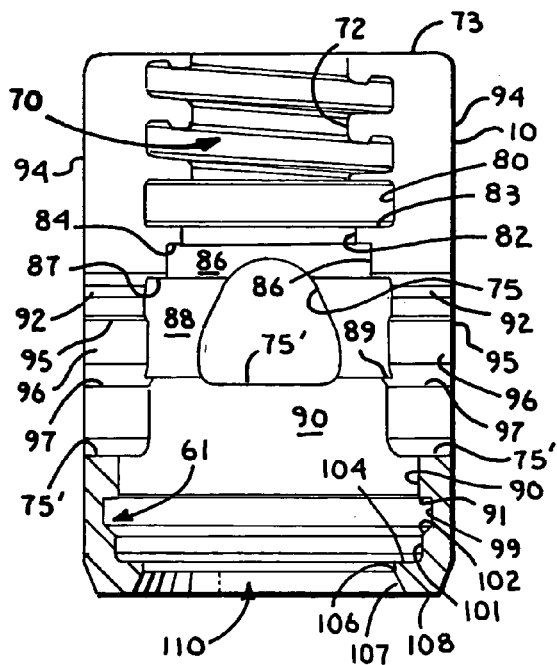
FIG. 8 is an enlarged cross-sectional view taken along the line 8-8 of FIG. 6.
Figure 9:
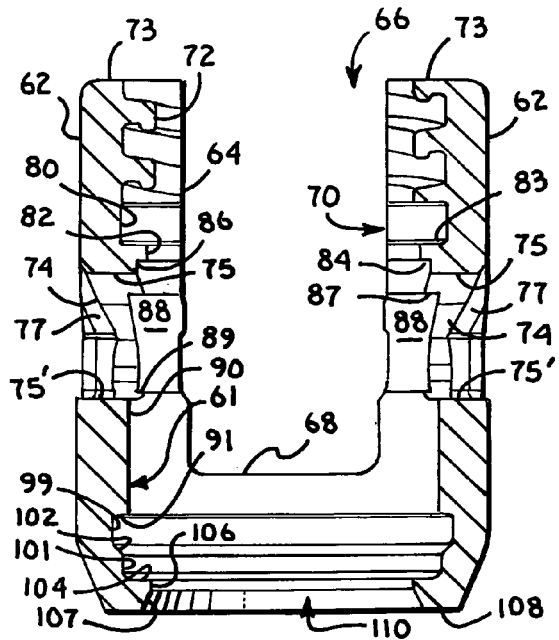
FIG. 9 is an enlarged cross-sectional view taken along the line 9-9 of FIG. 6.
Figure 10:
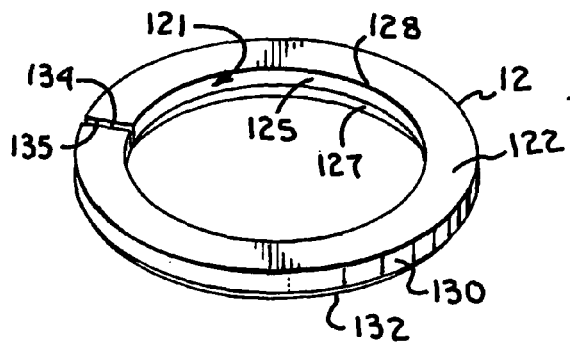
FIG. 10 is an enlarged perspective view of the retainer of FIG. 1.
Figure 11:
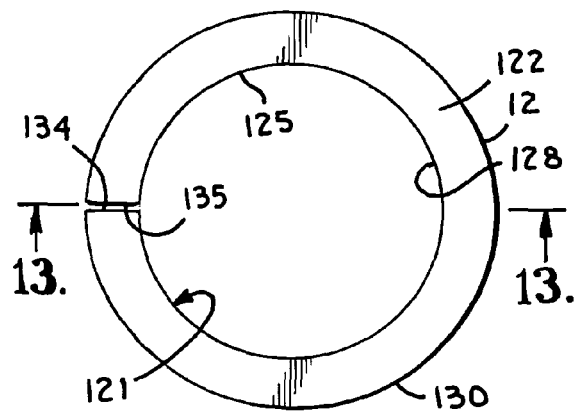
FIG. 11 is a reduced top plan view of the retainer of FIG. 10.
Figure 12:
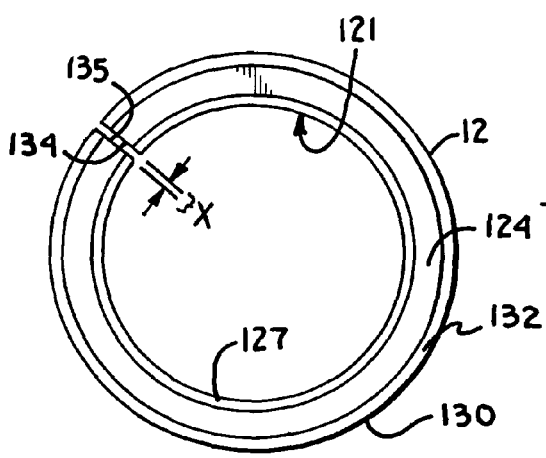
FIG. 12 is a bottom plan view of the retainer of FIG. 10.
Figure 13:
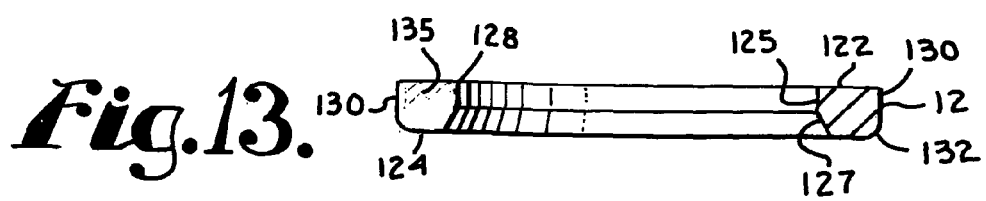
FIG. 13 is an enlarged cross-sectional view taken along the line 13-13 of FIG. 11.
Figure 33:
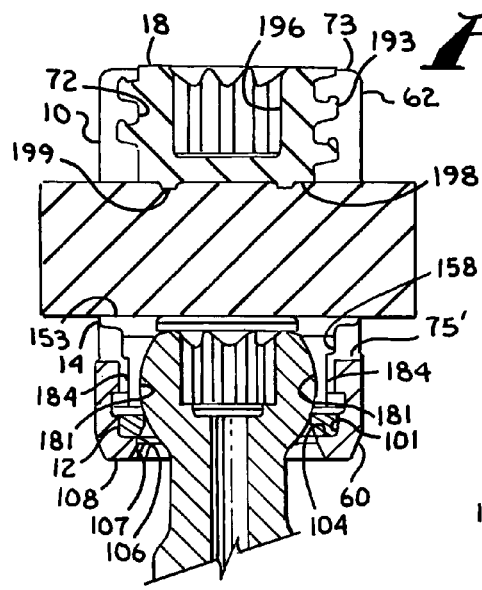
FIG. 33 is an enlarged cross-sectional view taken along the line 33-33 of FIG. 31.
Figure 34:
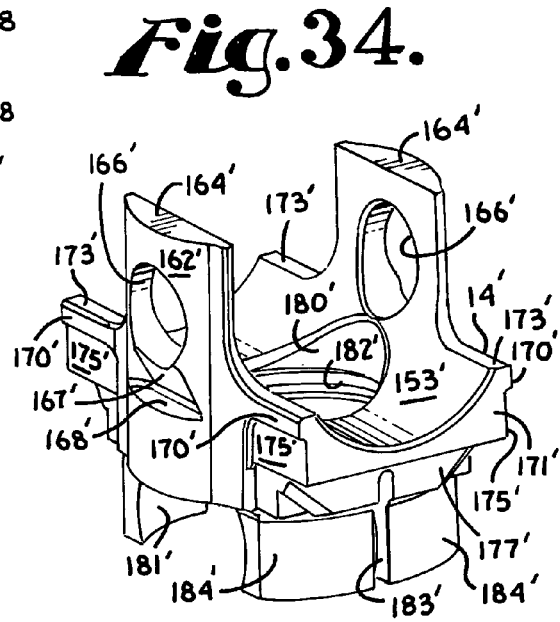
FIG. 34 is an enlarged perspective view of an alternative locking insert for use with the assembly of FIG. 1 in lieu of the insert shown in FIG. 1.
Figure 35:
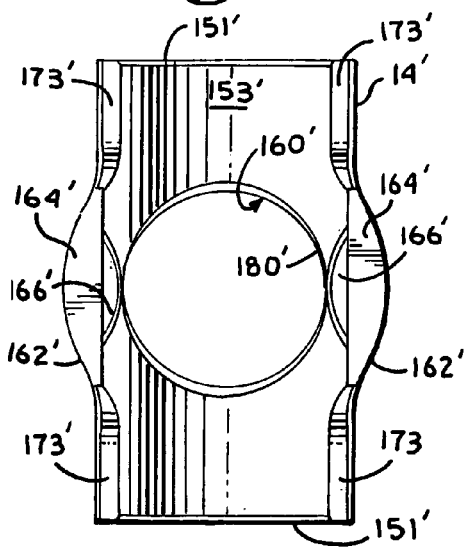
FIG. 35 is a top plan view of the insert of FIG. 34.
Figure 36:
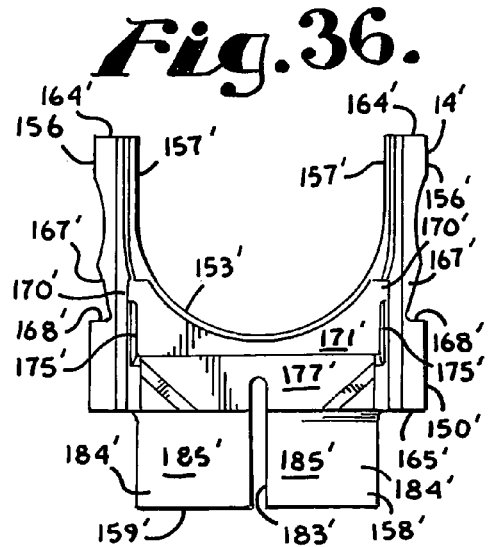
FIG. 36 is a front elevational view of the insert of FIG. 34.

The shank 4, best illustrated in FIGS. 1-3, is elongate, with the shank body 6 having a helically wound bone implantable thread 24 (single or dual lead thread form and different thread types) extending from near a neck 26 located adjacent to the upper portion or head 8, to a tip 28 of the body 6 and extending radially outwardly therefrom. During use, the body 6 utilizing the thread 24 for gripping and advancement is implanted into the vertebra 17 leading with the tip 28 and driven down into the vertebra with an installation or driving tool (not shown), so as to be implanted in the vertebra to a location at or near the neck 26, as more fully described in the paragraphs below. The shank 4 has an elongate axis of rotation generally identified by the reference letter A.

The neck 26 extends axially upward from the shank body 6. The neck 26 may be of the same or is typically of a slightly reduced radius as compared to an adjacent upper end or top 32 of the body 6 where the thread 24 terminates. Further extending axially and outwardly from the neck 26 is the shank upper portion or head 8 that provides a connective or capture apparatus disposed at a distance from the upper end 32 and thus at a distance from the vertebra 17 when the body 6 is implanted in such vertebra.

The shank upper portion 8 is configured for a pivotable connection between the shank 4 and the retainer 12 and receiver 10 prior to fixing of the shank 4 in a desired position with respect to the receiver 10. The shank upper portion 8 has an outer, convex and substantially spherical surface 34 that extends outwardly and upwardly from the neck 26 that in some embodiments terminates at a substantially planar top or rim surface 38. In the illustrated embodiment, a frusto-conical surface 39 extends from the spherical surface 34 to the top surface 38, providing additional clearance during pivoting of the shank with respect to the receiver 10 and the insert 14. The spherical surface 34 has an outer radius configured for temporary frictional, non-floppy, sliding cooperation with panels of the insert 14 having concave or flat surfaces, as well as ultimate frictional engagement with the insert 14 at upper inner stepped surface thereof, as will be discussed more fully in the paragraphs below. The shank top surface 38 is substantially perpendicular to the axis A. The spherical surface 34 shown in the present embodiment is substantially smooth, but in some embodiments may include a roughening or other surface treatment and is sized and shaped for cooperation and ultimate frictional engagement with the compression insert 14 as well as ultimate frictional engagement with the retainer 12. The shank spherical surface 34 is locked into place exclusively by the insert 14 and the retainer 12 and not by inner surfaces defining the receiver cavity.

A counter sunk substantially planar base or stepped seating surface 45 partially defines an internal drive feature or imprint 46. The illustrated internal drive feature 46 is an aperture formed in the top surface 38 and has a star shape designed to receive a tool (not shown) of an Allen wrench type, into the aperture for rotating and driving the bone screw shank 4. It is foreseen that such an internal tool engagement structure may take a variety of tool-engaging forms and may include one or more apertures of various shapes, such as a pair of spaced apart apertures or a multi-lobular or hex-shaped aperture. The seat or base surfaces 45 of the drive feature 46 are disposed substantially perpendicular to the axis A with the drive feature 46 otherwise being coaxial with the axis A. As illustrated in FIGS. 2 and 3, the drive seat 45 may include beveled or stepped surfaces that may further enhance gripping with the driving tool. In operation, a driving tool (not shown) is received in the internal drive feature 46, being seated at the base 45 and engaging the faces of the drive feature 46 for both driving and rotating the shank body 6 into the vertebra 17, either before the shank 4 is attached to the receiver 10 as shown, for example, in FIG. 24, or after the shank 4 is attached to the receiver 10, with the shank body 6 being driven into the vertebra 17 with the driving tool extending into the receiver 10.

The shank 4 shown in the drawings is cannulated, having a small central bore 50 extending an entire length of the shank 4 along the axis A. The bore 50 is defined by an inner cylindrical wall of the shank 4 and has a circular opening at the shank tip 28 and an upper opening communicating with the external drive 46 at the driving seat 45. The bore 50 is coaxial with the threaded body 6 and the upper portion 8. The bore 50 provides a passage through the shank 4 interior for a length of wire (not shown) inserted into the vertebra 17 prior to the insertion of the shank body 6, the wire providing a guide for insertion of the shank body 6 into the vertebra 17. It is foreseen that the shank could be solid and made of different materials, including metal and non-metals.

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate $(Ca_3(PO_4)_2)$, tetra-calcium phosphate $(Ca_4P_2O_9)$, amorphous calcium phosphate and hydroxyapatite $(Ca_{10}(PO_4)_6(OH)_2)$. Coating with hydroxyapatite, for example, is desirable as hydroxyapatite is chemically similar to bone with respect to mineral content and has been identified as being bioactive and thus not only supportive of bone ingrowth, but actively taking part in bone bonding.

With particular reference to FIGS. 1 and 4-9, the receiver 10 has a generally U-shaped appearance with a partially discontinuous, partially faceted and partially curved outer profile and partially cylindrical inner and outer profiles. The receiver 10 has an axis of rotation B that is shown in FIG. 1 as being aligned with and the same as the axis of rotation A of the shank 4, such orientation being desirable, but not required during assembly of the receiver 10 with the shank 4. After the receiver 10 is pivotally attached to the shank 4, either before or after the shank 4 is implanted in a vertebra 17, the axis B is typically disposed at an angle with respect to the axis A, as shown, for example, in FIG. 46 that illustrates the assembly 1 with a manipulation and locking tool.

The receiver 10 includes a curvate lower base portion 60 defining a bore or inner cavity, generally 61, the base 60 being integral with a pair of opposed upstanding arms 62 forming a cradle and defining a channel 64 between the arms 62 with an upper opening, generally 66, and a substantially planar lower channel portion or seat 68, the channel 64 having a width for operably receiving the rod 21 or portion of another longitudinal connector between the arms 62, as well as closely receiving laterally extending portions of the insert 14, the channel 64 communicating with the base cavity 61. Inner opposed substantially planar perimeter arm surfaces 69 partially define the channel 64 and are located on either side of each arm interior substantially cylindrical surfaces generally 70. Lower opposed surface portions 71 of the arm surfaces 69 terminate at the lower seat 68. The arm interior surfaces 70, each include various inner cylindrical profiles, an upper one of which is a partial helically wound guide and advancement structure 72 located adjacent top surfaces 73 of each of the arms 62. In the illustrated embodiment, the guide and advancement structure 72 is a partial helically wound interlocking flangeform configured to mate under rotation with a similar structure on the closure structure 18, as described more fully below. However, it is foreseen that for certain embodiments of the invention, the guide and advancement structure 72 could alternatively be a square-shaped thread, a buttress thread, a reverse angle thread or other thread-like or non-thread-like helically wound discontinuous advancement structures, for operably guiding under rotation and advancing the closure structure 18 downward between the arms 62, as well as eventual torquing when the closure structure 18 abuts against the rod 21 or other longitudinal connecting member. It is foreseen that the arms 62 could have break-off extensions.

An opposed pair of upper rounded off triangular or delta-shaped tool receiving and engaging apertures 74, each having a through bore formed by an upper arched surface 75 and a substantially planar bottom surface 75', are formed on outer surfaces 76 of the arms 62. Each through bore surface 75 and 75' extends through the arm inner surface 70. The apertures 74 with through bore portions 75 and 75' are sized and shaped for receiving locking, unlocking and other manipulation tools and in the illustrated embodiment, receives the retainer ring 12 (as shown in phantom in FIG. 21) during top loading of the retainer 12 into the receiver 10 will be described in greater detail below. Each aperture 74 further includes a sloping tool alignment surface 77 that surrounds the arched bore portion 75 and does not extend completely through the respective arm 62. It is noted that the receiver 10 is an integral structure and devoid of any spring tabs or collet-like structures. As will be discussed in greater detail below, the geometry of the insert 14 that extends outwardly into the receiver channel 64 at the perimeter arms surfaces 69 prohibits the insert 14 from rotating during assembly and thus prohibits any misalignments with the receiver 10 and the rod 21 or other longitudinal connecting member that sometimes occur with other types of compression inserts. The apertures 74 and additional tool receiving apertures or grooves (not shown) may be used for holding the receiver 10 during assembly with the insert 14, the retainer 12 and the shank 4; during the implantation of the shank body 6 into a vertebra when the shank is pre-assembled with the receiver 10; during assembly of the bone anchor assembly 1 with the rod 21 and the closure structure 18; and during lock and release adjustment of some inserts according to the invention with respect to the receiver 10, either into or out of frictional engagement with the inner surfaces of the receiver 10 as will be described in greater detail below. It is foreseen that tool receiving grooves or apertures may be configured in a variety of shapes and sizes and be disposed at other locations on the receiver arms 62.

Returning to the interior surface 70 of the receiver arms 62, located below the guide and advancement structure 72 is a discontinuous cylindrical surface 80 partially defining a run-out feature for the guide and advancement structure 72. The cylindrical surface 80 has a diameter equal to or slightly greater than a greater diameter of the guide and advancement structure 72. Moving downwardly, in a direction toward the base 60, following the cylindrical surface 80 of each arm is a cylindrical surface 82 located below an annular run-out seat or surface 83 that extends inwardly toward the axis B and runs perpendicular or somewhat obliquely towards the axis B. The surface 82 has a diameter smaller than the diameter of the surface 80. The surface 82 is sized and shaped to initially closely receive and frictionally hold a portion of the insert 14 as will be described in greater detail below. Located below the surface 82 is a discontinuous annular surface or narrow ledge 84 that is disposed substantially perpendicular to the axis B. A partially discontinuous cylindrical surface 86 is located on each arm below and adjacent to the ledge surface 84. The surface 86 has a diameter larger than the diameter of the surface 82. A portion of the aperture surface 75 is adjacent to the cylindrical surface 86 at each arm, the surface 86 otherwise terminating at a lower ledge 87. A partially discontinuous cylindrical surface 88 is located on each arm below and adjacent to the lower ledge 87. A diameter of the surface 88 is larger than the diameter of the surface 86. The surface 88 terminates at a lip 89 that extends inwardly toward the receiver axis B. Located below the lip 89 is a partially discontinuous cylindrical surface 90. The surface 90 also partially defines the inner cavity 61 generally below the apertures 74 at the surface 75' and below the channel seat 68. The cylindrical surface 90 has a diameter slightly larger than the diameter of the discontinuous surface 88. The surface 90 terminates at a cavity lower ledge surface 91 that extends outwardly away from the axis B and that may be perpendicular to the axis B, but is illustrated as a frusto-conical surface that extends both downwardly and outwardly away from the axis B. The through bores 75 of the apertures 74 each extend through the arms at the surfaces 86, 88 and 90 with the sloping tool engagement walls 77 extending substantially on either side of each bore surface 75 and formed in the arm outer surfaces 76 at a location primarily opposite the inner surfaces 86 and 88.

With particular reference to FIGS. 1, 5, 6 and 8, returning to the substantially planar peripheral surfaces 69, each arm 62 includes a pair of projecting ridges or stops 92, located on each surface 69, for a total of four stops 92 that are located near the annular surface 87 and extend from front and back surfaces or arm faces 94 to the cylindrical surface 88. The stops 92 of one arm 62 directly face the opposing pair of stops 92 on the other arm 62, each stop 92 projecting outwardly away from the respective planar surface 69. The illustrated stops 92 are elongate and run in a direction perpendicular to the axis B. As will be described in greater detail below, the stops 92 cooperate with surfaces of the insert 14 to retain the insert 14 within the channel 64 of the receiver 10. In the illustrated embodiment, each stop 92 includes a bottom surface or ledge 95 adjacent to a partially planar and partially curved surface 96. A planar portion of the surface 96 located directly beneath the stop 92 is in line with or may be slightly inset from the surface 69. Each set of opposed surfaces 96 curve toward one another and terminate at the respective adjacent lower surface portions 71. An edge 97 defines a juncture of each curved surface 96 and the respective adjacent lower surface portion 71. A first width measured between opposing surface portions 71 is smaller than a second width measured between opposed surfaces 69 located between the stops 92 and arm top surfaces 73, providing opposed planar locking interference fit surfaces for the insert 14' as will be described in greater detail below. The insert 14 is sized and shaped to be closely received but slidable between the surfaces 71.

Returning to FIGS. 8 and 9, the annular or frusto-conical surface 91 partially defines the base cavity 61 and is located below and adjacent to the cylindrical surface 90. Another cylindrical surface 99 is located below and adjacent to the surface 91. The surface 99 also defines a portion of the base cavity 61. The cylindrical surface 99 is oriented substantially parallel to the axis B and is sized and shaped to receive an expanded retainer ring 12. The surfaces 91 and 99 define a circumferential recess that is sized and shaped to receive the retainer 12 as it expands around the shank upper portion 8 as the shank 8 moves upwardly through the receiver base and toward the channel 64 during assembly. It is foreseen that the recess could be tapered or conical in configuration. A cylindrical surface 101 located below the cylindrical surface 99 is sized and shaped to closely receive and surround a lower portion of the retainer 12 when the retainer is in a substantially neutral position as shown in FIG. 37, for example. Thus, the cylindrical surface 101 has a diameter smaller than the diameter of the cylindrical surface 99 that defines the expansion area or expansion chamber for the retainer 12. The surface 101 is joined or connected to the surface 99 by one or more beveled, curved or conical surfaces 102. The surfaces 102 allow for sliding and neutral or nominal positioning of the retainer 12 into the space defined by the surface 101 and ultimate seating of the retainer 12 on a lower substantially horizontal annular surface 104 located below and adjacent to the cylindrical surface 101. The annular surface 104 is disposed substantially perpendicular to the axis B.

Located below and adjacent to the annular seating surface 104 is another substantially cylindrical surface 106 that communicates with a beveled or flared bottom opening surface 107, the surface 107 communicating with an exterior base surface 108 of the base 60, defining a lower opening, generally 110, into the base cavity 61 of the receiver 10.

With particular reference to FIGS. 1 and 10-13, the lower open or split retainer 12, that operates to capture the shank upper portion 8 within the receiver 10, has a central axis that is operationally the same as the axis B associated with the receiver 10 when the shank upper portion 8 and the retainer 12 are installed within the receiver 10. The retainer ring 12 is made from a resilient material, such as a stainless steel or titanium alloy, so that the retainer 12 may be expanded during various steps of assembly as will be described in greater detail below. The retainer 12 has a central channel or hollow through bore, generally 121, that passes entirely through the ring 12 from a top surface 122 to a bottom surface 124 thereof. Surfaces that define the channel or bore 121 include a discontinuous inner cylindrical surface 125 adjacent the top surface 122 and a discontinuous frusto-conical surface 127 adjacent the surface 125, both surfaces coaxial when the retainer 12 is in a neutral non-compressed, non-expanded orientation. An edge 128 is defined by the juncture of the top surface 122 and the cylindrical surface 125. As shown, for example, in FIG. 31, the shank upper portion 8 ultimately frictionally engages the retainer 12 at the edge 128 when the assembly 1 is locked into a final position. The retainer 12 further includes an outer cylindrical surface 130 located adjacent the top surface 122 and an outer beveled or frusto-conical surface 132 adjacent the bottom surface 124. The surface 130 is oriented parallel to the central axis of the retainer 12. In some embodiments of the invention, spaced notches (not shown) may be formed in the cylindrical surface 130 to receive a holding and manipulation tool (not shown). In some embodiments further notches on inner or outer surfaces of the retainer may be made to evenly distribute stress across the entire retainer 12 during expansion thereof.

The resilient retainer 12 further includes first and second end surfaces, 134 and 135 disposed in spaced relation to one another when the retainer is in a neutral non-compressed state. The surface 134 and 135 may also be touching when the retainer is in a neutral state. Both end surfaces 134 and 135 are disposed substantially perpendicular to the top surface 122 and the bottom surface 124. A width X between the surfaces 134 and 135 is very narrow (slit may be made by EDM process) to provide stability to the retainer 12 during operation. Because the retainer 12 is top loadable in a neutral state and the retainer 12 does not need to be compressed to fit within the receiver cavity 61, the width X may be much smaller than might be required for a bottom loaded compressible retainer ring. The gap X functions only in expansion to allow the retainer 12 to expand about the shank upper portion 8. This results in a stronger retainer that provides more surface contact with the shank upper portion 8 upon locking, resulting in a sturdier connection with less likelihood of failure than a retainer ring having a greater gap. Furthermore, because the retainer 12 is only expanded and never compressed inwardly, the retainer 12 does not undergo the mechanical stress that typically is placed on spring ring type retainers known in the prior art that are both compressed inwardly and expanded outwardly during assembly.

It is foreseen that in some embodiments of the invention, the retainer 12 inner surfaces may include a roughening or additional material to increase the friction fit against the shank upper portion 8 prior to lock down by the rod 21 or other longitudinal connecting member. Also, the embodiment shown in FIGS. 10-13 illustrates the surfaces 134 and 135 as substantially parallel to the central axis of the retainer, however, it is foreseen that it may be desirable to orient the surfaces obliquely or at a slight angle.

With particular reference to FIGS. 1 and 14-20, the friction fit compression insert 14 is illustrated that is sized and shaped to be received by and down-loaded into the receiver 10 at the upper opening 66. The compression insert 14 has an operational central axis that is the same as the central axis B of the receiver 10. In operation, the insert advantageously frictionally engages the bone screw shank upper portion 8, allowing for un-locked but non-floppy placement of the angle of the shank 4 with respect to the receiver 10 during surgery prior to locking of the shank with respect to the receiver near the end of the procedure. As will be described in greater detail below with respect to the insert 14' illustrated in FIGS. 34-40, in some embodiments of the invention, the insert that has locked the shank 4 in a desired angular position with respect to the receiver 10, by, for example, compression from the rod 21 and closure top 18, is also forced into an interference fit engagement with the receiver 10 at the pair of opposed receiver planar arm surfaces 71 thereof and thus is capable of retaining the shank 6 in a locked position even if the rod 21 and closure top 18 are removed. Such locked position may also be released by the surgeon if desired. The non-locking insert 14 as well as the locking insert 14' are preferably made from a solid resilient material, such as a stainless steel or titanium alloy, to provide for friction fit panels and also so that arm portions of the insert may be pinched or pressed toward one another in some embodiments, such portions pressing outwardly against the receiver 10 during shipping and early stages of assembly.

The non-locking compression insert 14 includes a body 150 having a partially outer cylindrical surface and an inner U-shaped surface, the insert having opposed ends, generally 151, the insert 14 being sized and shaped to extend completely through the U-shaped channel 64 between the opposed front and back surfaces or faces 94 of the arms 62 so as to cooperate with the receiver arm side surfaces 69, the stops 92, the surfaces 96 and 71 below the stops 92 and the channel seat 68. A U-shaped channel surface or saddle 153 formed in the body 150 also extends between the insert ends 151 and when the insert 14 is assembled with the receiver 10, the saddle 153 substantially aligns with the receiver channel 64. The saddle 153 is formed by the insert body 150 and by two upstanding arms 156 and is sized and shaped to closely receive the rod 21 or other longitudinal connecting member. It is foreseen that an alternative insert embodiment may be configured to include planar holding surfaces that closely hold a square or rectangular bar as well as hold a cylindrical rod-shaped, cord, or sleeved cord longitudinal connecting member.

The insert 14 body 150 is thus integral with the pair of upstanding arms 156 at an upper end thereof and is also integral with a downwardly extending super structure illustrated as an opposed pair of crown collet extensions 158 at a lower end thereof, each super structure extension 158 terminating at a slotted bottom surface 159. A bore, generally 160, is disposed primarily within and through the insert body 150 that runs along the axis B and communicates with the U-shaped channel formed by the saddle 153 and upstanding arms 156 and also runs between the collet extensions 158. The bore 160 is sized and shaped to provide space and clearance for shank driving and other manipulation tools.

The arms 156 that are disposed on either side of the saddle 153 extend upwardly therefrom and are sized and configured for ultimate placement beneath and spaced from the closure top 118 within the receiver cylindrical surfaces 86 and 88. Inner upper arm surfaces 157 extend upwardly and slightly outwardly from the remainder of the U-shaped saddle 153. The arms 156 are also sized and shaped for resilient temporary placement at the receiver cylindrical surface 82. The arms 156 include outer lower convex surfaces 162 that are illustrated as partially cylindrical, outer upper curved surfaces 163 adjacent the surfaces 162, the surfaces 163 being curved and convex and also flaring outwardly from either side of the body 150. The surfaces 163 are adjacent planar top surfaces 164 that are ultimately positioned in spaced relation with the closure top 18, so that the closure top 18 frictionally engages the rod 21 only, pressing the rod 21 downwardly against the insert saddle 153, the shank 4 upper portion 8 then pressing against the retainer 12 to lock the polyaxial mechanism of the bone screw assembly 1 at a desired angle. Each of the top surfaces 164 slopes upwardly and away from the adjacent saddle surface 157.

Each partially cylindrical surface 162 located below the respective flared surface 163 extends from the surface 163 to a partially annular lower or bottom surface 165 of the insert body 150. Each surface 162 is sized and shaped to generally fit within the receiver arms inner arm surfaces, generally 70. It is foreseen that in some embodiments of the invention, the arms 156 may be extended and the top surfaces not sloped and the closure top configured such that the arms and, more specifically, the arm top surfaces ultimately directly engage the closure top 18 for locking of the polyaxial mechanism, for example, when the rod 21 is made from a deformable material. The arm outer surfaces 162 further include notches or grooves formed thereon for receiving and engaging locking tools. Specifically, in the illustrated embodiment, each surface 162 has a v-notch or recess for receiving tooling, the notch defined by an upper sloping surface 167 and intersecting a lower planar surface 168 disposed substantially perpendicular to the central operational axis of the insert 14. The surfaces 167 and 168 cooperate and align with the respective receiver aperture through bore 75, surface, and surface 75' when the insert 14 is captured and operationally positioned within the receiver 10 as will be described in greater detail below. It is also foreseen that the arms 163 can extend upwardly and not be flared or tapered outwardly in some embodiments.

The insert 14 extends from the substantially cylindrical outer arms surfaces 162 equally outwardly to each end 151. Substantially planar outer side surfaces 170 extend from each arm surface 162 to a substantially planar surface 171 disposed perpendicular thereto, the surfaces 171 substantially defining each of the ends 151. Each end surface 171 is adjacent to a lower extension surface 172 that runs substantially parallel to the surface 165 and extends inwardly toward the insert body 150. Adjacent to each side surface 170 is a substantially planar upper or top surface 173 running from one of the arms 156 to each of the end surfaces 171. Each of the surfaces 170 form a narrow outer strip and are adjacent and perpendicular to a lower narrow ledge 174. The ledges 174 run parallel to the upper surfaces 173. An inset planar surface 175 is adjacent to each lower ledge surface 174 and runs parallel to the respective outer planar side surface 170. A width between opposing surfaces 175 is sized such that the surfaces 175 are slidingly received between the opposed receiver lower arm surfaces 71. In other embodiments of the invention, a width between the surfaces 175 may be enlarged such that the surfaces 175 must be forced downwardly between the planar surfaces 71 to provide a locking non-contractile type of interference fit of the insert against the receiver and thus lock the polyaxial mechanism of the bone screw assembly as will be described below with respect to the insert 14'. The surfaces 175 terminate at planar end surfaces 177 and lower extension surfaces 178. A portion of each surface 175 extends all the way to the planar end surface 171.

The insert bore, generally 160, is substantially defined at the body 150 by an inner substantially cylindrical surface 180 that communicates with the saddle 153 and also communicates with a lower concave substantially spherical surface 181 having a radius the same or substantially similar to a radius of the surface 34 of the shank upper portion or head 8. A portion of the surface 181 terminates at the body lower surface 165. The surface 181 also defines inner surfaces of the crown collet extensions 158. Located along the spherical surface 181 between the cylindrical surface 180 and the partially annular lower body surface 165 is a shank gripping surface portion 182. The gripping surface portion 182 includes one or more stepped surfaces or ridges sized and shaped to grip and penetrate into the shank head 8 when the insert 14 is locked against the head surface 34. It is foreseen that the stepped surface portion 182 may include greater or fewer number of stepped surfaces and cover greater or less surface area of the spherical surface 181. It is foreseen that the shank gripping surface portion 182 and also the spherical surface 181 may additionally or alternatively include a roughened or textured surface or surface finish, or may be scored, knurled, or the like, for enhancing frictional engagement with the shank upper portion 8.

The two collet extensions 158 that generally extend in a direction opposite to the two arms 156 and have the discontinuous inner spherical surface 181, also include through slits or slots 183 running substantially vertically from adjacent the shank gripping surface portion 182 through the bottom surfaces 159. The illustrated embodiment includes one slot 183 centrally located in each extension 158. It is foreseen that other embodiments of the invention may include more or fewer slots 183 or no slots. The slots 183 substantially equally partition each of the extensions 158, forming four distinct resilient, partially spherical fingers, tab or panels 196 that extend from the shank gripping portion 182 to the bottom surface 159. In other words, the discontinuous inner spherical surface 181 is further separated into four sections or panels 184, each having the discontinuous partially inner spherical surface 181 and having an outer surface 185 that is substantially cylindrical in form. The panels 184 are sized and shaped to resiliently expand about the spherical surface 34 of the shank upper portion 8 and then snap on and frictionally grip the surface 34. In the illustrated embodiment, the spherical surface 181 is designed such that the gripping tabs or panels 184 have a neutral or non-expanded radius that is the same or slightly smaller than a radius of the shank surface 34 so that when the tabs or panels 184 are gripping the surface 34, the insert 14 collet extension portion 138 is in a neutral or slightly expanded state. In other embodiments, the non-expanded radius is the same or larger than a radius of the shank surface. The contacting surface area between the shank and the insert is sufficient to provide a non-floppy frictional fit in such instances. Furthermore, the shank surface 34 and/or the spherical surface 181 may include a roughened or grooved surface feature to provide for a frictional fit between the shank and the insert. In other embodiments, the resilient panels 184 having a slightly larger pre-assembly radius than the shank surface 34 and may be bent inwardly to result in a tighter frictional fit with the shank surface. When the shank 4 is locked into position by a rod 21 or other connecting member being pressed downwardly on the insert seat 153 by the closure top 18, the insert 14 shank gripping portion 182 that is initially slidable along the shank surface 34 then digs or penetrates into the surface 34 and thus securely fixes the shank upper portion 8 to the insert at the portion 182. It is foreseen that the spherical surfaces 181 could be flat or planar in some embodiments.

Figure 46:
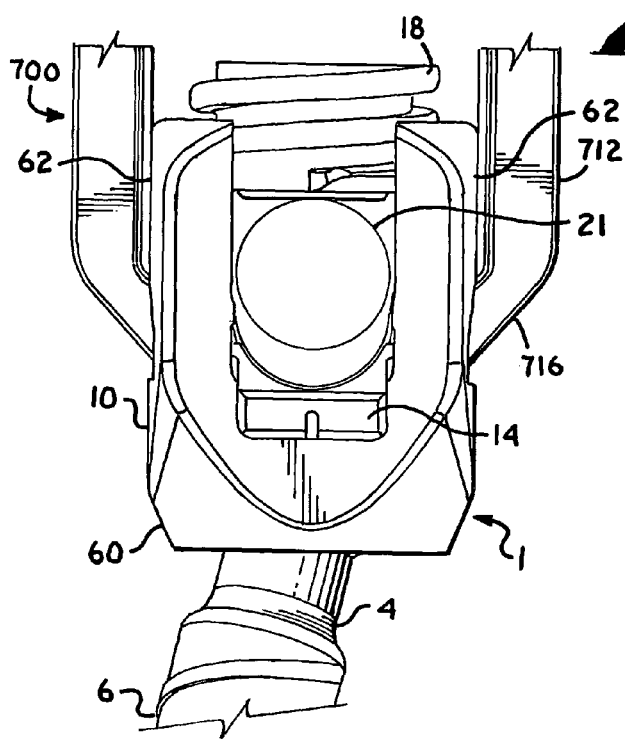
FIG. 46 is an enlarged and partial perspective view of the assembly of FIG. 30, but shown with the shank being at an angle with respect to the receiver and further showing an alternative locking tool for independently locking the shank with respect to the receiver when the closure top and rod are in a loose, unlocked relationship with the receiver as shown.
Figure 48:
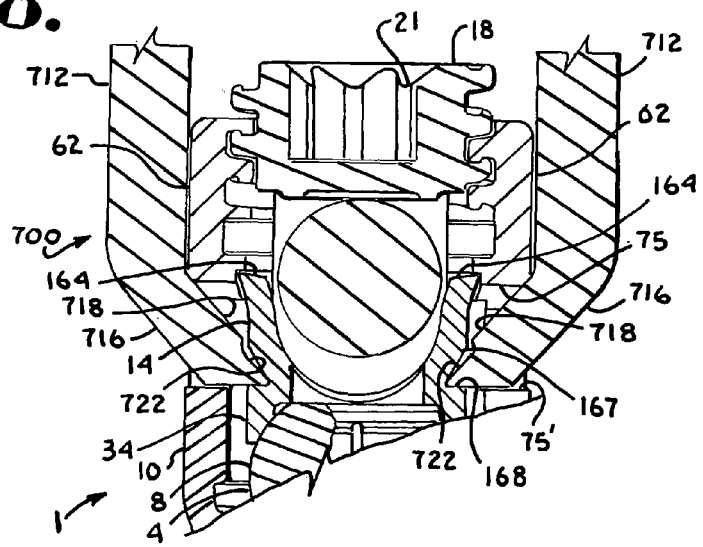
FIG. 48 is an enlarged and partial front elevational view of the assembly and locking tool of FIG. 46 with portions broken away to show the detail thereof.

The bore 160 is sized and shaped to receive the driving tool (not shown) therethrough that engages the shank drive feature 46 when the shank body 6 is driven into bone with the receiver 10 attached. Also, the bore 160 may receive a manipulation tool used for releasing the alternative locking insert 14' from a locked position with the receiver, the tool pressing down on the shank and also gripping the insert 14' at the opposed through bores 166' or with other tool engaging features. A manipulation tool for un-wedging the insert 14' from the receiver 10 may also access the bores 166' from the receiver through bores 74. Referring back to the insert 14, the outer notches defined by the surfaces 167 and 168 may also receive tools extending through receiver through bores 74 to temporarily lock the polyaxial mechanism as shown in FIGS. 46 and 48 and described in greater detail below. The illustrated insert 14 may further include other features, including additional grooves and recesses for manipulating and holding the insert 14 within the receiver 10 and providing adequate clearance between the retainer 12 and the insert 14.

With reference to FIGS. 1 and 30-33, the illustrated elongate rod or longitudinal connecting member 21 (of which only a portion has been shown) can be any of a variety of implants utilized in reconstructive spinal surgery, but is typically a cylindrical, elongate structure having the outer substantially smooth, cylindrical surface 22 of uniform diameter. The rod 21 may be made from a variety of metals, metal alloys, non-metals and deformable and less compressible plastics, including, but not limited to rods made of elastomeric, polyetheretherketone (PEEK) and other types of materials, such as polycarbonate urethanes (PCU) and polyethelenes.

Longitudinal connecting members for use with the assembly 1 may take a variety of shapes, including but not limited to rods or bars of oval, rectangular or other curved or polygonal cross-section. The shape of the insert 14 may be modified so as to closely hold the particular longitudinal connecting member used in the assembly 1. Some embodiments of the assembly 1 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 14 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1, for example. A damping component or bumper may be attached to the longitudinal connecting member at one or both sides of the bone screw assembly 1. A rod or bar (or rod or bar component) of a longitudinal connecting member may be made of a variety of materials ranging from deformable plastics to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 1 and 30-33, the closure structure or closure top 18 shown with the assembly 1 is rotatably received between the spaced arms 62 of the receiver 10. It is noted that the closure 18 top could be a twist-in or slide-in closure structure. The illustrated closure structure 18 is substantially cylindrical and includes an outer helically wound guide and advancement structure 193 in the form of a flange that operably joins with the guide and advancement structure 72 disposed on the arms 62 of the receiver 10. The flange form utilized in accordance with the present invention may take a variety of forms, including those described in Applicant's U.S. Pat. No. 6,726,689, which is incorporated herein by reference. Although it is foreseen that the closure structure guide and advancement structure could alternatively be a buttress thread, a square thread, a reverse angle thread or other thread like or non-thread like helically wound advancement structure, for operably guiding under rotation and advancing the closure structure 18 downward between the arms 62 and having such a nature as to resist splaying of the arms 62 when the closure structure 18 is advanced into the channel 64, the flange form illustrated herein as described more fully in Applicant's U.S. Pat. No. 6,726,689 is preferred as the added strength provided by such flange form beneficially cooperates with and counters any reduction in strength caused by the any reduced profile of the receiver 10 that may more advantageously engage longitudinal connecting member components. The illustrated closure structure 18 also includes a top surface 194 with an internal drive 196 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 196 is used for both rotatable engagement and, if needed, disengagement of the closure 18 from the receiver arms 62. It is also foreseen that the closure structure 18 may alternatively include a break-off head designed to allow such a head to break from a base of the closure at a preselected torque, for example, 70 to 140 inch pounds. Such a closure structure would also include a base having an internal drive to be used for closure removal. A base or bottom surface 198 of the closure is planar and further includes a rim 199 for engagement and penetration into the surface 22 of the rod 21 in certain embodiments of the invention. It is noted that in some embodiments, the closure top bottom surface 198 may include a central point and in other embodiments need not include a point and/or the rim. The closure top 18 may further include a cannulation through bore (not shown) extending along a central axis thereof and through the top and bottom surfaces thereof. Such a through bore provides a passage through the closure 18 interior for a length of wire (not shown) inserted therein to provide a guide for insertion of the closure top into the receiver arms 62.

Figure 41:
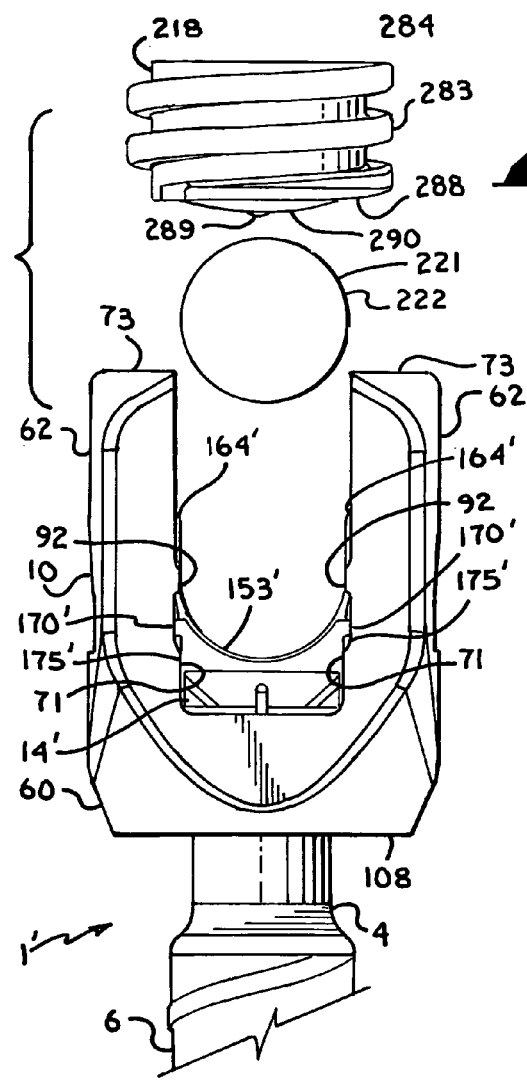
FIG. 41 is an enlarged and partial front elevational view with portions broken away, similar to FIG. 39, showing the shank, retainer, insert and receiver remaining in a locked position after removal of the rod and closure top of FIG. 1 and further showing, in exploded view, an alternative deformable rod and cooperating alternative closure top.
Figure 42:
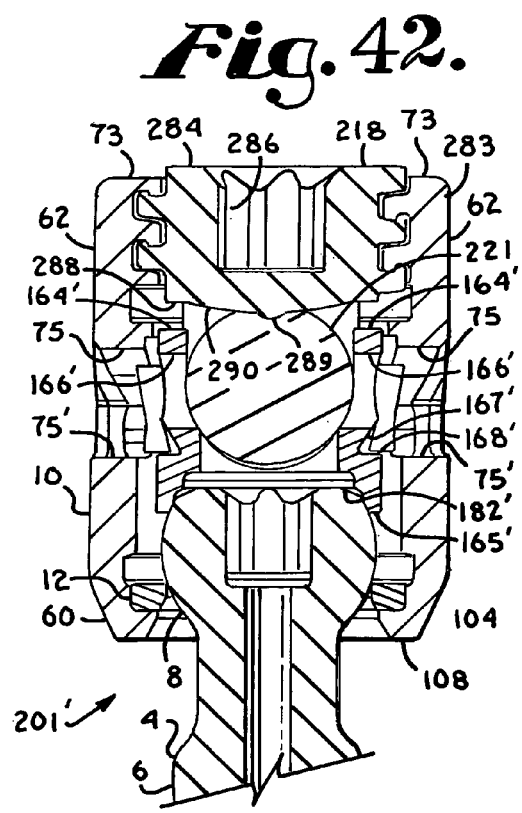
FIG. 42 is a partial front elevational view with portions broken away, similar to FIG. 41, showing the alternative rod and closure top fixed to the remainder of the assembly.

An alternative closure top 218 for use with a deformable rod, such as a PEEK rod 221, is shown in FIGS. 41 and 42. The top 218 is identical to the top 18 with the exception that a point or nub 289 is located on a domed surface 290 in lieu of the rim of the closure top 18. The closure top 218 otherwise includes a guide and advancement structure 283, a top 284, an internal drive 286 and a bottom outer annular surface 288 that same or substantially similar to the respective guide and advancement structure 193, top 194, internal drive 196 and a bottom surface 198 described herein with respect to the closure top 18. In some embodiments, the internal drive 286 is not as large as the drive 196 of the closure top 18, such smaller drive providing for less force being placed on a deformable rod, for example, and not being required when a locking insert, for example, the insert 14' discussed below is utilized in a bone screw assembly of the invention.

Returning to the assembly 1, preferably, the receiver 10, the retainer 12 and the compression insert 14 are assembled at a factory setting that includes tooling for holding, alignment and manipulation of the component pieces. In some circumstances, the shank 4 is also assembled with the receiver 10, the retainer 12 and the compression insert 14 at the factory. In other instances, it is desirable to first implant the shank 4, followed by addition of the pre-assembled receiver, retainer and compression insert at the insertion point. In this way, the surgeon may advantageously and more easily implant and manipulate the shanks 4, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 8 and/or hydroxyapatite on the shank 6), with the receiver, retainer and compression insert. Allowing the surgeon to choose the appropriately sized or treated shank 4 advantageously reduces inventory requirements, thus reducing overall cost and improving logistics and distribution.

Pre-assembly of the receiver 10, retainer 12 and compression insert 14 is shown in FIGS. 21-23. With particular reference to FIG. 21, first the retainer 12 is inserted into the upper receiver opening 66, leading with the cylindrical surface 130 with the top surface 122 and the bottom surface 124 facing opposed arms 62 of the receiver 10 (shown in phantom). The retainer 12 is then lowered in such sideways manner into the channel 64, followed by tilting the retainer 12 at a location in the vicinity of the receiver apertures 74 such that the top surface 122 now faces the receiver opening 66 (also as shown in phantom). Thereafter, the retainer 12 is lowered into the receiver cavity 61 until the bottom surface 124 is seated on the annular lower cavity seating surface 104 as shown in solid lines in FIG. 21.

With reference to FIGS. 22 and 23, the insert 14 is loaded into the receiver 10. The insert 14 is loaded into the receiver through the opening 66 as shown in FIG. 22 with bottom surfaces 159 of the friction fit crown collets 158 facing the receiver cavity 61 and the surfaces 170 and 175 facing the planar arm surfaces 69 that define the channel 64 as the insert 14 is lowered into the channel 64. When the insert 14 is lowered into the receiver, the side surfaces 170 are slidingly received by the opposed receiver inner arm surfaces 69 defining the channel 64 until the insert 14 reaches the stops 92. The insert 14 may be pressed further downwardly until the insert 14 is captured within the receiver 10 as best shown in FIG. 23, with the surfaces 170 being slightly pinched or pressed inwardly toward the receiver axis B to allow the opposed surfaces 170 to engage and then move downwardly past the receiver stops 92, the stops 92 thereafter prohibiting upward movement of the insert 14 out of the receiver channel 64. Specifically, if the insert 14 is moved upwardly toward the opening 66 of the receiver, the insert surfaces 173 abut against bottom surfaces 95 of the stops 92, prohibiting further upward movement of the insert 14 unless a tool is used to pinch the surfaces 170 toward one another while moving the insert 14 upwardly toward the receiver opening 66.

With further reference to FIG. 23 and FIG. 24, the insert 14 does not drop further downwardly toward the retainer 12 at this time because the outer arm surfaces 163 are engaged with and are slightly pressed inwardly by the receiver arm surfaces 82. The insert 14 is thus held in the position shown in FIGS. 23 and 24 by the resilient arms 156 thereof resiliently pressing against the receiver inner cylindrical surfaces 82, which is a desired position for shipping as an assembly along with the separate shank 4. Thus, the receiver 10, retainer 12 and insert 14 combination is now pre-assembled and ready for assembly with the shank 4 either at the factory, by surgery staff prior to implantation, or directly upon an implanted shank 4 as will be described herein.

As illustrated in FIG. 24, the bone screw shank 4 or an entire assembly 1 made up of the assembled shank 4, receiver 10, retainer 12 and compression insert 14, is screwed into a bone, such as the vertebra 17 (shown in phantom), by rotation of the shank 4 using a suitable driving tool (not shown) that operably drives and rotates the shank body 6 by engagement thereof at the internal drive 46. Specifically, the vertebra 17 may be pre-drilled to minimize stressing the bone and have a guide wire (not shown) inserted therein to provide a guide for the placement and angle of the shank 4 with respect to the vertebra. A further tap hole may be made using a tap with the guide wire as a guide. Then, the bone screw shank 4 or the entire assembly 1 is threaded onto the guide wire utilizing the cannulation bore 50 by first threading the wire into the opening at the bottom 28 and then out of the top opening at the drive feature 46. The shank 4 is then driven into the vertebra using the wire as a placement guide. It is foreseen that the shank and other bone screw assembly parts, the rod 21 (also having a central lumen in some embodiments) and the closure top 18 (also with a central bore) can be inserted in a percutaneous or minimally invasive surgical manner, utilizing guide wires and attachable tower tools mating with the receiver. When the shank 4 is driven into the vertebra 17 without the remainder of the assembly 1, the shank 4 may either be driven to a desired final location or may be driven to a location slightly above or proud to provide for ease in assembly with the pre-assembled receiver, compression insert and retainer.

With further reference to FIG. 24, the pre-assembled receiver, insert and retainer are placed above the shank upper portion 8 until the shank upper portion is received within the receiver opening 110. With particular reference to FIGS. 25-29, as the shank upper portion 8 is moved into the interior 61 of the receiver base, the shank upper portion 8 presses upwardly against the retainer 12, moving the retainer 12 into the expansion portion of the receiver cavity 61 partially defined by the annular upper or ledge surface 91 and the cylindrical surface 99. As the portion 8 continues to move upwardly toward the channel 64, the surface 34 forces outward movement of the retainer 12 towards the cylindrical surface 99 as shown in FIG. 25, with upward movement of the retainer 12 being prohibited by the annular surface 91. With reference to FIGS. 26 and 27, the retainer 12 begins to return to its neutral state as the center of the sphere of the head 8 (shown in dotted lines) passes beyond the center of the retainer expansion recess. With further reference to FIGS. 27-28, at this time also, the spherical surface 34 moves into engagement with the discontinuous surface 181 of the insert 14 at the flex tabs or panels 184 of the crown collet extension portions 158. The tabs 184 expand slightly outwardly to receive the surface 34 as best shown in FIG. 28. With further reference to both FIG. 28 and FIG. 29, the spherical surface 34 then enters into full frictional engagement with the panel inner surface 181. At this time, the insert 14 panels and the surface 34 are in a fairly tight friction fit, the surface 34 being pivotable with respect to the insert 14 with some force. Thus, a tight, non-floppy ball and socket joint is now created between the insert 14 and the shank upper portion 8, even before the retainer 12 drops down into a seated position on the receiver annular surface 104.

With reference to FIG. 29, the receiver may then be pulled upwardly or the shank 4 and attached retainer 12 are then moved downwardly into a desired position with the retainer 12 seated on the surface 104. Again, this may be accomplished by either an upward pull on the receiver 10 or, in some cases, by driving the shank 4 further into the vertebra 17. At this time, the insert arms 156 spring outwardly into the receiver surface located beneath the ledge 84 and defined by the discontinuous cylindrical surface 86, making it impossible to move the insert 14 upwardly without special tooling and making it impossible to move the retainer 12 out of the locking portion of the receiver chamber defined by the receiver seat 104 and the cylindrical surface 101. In some embodiments, when the receiver 10 is pre-assembled with the shank 4, the entire assembly 1 may be implanted at this time by inserting the driving tool (not shown) into the receiver and the shank drive 46 and rotating and driving the shank 4 into a desired location of the vertebra 17. With reference to FIGS. 29 and 30 and also, for example, to FIGS. 46 and 48, at this time, the receiver 10 may be articulated to a desired angular position with respect to the shank 4, that will be held, but not locked, by the frictional engagement between the insert 14 flex tabs 184 and the shank upper portion 8.

With reference to FIGS. 30-33, the rod 21 is eventually positioned in an open or percutaneous manner in cooperation with the at least two bone screw assemblies 1. The closure structure 18 is then advanced between the arms 62 of each of the receivers 10. The closure structure 18 is rotated, using a tool engaged with the inner drive 196 until a selected pressure is reached at which point the rod 21 engages the U-shaped seating surface 153 of the compression insert 14, pressing the stepped gripping surfaces 182 against the shank spherical surface 34, the edges of the stepped surfaces 182 penetrating into the spherical surface 34, pressing the shank upper portion 8 into locked frictional engagement with the retainer 12. Specifically, as the closure structure 18 rotates and moves downwardly into the respective receiver 10, the rim 199 engages and penetrates the rod surface 22, the closure structure 18 pressing downwardly against and biasing the rod 21 into compressive engagement with the insert 14 that urges the shank upper portion 8 toward the retainer 12 inner body edge 128 and into locking engagement therewith, the retainer 12 bottom surface 124 frictionally abutting the surface 104 and the outer cylindrical surface 130 expanding outwardly and abutting against the receiver cylindrical surface 101 that defines the receiver locking chamber. For example, about 80 to about 120 inch pounds of torque on the closure top may be applied for fixing the bone screw shank 6 with respect to the receiver 10. If disassembly if the assembly 1 is desired, such is accomplished in reverse order to the procedure described previously herein for assembly.

With reference to FIGS. 34-40, an alternative lock-and-release compression insert 14' is illustrated for use with the shank 4, receiver 10, retainer 12, closure top 18 and rod 21 previously described herein, the resulting assembly identified as an assembly 1' in FIGS. 39-40, for example. The insert 14' may be identical and is illustrated as substantially similar to the insert 14 previously described herein, with the exception that the insert 14' is sized for a locking interference fit with the edges 97 and adjacent planar surfaces 71 of the receiver 10 as will be described in greater detail below. The illustrated insert 14' also differs from the insert 14 in that the insert 14' includes tool receiving apertures 166' and does not have outwardly flared arms for resiliently engaging the receiver 10 during shipping and the early assembly steps.

Thus, the locking insert 14 includes a body 150', a pair of opposed ends 151', a saddle surface 153', a pair of arms 156', a pair of arm upper surfaces 157', a pair of crown collet extensions 158' having bottom surfaces 159', a bore 160', outer cylindrical arm surfaces 162', arm top surfaces 164', body bottom surfaces 165', a pair of v-shaped apertures that include outer sloping surfaces 167', and lower planar surfaces 168', extended portions with outer planar side surfaces 170', planar end surfaces 171', a pair of base extensions 172', upper surfaces 173', narrow lower ledges 174', inset planar side surfaces 175', planar end surfaces 177', bottom surfaces 178', an inner cylindrical surface 180', an inner spherical surface 181' and an inner gripping surface portion 182', slits 183' and flex panels 184' with outer surfaces 185' that are the same or substantially similar in form and function to the respective body 150, pair of opposed ends 151, saddle surface 153, pair of arms 156, pair of arm upper surfaces 157, pair of crown collet extensions 158 having bottom surfaces 159, bore 160, outer cylindrical arm surfaces 162, arm top surfaces 164, body bottom surfaces 165, a pair of v-shaped apertures that include outer sloping surfaces 167, and lower planar surfaces 168, extended portions with outer planar side surfaces 170, planar end surfaces 171, pair of base extensions 172, upper surfaces 173, narrow lower ledges 174, inset planar side surfaces 175, planar end surfaces 177, bottom surfaces 178, inner cylindrical surface 180, inner spherical surface 181, inner gripping surface portion 182, slits 183 and flex panels 184 with outer surfaces 185 previously described herein with respect to the insert 14. As mentioned above, the insert 14' does not include flared upper outer surfaces 163, but rather the cylindrical surfaces 162' extend from the top surfaces 164' to the body lower or bottom surfaces 165'. Furthermore, the top arm surfaces 164' are not sloping, but rather are planar surfaces disposed substantially parallel to the bottom surfaces 165'. The insert 14' includes through holes 166' for receiving manipulation tools, the holes 166' formed on the arm surfaces 162' and located directly above and adjacent to the sloping surfaces 167'.

The insert 14' planar side surfaces 175' are sized and shaped for a locking interference fit with the receiver at a lower portion of the receiver channel 64. In other words, a width measured between surfaces 175' is sized large enough to require that the insert 14' must be forced into the space between the receiver surfaces 71 starting at the edge surfaces 97 by a tool or tools or by the closure top 18 forcing the rod 21 downwardly against the insert 14' with sufficient force to interferingly lock the insert into the receiver between the planar surfaces 71.

With reference to FIGS. 37-40, the insert 14' is assembled with the receiver 10, retainer 12, shank 4, rod 21 and closure top 18, in a manner the same as previously described above with respect to the assembly 1, resulting in an assembly 1', with the exception that the insert 14' must be forced downwardly into a locking interference fit with the receiver 10 when the shank 4 is locked in place, as compared to the easily sliding relationship between the insert 14 and the receiver 10. Also, the receiver arms 156' do not engage the surfaces 82 of the receiver 10. Rather, prior to assembly with the rod 21 and the closure top 18, the compression insert 14' outer surfaces 170' are slidingly received by receiver surfaces 71, but the surfaces 175' are not. The insert 14' is thus prohibited from moving any further downwardly at the edges 97 unless forced downwardly by a locking tool or by the closure top pressing downwardly on the rod that in turn presses downwardly on the insert 14' as shown in FIGS. 38-40. With further reference to FIG. 38, at this time, the receiver 10 may be articulated to a desired angular position with respect to the shank 4, such as that shown in FIGS. 46 and 48, for example, that will be held, but not locked, by the frictional engagement between the insert panels 184' and the shank upper portion 8.

The rod 21 is eventually positioned in an open or percutaneous manner in cooperation with the at least two bone screw assemblies 1'. The closure structure 18 is then inserted into and advanced between the arms 62 of each of the receivers 10. The closure structure 18 is rotated, using a tool engaged with the inner drive 196 until a selected pressure is reached at which point the rod 21 engages the U-shaped seating surface 153' of the compression insert 14', further pressing the insert stepped shank gripping surfaces 182' against the shank spherical surface 34, the edges of the stepped surfaces 182' penetrating into the spherical surface 34, pressing the shank upper portion 8 into locked frictional engagement with the retainer 12. Specifically, as the closure structure 18 rotates and moves downwardly into the respective receiver 10, the rim 199 engages and penetrates the rod surface 22, the closure structure 18 pressing downwardly against and biasing the rod 21 into compressive engagement with the insert 14' that urges the shank upper portion 8 toward the retainer 12 and into locking engagement therewith, the retainer 12 frictionally abutting the surface 104 and expanding outwardly against the cylindrical surface 101. For example, about 80 to about 120 inch pounds of torque on the closure top may be applied for fixing the bone screw shank 6 with respect to the receiver 10. Tightening the helical flange form to 100 inch pounds can create 1000 pounds of force and it has been found that an interference fit is created between the planar surfaces 175' of the insert 14' and the edges 97 and planar surfaces 71 of the receiver at between about 700-900 inch pounds. So, as the closure structure 18 and the rod 21 press the insert 14' downwardly toward the base of the receiver 10, the insert surfaces 175' are forced into the receiver at the edges 97, thus forcing and fixing the insert 14 into frictional interference engagement with the receiver surfaces 71.

With reference to FIG. 41, at this time, the closure top 18 may be loosened or removed and/or the rod 21 may be adjusted and/or removed and the frictional engagement between the insert 14' and the receiver 10 at the insert surfaces 175' will remain locked in place, advantageously maintaining a locked angular position of the shank 4 with respect to the receiver 10.

With further reference to FIGS. 41 and 42, at this time, another rod, such as the deformable rod 221 and cooperating alternative closure top 218 may be loaded onto the already locked-up assembly to result in an alternative assembly 201'. As mentioned above, the closure drive 286 may advantageously be made smaller than the drive of the closure 18, such that the deformable rod 221 is not unduly pressed or deformed during assembly since the polyaxial mechanism is already locked.

With reference to FIGS. 43-45, a two-piece tool 600 is illustrated for releasing the insert 14' from the receiver 10. The tool 600 includes an inner flexible tube-like structure with opposed inwardly facing prongs 612 located on either side of a through-channel 616. The channel 616 may terminate at a location spaced from the prongs 612 or may extend further upwardly through the tool, resulting in a two-piece tool 610. The tool 600 includes an outer, more rigid tubular member 620 having a smaller through channel 622. The member 620 slidingly fits over the tube 610 after the flexible member 610 prongs 612 are flexed outwardly and then fitted over the receiver 10 and then within through bores of the opposed apertures 74 of the receiver 10 and aligned opposed bores 166' located on arms of the insert 14'. In FIG. 43, the tool 600 is shown during the process of unlocking the insert 14' from the receiver 10 with the outer member 620 surrounding the inner member 610 and holding the prongs 612 within the receiver 10 and insert 14' apertures while the tool 600 is pulled upwardly away from the shank 4. It is foreseen that the tool 600 may further include structure for pressing down upon the receiver 10 while the prongs and tubular member are pulled upwardly, such structure may be located within the tool 600 and press down upon the top surfaces 73 of the receiver arms, for example.

Alternatively, another manipulation tool (not shown) may be used that is inserted into the receiver at the opening 66 and into the insert channel formed by the saddle 153', with prongs or extensions thereof extending outwardly into the insert through bores 166'; a piston-like portion of the tool thereafter pushing directly on the shank upper portion 8, thereby pulling the insert 14' away from the receiver surface 90 and thus releasing the polyaxial mechanism. At such time, the shank 4 may be articulated with respect to the receiver 10, and the desired friction fit returns between the insert 14 flex panels and the shank surface 34, so that an adjustable, but non-floppy relationship still exists between the shank 4 and the receiver 10. If further disassembly if the assembly is desired, such is accomplished in reverse order to the procedure described previously herein for the assembly 1.

Figure 47:
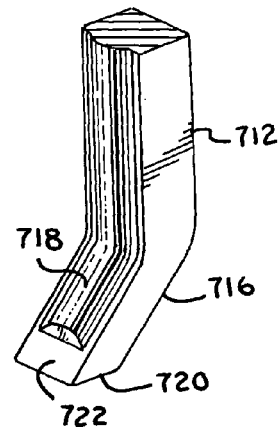
FIG. 47 is a partial perspective view of a portion of the locking tool of FIG. 46.

With reference to FIGS. 46-48, another manipulation tool, generally 700 is illustrated for independently locking an insert 14', or as shown, for temporarily independently locking the non-locking insert 14 to the receiver 10. The tool 700 includes a pair of opposed arms 712, each having an engagement extension 716 positioned at an angle with respect to the respective arm 712 such that when the tool is moved downwardly toward the receiver, one or more inner surfaces 718 of the engagement extension 716 slide along the surfaces 77 of the receiver and surfaces 167 of the insert 14 to engage the insert 14, with a surface 720 pressing downwardly on the insert surfaces 168 to lock the polyaxial mechanism of the assembly 1. As shown in FIG. 48, when the insert 14 is locked against the receiver 10, the tool bottom surfaces 720 do not bottom out on the receiver surfaces 75', but remained spaced therefrom. In the illustrated embodiment, the surface 718 is slightly rounded and each arm extension 716 further includes a planar lower surface 722 that creates an edge with the bottom surface 720 for insertion and gripping of the insert 14 at the juncture of the surface 167 and the surface 168. The tool 700 may include a variety of holding and pushing/pulling mechanisms, such as a pistol grip tool, that may include a ratchet feature, a hinged tool, or, a rotatably threaded device, for example.

Figure 49:
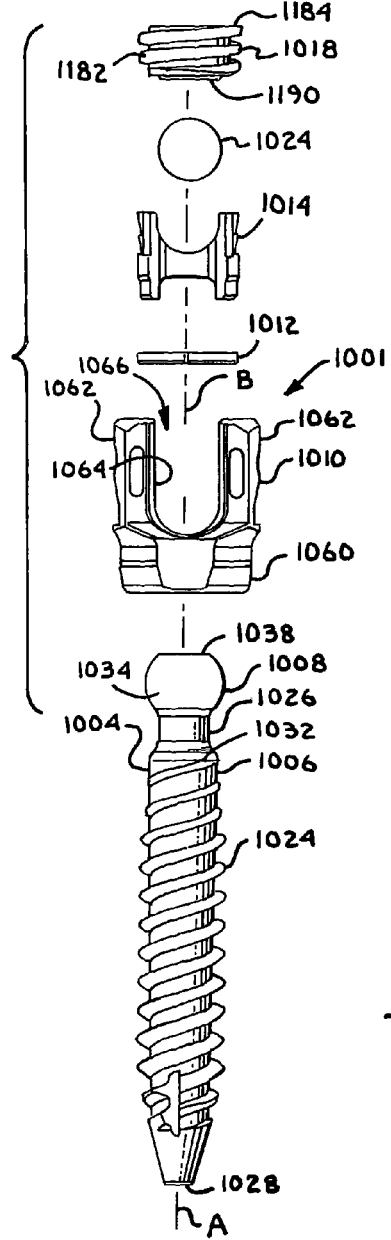
FIG. 49 is an exploded perspective view of another embodiment of a polyaxial bone screw assembly according to the present invention including a shank, a receiver, a retainer in the form of an open ring and a friction fit crown compression insert, further shown with a portion of a longitudinal connecting member in the form of a rod and a closure top.

With reference to FIGS. 49-83 the reference number 1001 generally represents another polyaxial bone screw apparatus or assembly according to the present invention. The assembly 1001 includes a shank 1004, that further includes a body 1006 integral with an upwardly extending upper portion or head-like capture structure 1008; a receiver 1010; a retainer structure illustrated as a resilient open ring 1012, and a friction fit crown collet compression or pressure insert 1014. The receiver 1010, retainer 1012 and compression insert 1014 are initially assembled and may be further assembled with the shank 1004 either prior or subsequent to implantation of the shank body 1006 into a vertebra 1017, as will be described in greater detail below. FIGS. 49 and 82-83 further show a closure structure 1018 for capturing a longitudinal connecting member, for example, a rod 1021 which in turn engages the compression insert 1014 that presses against the shank upper portion 1008 into fixed frictional contact with the retainer 1012, so as to capture, and fix the longitudinal connecting member 1021 within the receiver 1010 and thus fix the member 1021 relative to the vertebra 1017. The illustrated rod 1021 is substantially similar in form and function to the rod 21 previously described herein. It is foreseen that in other embodiments, the rod 1021 may be elastic, deformable and/or of a different cross-sectional geometry. The receiver 1010 and the shank 1004 cooperate in such a manner that the receiver 1010 and the shank 1004 can be secured at any of a plurality of angles, articulations or rotational alignments relative to one another and within a selected range of angles both from side to side and from front to rear, to enable flexible or articulated engagement of the receiver 1010 with the shank 1004 until both are locked or fixed relative to each other near the end of an implantation procedure.

Figure 50:
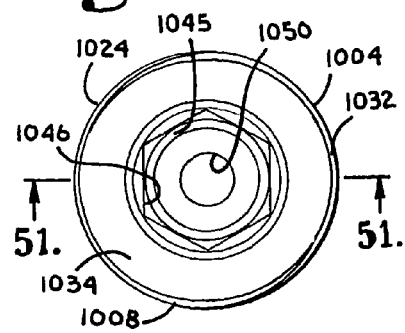
FIG. 50 is an enlarged top plan view of the shank of FIG. 49.
Figure 51:
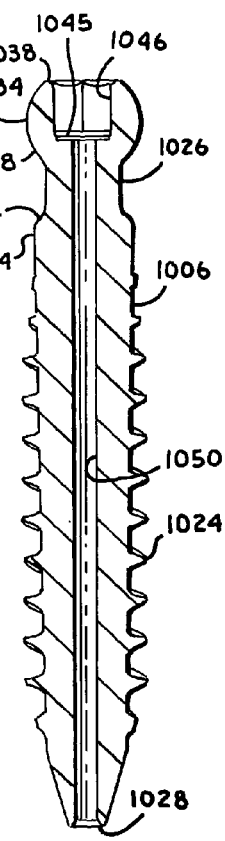
FIG. 51 is reduced cross-sectional view taken along the line 51-51 of FIG. 50.
Figure 63:
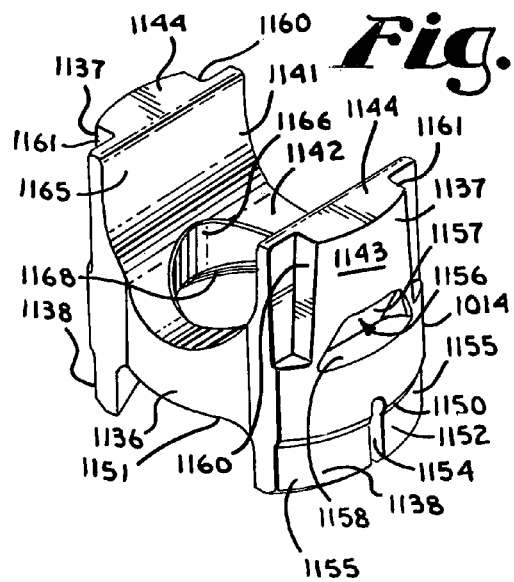
FIG. 63 is an enlarged perspective view of the insert of FIG. 49.
Figure 64:
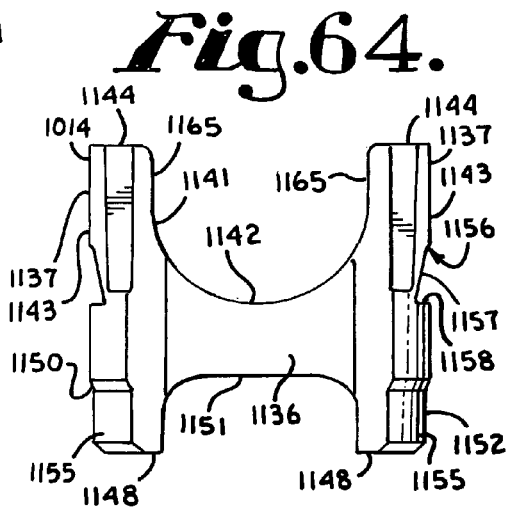
FIG. 64 is a front elevational view of the insert of FIG. 63.
Figure 65:
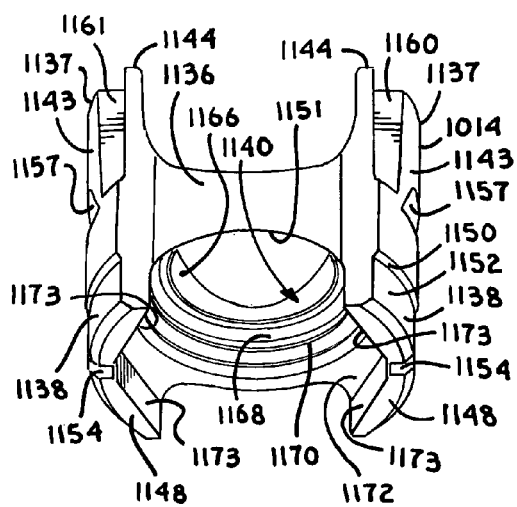
FIG. 65 is another perspective view of the insert of FIG. 63.

The shank 1004, best illustrated in FIGS. 49-51, is elongate, with the shank body 1006 having a helically wound bone implantable thread 1024 (single or dual lead thread form) extending from near a neck 1026 located adjacent to the upper portion or head 1008, to a tip 1028 of the body 1006 and extending radially outwardly therefrom. During use, the body 1006 utilizing the thread 1024 for gripping and advancement is implanted into the vertebra 1017 leading with the tip 1028 and driven down into the vertebra with an installation or driving tool (not shown), so as to be implanted in the vertebra to a location at or near the neck 1026. The shank 1004 has an elongate axis of rotation generally identified by the reference letter A.

The neck 1026 extends axially upward from the shank body 1006. The neck 1026 may be of the same or is typically of a slightly reduced radius as compared to an adjacent upper end or top 1032 of the body 1006 where the thread 1024 terminates. Further extending axially and outwardly from the neck 1026 is the shank upper portion or head 1008 that provides a connective or capture apparatus disposed at a distance from the upper end 1032 and thus at a distance from the vertebra 1017 when the body 1006 is implanted in such vertebra.

The shank upper portion 1008 is configured for a pivotable connection between the shank 1004 and the retainer 1012 and receiver 1010 prior to fixing of the shank 1004 in a desired position with respect to the receiver 1010. The shank upper portion 1008 has an outer, convex and substantially spherical surface 1034 that extends outwardly and upwardly from the neck 1026 and terminates at a substantially planar top or rim surface 1038. The spherical surface 1034 has an outer radius configured for frictional, non-floppy, sliding cooperation with a discontinuous concave surface of the compression insert 1014, as well as ultimate frictional engagement and penetration by a stepped, gripping portion of the insert 1014. The top surface 1038 is substantially perpendicular to the axis A. The spherical surface 1034 shown in the present embodiment is substantially smooth, but in some embodiments may include a roughening or other surface treatment and is sized and shaped for cooperation and ultimate frictional engagement with the compression insert 1014 as well as ultimate frictional engagement with the retainer 1012. The shank spherical surface 1034 is locked into place exclusively by the insert 1014 and the retainer 1012 and not by inner surfaces defining the receiver cavity.

A counter sunk substantially planar base or stepped seating surface 1045 partially defines an internal drive feature or imprint 1046. The illustrated internal drive feature 1046 is an aperture formed in the top surface 1038 and has a hex shape designed to receive a hex tool (not shown) of an Allen wrench type, into the aperture for rotating and driving the bone screw shank 1004. It is foreseen that such an internal tool engagement structure may take a variety of tool-engaging forms and may include one or more apertures of various shapes, such as a pair of spaced apart apertures or a multi-lobular or star-shaped aperture, such as those sold under the trademark TORX, or the like. The seat or base surfaces 1045 of the drive feature 1046 are disposed substantially perpendicular to the axis A with the drive feature 1046 otherwise being coaxial with the axis A. As illustrated in FIGS. 50 and 51, the drive seat 1045 may include beveled or stepped surfaces that may further enhance gripping with the driving tool. In operation, a driving tool (not shown) is received in the internal drive feature 1046, being seated at the base 1045 and engaging the six faces of the drive feature 1046 for both driving and rotating the shank body 1006 into the vertebra 1017, either before the shank 1004 is attached to the receiver 1010 or after the shank 1004 is attached to the receiver 1010, with the shank body 1006 being driven into the vertebra 1017 with the driving tool extending into the receiver 1010.

The shank 1004 shown in the drawings is cannulated, having a small central bore 1050 extending an entire length of the shank 1004 along the axis A. The bore 1050 is defined by an inner cylindrical wall of the shank 1004 and has a circular opening at the shank tip 1028 and an upper opening communicating with the external drive 1046 at the driving seat 1045. The bore 1050 is coaxial with the threaded body 1006 and the upper portion 1008. The bore 1050 provides a passage through the shank 1004 interior for a length of wire (not shown) inserted into the vertebra 1017 prior to the insertion of the shank body 1006, the wire providing a guide for insertion of the shank body 1006 into the vertebra 1017. The shank body 1006 may be treated or coated as previously described herein with respect to the shank body 6 of the assembly 1.

Figure 76:
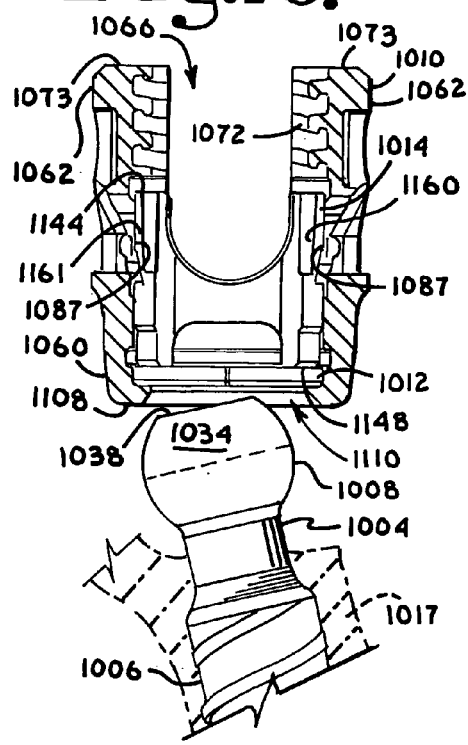
FIG. 76 is a reduced front elevational view with portions broken away, similar to FIG. 73 and with the crimping of FIGS. 74 and 75 and further showing an alternative assembly stage with the shank of FIG. 49 shown in partial front elevation in which the shank is first implanted in a vertebra, shown in phantom, followed by assembly with the receiver, retainer and insert.

With particular reference to FIGS. 49 and 52-57, the receiver 1010 has a generally U-shaped appearance with partially discontinuous and partially cylindrical inner and outer profiles. The receiver 1010 has an axis of rotation B that is shown in FIG. 49 as being aligned with and the same as the axis of rotation A of the shank 1004, such orientation being desirable, but not required during assembly of the receiver 1010 with the shank 1004 (see, e.g., FIG. 76 showing the receiver 1010 being "popped on" to a shank 1004 that is implanted in a vertebra 1017 and disposed at an angle with respect to the receiver). After the receiver 1010 is pivotally attached to the shank 1004, either before or after the shank 1004 is implanted in a vertebra 1017, the axis B is typically disposed at an angle with respect to the axis A, as shown, for example, in FIG. 96.

The receiver 1010 includes a substantially cylindrical base 1060 defining a bore or inner cavity, generally 1061, the base 1060 being integral with a pair of opposed upstanding arms 1062 forming a cradle and defining a channel 1064 between the arms 1062 with an upper opening, generally 1066, and a U-shaped lower channel portion or seat 1068, the channel 1064 having a width for operably snugly receiving the rod 1021 or portion of another longitudinal connector, such as a sleeve of a tensioned cord connector or other soft or dynamic connector between the arms 1062, the channel 1064 communicating with the base cavity 1061. Outer front and rear opposed substantially planar arm surfaces 1069 partially define the channel 1064 directly above the seat 1068, the surfaces 1069 advantageously reduce the run on the rod (i.e., provide a more narrow receiver portion that in turn provides more space and thus more access between bone anchors along the rod or other connecting member) and provide the planar surface 1069 for flush or close contact with other connecting member components in certain embodiments, such as sleeves, bumpers or spacers that cooperate with rods or cord-type connecting members.

Each of the arms 1062 has an interior surface, generally 1070, that includes various inner cylindrical profiles, an upper one of which is a partial helically wound guide and advancement structure 1072 located adjacent top surfaces 1073 of each of the arms 1062. In the illustrated embodiment, the guide and advancement structure 1072 is a partial helically wound interlocking flangeform configured to mate under rotation with a similar structure on the closure structure 1018, as described more fully below. However, it is foreseen that for certain embodiments of the invention, the guide and advancement structure 1072 could alternatively be a square-shaped thread, a buttress thread, a reverse angle thread or other thread-like or non-thread-like helically wound discontinuous advancement structures, for operably guiding under rotation and advancing the closure structure 1018 downward between the arms 1062, as well as eventual torquing when the closure structure 1018 abuts against the rod 1021 or other longitudinal connecting member. It is foreseen that the arms could have break-off extensions.

An opposed pair of upper rounded off triangular or delta-shaped tool receiving and engaging apertures, generally 1074, each having a through bore formed by an upper arched surface 1075 and a substantially planar bottom surface 1075', are formed on outer surfaces 1076 of the arms 1062. Each through bore surface 1075 and 1075' extends through the arm inner surface 1070. The apertures 1074 with through bore portions 1075 and 1075' are sized and shaped for receiving locking, unlocking and other manipulation tools and may aid in receiving and downloading the retainer ring 1012 during top loading of the retainer 1012 into the receiver 1010. Each aperture 1074 further includes a sloping tool alignment surface 1077 that surrounds the arched bore portion 1075 and does not extend completely through the respective arm 1062. In the present embodiment, part of the receiver defining the surface 1077 located along the arched aperture portion is crimped into the insert 1014 during assembly thereof with the receiver 1010 as will be described in greater detail below. In other embodiments of the invention, other walls or surfaces defining the aperture 1074 or other material defining other apertures or grooves may be inwardly crimped. It is noted that the illustrated receiver 1010 is an integral structure and devoid of any spring tabs or collet-like structures. Alternatively, in some embodiments, spring tabs or other movable structure may be included on the receiver 1010 or the insert 1014 for retaining the insert 1014 in a desired position, with regard to rotation and axial movement (along the axis A) with respect to the receiver 1010. Preferably the insert and/or receiver are configured with structure for blocking rotation of the insert with respect to the receiver, but allowing some up and down movement of the insert with respect to the receiver during the assembly and implant procedure.

Located directly centrally above each delta shaped aperture 1074 is a cylindrical depression or aperture 1078, also formed in each arm surface 1076, but not extending through the inner surface 1070. Two additional pair of tool receiving and engaging apertures 1079 are also formed in the front and rear surfaces 1069 of the receiver arms 1062. Transition base surfaces 1080 span between the planar surfaces 1069 at the U-shaped seat 1068 and the cylindrical base 1060, the surfaces 1080 sloping downwardly toward the base 1060 at an angle with respect to the axis B. Some or all of the apertures 1074, 1078 and 1079 may be used for holding the receiver 1010 during assembly with the insert 1014, the retainer 1012 and the shank 1004; during the implantation of the shank body 1006 into a vertebra when the shank is pre-assembled with the receiver 1010; during assembly of the bone anchor assembly 1001 with the rod 1021 and the closure structure 1018; and during lock and release adjustment of the some inserts of the invention with respect to the receiver 1010, either into or out of frictional engagement with the inner surfaces of the receiver 1010 as will be described in greater detail below. It is foreseen that tool receiving grooves, depressions or apertures may be configured in a variety of shapes and sizes and be disposed at other locations on the receiver arms 1062.

Returning to the interior surface 1070 of the receiver arms 1062, located below the guide and advancement structure 1072 is a discontinuous cylindrical surface 1082 partially defining a run-out feature for the guide and advancement structure 1072. The cylindrical surface 1082 has a diameter equal to or slightly greater than a greater diameter of the guide and advancement structure 1072. Moving downwardly, in a direction toward the base 1060, adjacent the cylindrical surface 1082 of each arm is a run-out seat or surface 1084 that extends inwardly toward the axis B and slopes toward the axis B. Adjacent to and located below the surface 1084 is another cylindrical surface 1086 having a diameter smaller than the diameter of the surface 1082. The through bore surfaces 1075 and 1075' extend through the arms primarily at the surfaces 1086, with an upper portion of each arch 1075 extending through one of the surfaces 1082. Located near each aperture surface 1075 is an inner surface portion 1087 that engages the insert 1014 when the thin wall at the surface 1077 is crimped toward the insert 1014 during assembly of such insert in the receiver 1010 as will be described in greater detail below. A continuous annular surface 1088 is located below and adjacent to the cylindrical surface 1086. The otherwise discontinuous cylindrical surface 1086 that partially forms the receiver arms 1062 is also continuous at and near the interface between the surface 1086 and the annular surface 1088, forming an upper portion of the receiver cavity 1061. The surface 1088 is disposed substantially perpendicular or slopes inwardly toward the axis B. A continuous inner cylindrical surface 1090 is adjacent the annular surface 1088 and extends downwardly into the receiver base 1060. The surface 1090 is disposed parallel to the receiver axis B. The surface 1090 has a diameter slightly smaller than the diameter of the surface 1086. The cylindrical surfaces 1086 and 1090 are sized to receive portions of the insert 1014, and as will be described in greater detail below, in some embodiments provide a locking interference fit with a cylindrical portion of a locking insert.

Now, with respect to the base 1060 and more specifically, the base cavity 1061, a lower portion of the surface 1090 that extends into the base and partially defines the base cavity 1061 terminates at an annular surface or ledge 1095. The ledge 1095 extends outwardly away from the axis B and is substantially perpendicular thereto.

Extending downwardly from the ledge 1095 is a cylindrical surface 1099 that partially defines the base cavity 1061 and in particular, defines an expansion chamber for the retainer 1012. The cylindrical surface 1099 is oriented substantially parallel to the axis B and is sized and shaped to receive an expanded retainer 1012. The surfaces 1095 and 1099 define a circumferential recess that is sized and shaped to receive the retainer 1012 as it expands around the shank upper portion 1008 as the shank 1004 moves upwardly toward the channel 1064 during assembly, as well as form a stop or restriction to prevent the expanded retainer 1012 from moving upwardly with the shank portion 1008, the surface 1095 preventing the retainer 1012 from passing upwardly out of the cavity 1061 whether the retainer 1012 is in a partially or fully expanded position or state. A cylindrical surface 1101 located below the cylindrical surface 1099 is sized and shaped to closely receive the retainer 1012 when the retainer is in a neutral position as shown in FIG. 71, for example. Thus, the cylindrical surface 1101 has a diameter smaller than the diameter of the cylindrical surface 1099 that defines the expansion area for the retainer 1012. The surface 1101 is joined or connected to the surface 1099 by one or more beveled, curved or conical surfaces 1102. The surfaces 1102 allow for sliding gradual movement of the retainer 1012 into the space or locking chamber defined by the surface 1101 and ultimate seating of the retainer 1012 on a lower annular surface 1104 located below and adjacent to the cylindrical surface 1101.

Located below and adjacent to the annular seating surface 1104 is another substantially cylindrical surface 1106 that communicates with a beveled or flared bottom opening surface 1107, the surface 1107 communicating with an exterior base surface 1108 of the base 1060, defining a lower opening, generally 1110, into the base cavity 1061 of the receiver 1010.

With particular reference to FIGS. 49 and 58-62, the lower open or split retainer 1012, that operates to capture the shank upper portion 1008 within the receiver 1010, has a central axis that is operationally the same as the axis B associated with the receiver 1010 when the shank upper portion 1008 and the retainer 1012 are installed within the receiver 1010. The retainer ring 1012 is made from a resilient material, such as a stainless steel or titanium alloy, so that the retainer 1012 may be expanded during various steps of assembly as will be described in greater detail below. The retainer 1012 has a central channel or hollow through bore, generally 1121, that passes entirely through the ring 1012 from a top surface 1122 to a bottom surface 1124 thereof. Surfaces that define the channel or bore 1121 include a discontinuous inner cylindrical surface 1125 adjacent the top surface 1122 and a discontinuous frusto-conical surface 1127 adjacent the surface 1125, both surfaces coaxial when the retainer 1012 is in a neutral, non-expanded orientation. An edge 1128 is defined by the juncture of the top surface 1122 and the cylindrical surface 1125. The edge 1128 may include a chamfer or bevel. As shown, for example, in FIG. 82, the shank upper portion 1008 ultimately frictionally engages the retainer 1012 at the edge 1128 when the assembly 1001 is locked into a final position. The retainer 1012 further includes an outer cylindrical surface 1130 located adjacent the top surface 1122 and an outer beveled or frusto-conical surface 1132 adjacent the bottom surface 1124. The surface 1130 is oriented parallel to the central axis of the retainer 1012. In some embodiments of the invention, spaced notches (not shown) may be formed in the cylindrical surface 1130 to receive a holding and manipulation tool (not shown). In some embodiments further notches on inner or outer surfaces of the retainer may be made to evenly distribute stress across the entire retainer 1012 during expansion thereof.

The resilient retainer 1012 further includes first and second end surfaces, 1134 and 1135 disposed in spaced relation to one another when the retainer is in a neutral non-compressed state. The surface 1134 and 1135 may also be touching when the retainer is in a neutral state. Both end surfaces 1134 and 1135 are disposed substantially perpendicular to the top surface 1122 and the bottom surface 1124. A width X between the surfaces 1134 and 1135 is very narrow (slit may be made by EDM process) to provide stability to the retainer 1012 during operation. Because the retainer 1012 is top loadable in a neutral state and the retainer 1012 does not need to be compressed to fit within the receiver cavity 1061, the width X may be much smaller than might be required for a bottom loaded compressible retainer ring. The gap X functions only in expansion to allow the retainer 1012 to expand about the shank upper portion 1008. This results in a stronger retainer that provides more surface contact with the shank upper portion 1008 upon locking, resulting in a sturdier connection with less likelihood of failure than a retainer ring having a greater gap. Furthermore, because the retainer 1012 is only expanded and never compressed inwardly, the retainer 1012 does not undergo the mechanical stress that typically is placed on spring ring type retainers known in the prior art that are both compressed inwardly and expanded outwardly during assembly.

It is foreseen that in some embodiments of the invention, the retainer 1012 inner surfaces may include a roughening or additional material to increase the friction fit against the shank upper portion 1008 prior to lock down by the rod 1021 or other longitudinal connecting member. Also, the embodiment shown in FIGS. 58-62 illustrates the surfaces 1134 and 1135 as substantially parallel to the central axis of the retainer, however, it is foreseen that it may be desirable to orient the surfaces obliquely or at a slight angle.

With particular reference to FIGS. 49 and 63-70, the friction fit, crown compression insert 1014 is illustrated that is sized and shaped to be received by and down-loaded into the receiver 1010 at the upper opening 1066. The compression insert 1014 has an operational central axis that is the same as the central axis B of the receiver 1010. In operation, the insert advantageously frictionally engages the bone screw shank upper portion 1008, allowing for un-locked but non-floppy placement of the angle of the shank 1004 with respect to the receiver 1010 during surgery prior to locking of the shank with respect to the receiver near the end of the procedure. As will be described in greater detail below with respect to the insert 1014' illustrated in FIGS. 84-92, in some embodiments of the invention, the insert that has locked the shank 1004 in a desired angular position with respect to the receiver 1010, by, for example, compression from the rod 1021 and closure top 1018, is also forced into an interference fit engagement with the receiver 1010 at the inner cylindrical surface 1090 and thus is capable of retaining the shank 1006 in a locked position even if the rod 1021 and closure top 1018 are removed. Such locked position may also be released by the surgeon if desired. The non-locking insert 1014 as well as the locking insert 1014' are preferably made from a solid resilient material, such as a stainless steel or titanium alloy, so that portions of the insert may be snapped or popped onto the shank upper portion 1008 as well as pinched or pressed against and un-wedged from the receiver 1010 with a release tool.

The non-locking crown collet compression insert 1014 includes a substantially cylindrical body 1136 integral with a pair of upstanding arms 1137 at an upper end thereof and integral with downwardly extending resilient superstructure in the form of an opposed pair of crown Collet extensions 1138 at a lower end thereof. A bore, generally 1140, is disposed primarily within and through the body 1136 and communicates with a generally U-shaped through channel formed by a saddle 1141 that is partially defined by the upstanding arms 1137 and partially by the body 1136. The saddle 1141 is sized and shaped to closely, snugly engage the cylindrical rod 1021 and includes a curved lower seat 1142. It is foreseen that an alternative embodiment may be configured to include planar holding surfaces that closely hold a square or rectangular bar as well as hold a cylindrical rod-shaped, cord, or sleeved cord longitudinal connecting member. The arms 1137 disposed on either side of the saddle 1141 extend upwardly from the body 1136. The arms 1137 are sized and configured for ultimate placement at or near the cylindrical run-out surface 1082 and inner surfaces 1084 and 1086 located below the receiver guide and advancement structure 1072. It is foreseen that in some embodiments of the invention, the insert arms 1137 may be extended and the closure top configured such the arms ultimately directly engage the closure top 1018 for locking of the polyaxial mechanism, for example, when the rod 1021 is made from a deformable material. In such embodiments, the insert 1014 would include a rotation blocking structure or feature on an outer surface thereof that abuts against cooperating structure located on an inner wall of the receiver 1010, preventing rotation of the insert with respect to the receiver when the closure top is rotated into engagement with the insert. In the present embodiment, the arms 137 include outer surfaces 1143 that are illustrated as partially cylindrical and run from substantially planar top surfaces 1144 to near bottom surfaces 1148 of the collet extensions 1138, the top surfaces 1144 ultimately being positioned in spaced relation with the closure top 1018, so that the closure top 1018 frictionally engages the rod 1021 only, pressing the rod 1021 downwardly against the seating surface 1142, the insert 1014 in turn pressing against the shank 1004 upper portion 1008 that presses against the retainer 1012 to lock the polyaxial mechanism of the bone screw assembly 1001 at a desired angle. Specifically, the illustrated partially cylindrical surfaces 1143 each extend from one of the arm top surfaces 1144 to a rim or ledge 1150 spaced from the bottom surfaces 1148 of the collet extensions 1138. Each rim or ledge 1150 is positioned near an annular lower surface 1151 of the insert body 1136. Located between each rim 1150 and each extension bottom surface 1148 is a discontinuous outer cylindrical surface 1152 partially defining each collet extension 1138 and having an outer diameter smaller than a diameter of the arm cylindrical surfaces 1143. A through slot 1154 is centrally formed in each collet extension 1138 extending through the extension at the bottom surface 1148, the outer cylindrical surface 1152 and partially into the outer cylindrical surface 1143 at the insert body 1136. The illustrated embodiment includes the one slot 1154 centrally located in each extension 1138. It is foreseen that other embodiments of the invention may include more or fewer slots 1154. The slots 1154 substantially equally partition each of the extensions 1138, forming four distinct resilient, fingers, tabs or panels 1154 that extend to the bottom surface 1148.

Figure 66:
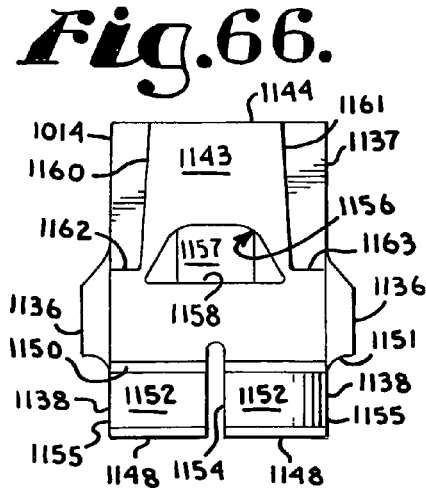
FIG. 66 is a side elevational view of the insert of FIG. 63.
Figure 67:
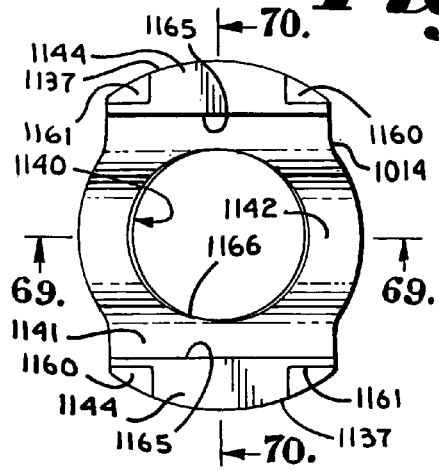
FIG. 67 is a top plan view of the insert of FIG. 63.
Figure 68:
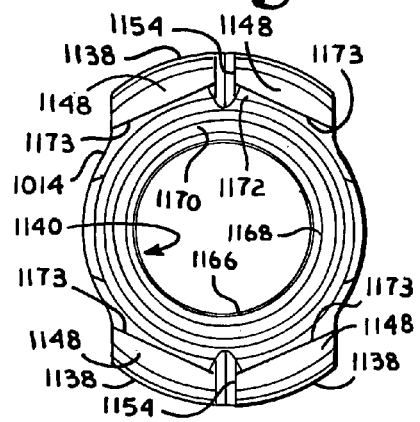
FIG. 68 is a bottom plan view of the insert of FIG. 63.
Figure 69:
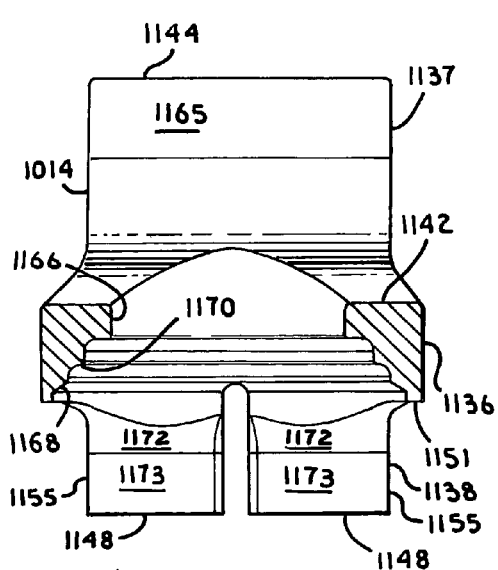
FIG. 69 is an enlarged cross-sectional view taken along the line 69-69 of FIG. 67.
Figure 70:
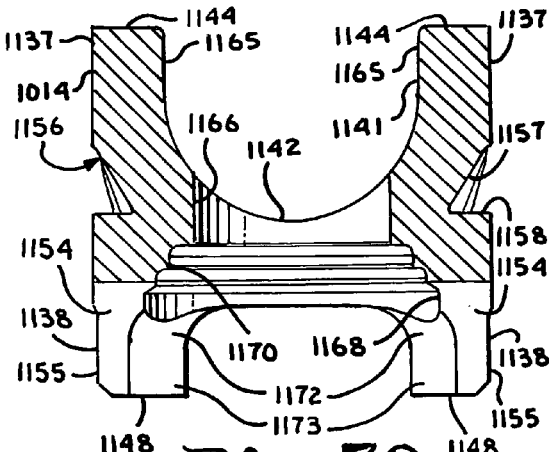
FIG. 70 is an enlarged cross-sectional view taken along the line 70-70 of FIG. 67.

The surfaces 1143 are sized and shaped to generally fit within the receiver arms 1062. The arm outer surfaces 1143 further include notches or grooves formed thereon for receiving manipulation, unlocking and locking tools. Although not shown, each surface 1143 may include one or more through bores or other apertures for receiving tooling, such as that shown on the locking insert 1014' in FIG. 84, for example. Centrally located (in some embodiments below a through bore) and formed in each surface 1143 is a delta or triangular notch or recess, generally 1156, for receiving tooling defined in part by an upper sloping surface 1157 and intersecting a lower planar surface 1158 disposed substantially perpendicular to a central axis of the insert 1014 (and the axis B of the receiver when the insert is disposed within the receiver). Each of the surfaces 1167 and surface 1168 cooperate and align with the respective receiver aperture through bore surfaces 1077 and 1075' when the insert 1014 is captured and operationally positioned within the receiver 1010 as will be described in greater detail below. In the illustrated embodiments, also formed in each surface 1143 are a pair of spaced v- or squared-off notches or grooves 1160 and 1161 that run from the respective top surface 1144 to near the surface 1158 of the central delta cut or notch 1156. The grooves 1160 and 1161 cooperate with the receiver crimp wall inner surfaces 1087 to aid in alignment of the insert channel saddle 1141 with the receiver channel 1064 as shown, for example in FIGS. 74 and 75. The illustrated pair of grooves 1160 and 1161 slope slightly toward one another as best shown in FIG. 66, running from respective bottom surfaces 1162 and 1163 to a closest location at the arm top surface 1144.

The u-shaped channel formed by the saddle 1141 is also partially defined by inner planar surfaces 1165 located near the arm top surfaces 1144. The saddle 1141 also communicates with the bore 1140 at an inner cylindrical surface 1166, the surface 1166 located centrally within the insert body 1136 and further communicating with a lower collet space that extends to the discontinuous bottom surfaces 1148 of the collet extensions 1138. The inner cylindrical surface 1166 also communicates with a lower concave surface portion 1168 having a generally spherical profile with a radius the same or substantially similar to a radius of the surface 1034 of the shank upper portion or head 1008. The surface 1168 primarily terminates at the body lower surface 1151, but also extends into and partially defines inner surfaces of the collet extensions 1138. Located along the inner surface 1168 between the cylindrical surface 1166 and the body lower surface 1151 is a shank gripping surface portion 1170. The gripping surface portion 1170 includes one or more stepped surfaces or ridges sized and shaped to grip and penetrate into the shank head 1008 when the insert 1014 is locked against the head surface 1034. In the illustrated embodiments, substantially all the inner surface 1168 is made up of stepped portions and thus the entire surface may also be described as having a plurality of cylindrical surfaces of graduating diameters. It is foreseen that the stepped surface portion 1170 may include a greater or fewer number of stepped surfaces and cover greater or less surface area of the inner surface 1168 having the same or similar spherical profile as the surface 1034 of the shank head 1008. It is foreseen that any and all of the shank gripping surface portion 1170 and the surface 1168 may additionally or alternatively include a roughened or textured surface or surface finish, or may be scored, knurled, or the like, for enhancing frictional engagement with the shank upper portion 1008. Located below the body lower surface 1151, each collet extension 1138 includes a pair of inner upper curved portion 1172 and a pair of planar surface portion 1173, each planar surface portion 1173 located between an adjacent curved portion 1172 and adjacent respective bottom surface 1148. The planar surface portion 1173 are sized, shaped and positioned with respect to one another to provide a non-locking frictional fit with the spherical surface 1034 of the shank upper portion or head 1008 as will be described in greater detail below. It is foreseen that in some embodiments of the invention, the planar surfaces 1173 may be replaced by radiused surfaces having the same, greater or lesser radius than the shank surface 1034.

The insert bore 1140 is sized and shaped to receive the driving tool (not shown) therethrough that engages the shank drive feature 46 when the shank body 1006 is driven into bone with the receiver 1100 attached. Also, the bore 1140 may receive a manipulation tool used for releasing the alternative locking insert 1014' from a locked position with the receiver, the tool pressing down on the shank and also gripping the insert 1014' at the opposed through bores or with other tool engaging features. A manipulation tool for un-wedging the insert 1104' from the receiver 1100 may also access the such tooling bores from the receiver through bores 1074. The illustrated insert 1014 may further include other features, including grooves and recesses for manipulating and holding the insert 1014 within the receiver 1010 and providing adequate clearance between the retainer 1012 and the insert 1014.

The insert body 1136 located between the arms 1137 and the collet extensions 1138 has an outer diameter slightly smaller than a diameter between crests of the guide and advancement structure 1072 of the receiver 1010, allowing for top loading of the compression insert 1014 into the receiver opening 1066, with the arms 1137 of the insert 1014 being located between the receiver arms 6102 during insertion of the insert 1014 into the receiver 1010. Once the arms 1137 of the insert 1014 are generally located beneath the guide and advancement structure 1072, the insert 1014 is rotated into place about the receiver axis B until the top surfaces 1144 are located directly below the guide and advancement structure 1072 as will be described in greater detail below.

With reference to FIGS. 49 and 82-83, the illustrated elongate rod or longitudinal connecting member 1021 (of which only a portion has been shown) can be any of a variety of implants utilized in reconstructive spinal surgery, but is typically a cylindrical, elongate structure having the outer substantially smooth, cylindrical surface 1022 of uniform diameter. The illustrated rod 1021 is identical or substantially similar to the rod 21 previously described herein. Other longitudinal connecting members for use with the assembly 1001 may take a variety of shapes, including but not limited to rods or bars of oval, rectangular or other curved or polygonal cross-section. The shape of the insert 1014 may be modified so as to closely hold, and if desired, fix or slidingly capture the longitudinal connecting member to the assembly 1001. Some embodiments of the assembly 1001 may also be used with a tensioned cord. Such a cord may be made from a variety of materials, including polyester or other plastic fibers, strands or threads, such as polyethylene-terephthalate. Furthermore, the longitudinal connector may be a component of a longer overall dynamic stabilization connecting member, with cylindrical or bar-shaped portions sized and shaped for being received by the compression insert 1014 of the receiver having a U-shaped, rectangular- or other-shaped channel, for closely receiving the longitudinal connecting member. The longitudinal connecting member may be integral or otherwise fixed to a bendable or damping component that is sized and shaped to be located between adjacent pairs of bone screw assemblies 1001, for example. A damping component or bumper may be attached to the longitudinal connecting member at one or both sides of the bone screw assembly 1001. A rod or bar (or rod or bar component) of a longitudinal connecting member may be made of a variety of materials ranging from non-metallic materials, such as soft deformable plastics, to hard metals, depending upon the desired application. Thus, bars and rods of the invention may be made of materials including, but not limited to metal and metal alloys including but not limited to stainless steel, titanium, titanium alloys and cobalt chrome; or other suitable materials, including plastic polymers such as polyetheretherketone (PEEK), ultra-high-molecular weight-polyethylene (UHMWP), polyurethanes and composites, including composites containing carbon fiber, natural or synthetic elastomers such as polyisoprene (natural rubber), and synthetic polymers, copolymers, and thermoplastic elastomers, for example, polyurethane elastomers such as polycarbonate-urethane elastomers.

With reference to FIGS. 49 and 82-83, the closure structure or closure top 1018 shown with the assembly 1001 is identical or substantially similar to the closure top 18 previously described herein with respect to the assembly 1. It is noted that the closure 1018 top could be a twist-in or slide-in closure structure. The illustrated closure structure 1018 is substantially cylindrical and includes a an outer helically wound guide and advancement structure 1182 in the form of a flange that operably joins with the guide and advancement structure 1072 disposed on the arms 1062 of the receiver 1010. The illustrated closure structure 1018 also includes a top surface 1184 with an internal drive 1186 in the form of an aperture that is illustrated as a star-shaped internal drive such as that sold under the trademark TORX, or may be, for example, a hex drive, or other internal drives such as slotted, tri-wing, spanner, two or more apertures of various shapes, and the like. A driving tool (not shown) sized and shaped for engagement with the internal drive 1166 is used for both rotatable engagement and, if needed, disengagement of the closure 1018 from the receiver arms 1062. It is also foreseen that the closure structure 1018 may alternatively include a break-off head designed to allow such a head to break from a base of the closure at a preselected torque, for example, 70 to 140 inch pounds. Such a closure structure would also include a base having an internal drive to be used for closure removal. A base or bottom surface 1188 of the closure is planar and further includes a rim 1190 and may or may not include a further include a central point (not shown), the rim 1190 and or the point (not shown) for engagement and penetration into the surface 1022 of the rod 1021 in certain embodiments of the invention. The closure top 1018 may further include a cannulation through bore (not shown) extending along a central axis thereof and through the top and bottom surfaces thereof. Such a through bore provides a passage through the closure 1018 interior for a length of wire (not shown) inserted therein to provide a guide for insertion of the closure top into the receiver arms 1062.

An alternative closure top 1218 for use with a deformable rod, such as a PEEK rod 1221, is shown in FIGS. 91 and 92. The top 2118 is identical to the top 1018 with the exception that a point or nub 1289 is located on a domed surface 1290 in lieu of the rim of the closure top 1018. The closure top 1218 otherwise includes a guide and advancement structure 1283, a top 1284, an internal drive 1286 and a bottom outer annular surface 1288 that are the same or substantially similar to the guide and advancement structure 1183, top 1184, internal drive 1186 and a bottom surface 1188 described herein with respect to the closure top 1018. In some embodiments, the internal drive 1286 is not as large as the drive 1186 of the closure top 1018, such smaller drive providing for less force being placed on a deformable rod, for example, and not being required when a locking insert, for example, the insert 1014' discussed below is utilized in a bone screw assembly of the invention.

Returning to the assembly 1110, preferably, the receiver 1010, the retainer 1012 and the compression insert 1014 are assembled at a factory setting that includes tooling for holding, pressing and alignment of the component pieces as well as compressing or expanding the insert 1014 arms and/or collet extensions, if needed, as well as crimping a portion of the receiver 1010 toward the insert 1014. In some circumstances, the shank 1004 is also assembled with the receiver 1010, the retainer 1012 and the compression insert 1014 at the factory. In other instances, it is desirable to first implant the shank 1004, followed by addition of the pre-assembled receiver, retainer and compression insert at the insertion point. In this way, the surgeon may advantageously and more easily implant and manipulate the shanks 1004, distract or compress the vertebrae with the shanks and work around the shank upper portions or heads without the cooperating receivers being in the way. In other instances, it is desirable for the surgical staff to pre-assemble a shank of a desired size and/or variety (e.g., surface treatment of roughening the upper portion 1008 and/or hydroxyapatite on the shank 1006), with the receiver, retainer and compression insert. Allowing the surgeon to choose the appropriately sized or treated shank 1004 advantageously reduces inventory requirements, thus reducing overall cost.

Figure 74:
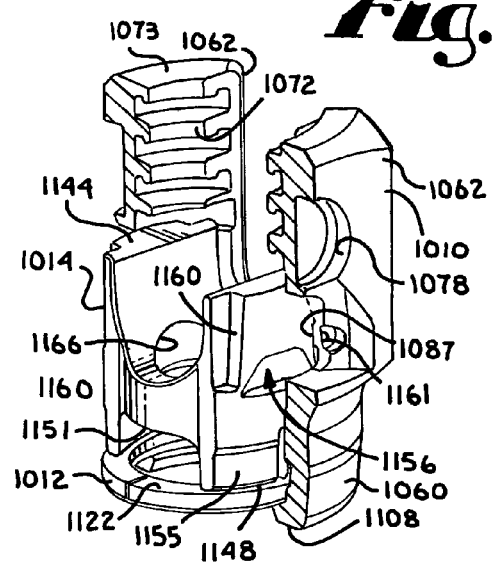
FIG. 74 is an enlarged perspective view with portions broken away of the assembly shown in FIG. 73 and further showing a subsequent step of crimping a portion of the receiver against the insert.
Figure 75:
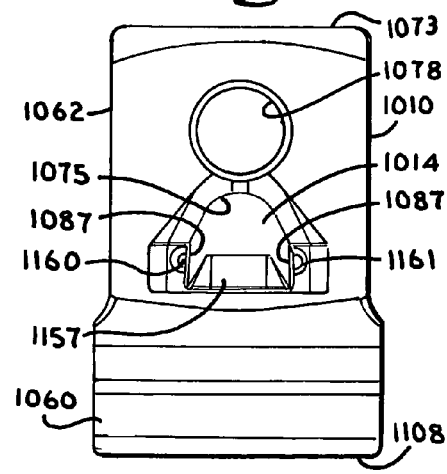
FIG. 75 is an enlarged side elevational view of the assembly shown in FIG. 74.
Figure 77:
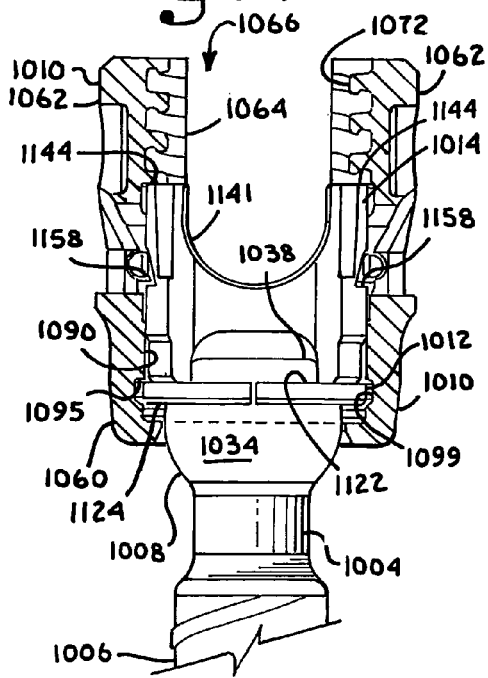
FIG. 77 is an enlarged and partial front elevational view with portions broken away, similar to FIG. 76 showing the shank (not implanted in a vertebra) in a stage of assembly with the retainer, the retainer being pushed up into engagement with the insert.

Pre-assembly of the receiver 1010, retainer 1012 and compression insert 1014 is shown in FIGS. 71-75. First, the retainer 1012 is downloaded in a sideways manner into the receiver 1010 through the upper opening 1066 with the outer surface 1130 facing the receiver channel seat 1068. The retainer 1012 is then lowered between the arms 1062 and toward the receiver base 1060 as shown in phantom in FIG. 71, the retainer being turned or tilted to a position within the receiver base 1060 inner cavity 1061 wherein the retainer bottom surface 1124 is manipulated to a position facing the annular surface 1104 (also shown in phantom) and then fully seated upon the inner base annular surface 1104 as shown in solid lines in FIG. 71. With reference to FIG. 72, the compression insert 1014 is then downloaded into the receiver 1010 through the upper opening 1066 with the crown collet extension bottom surfaces 1148 facing the receiver arm top surfaces 1073 and the insert arms 1137 as well as the insert collet extensions 1138 located between the opposed receiver arms 1062. The insert 1014 is then lowered toward the channel seat 1068 until the insert 1014 arm upper surfaces 1144 are adjacent the run-out area defined by the surfaces 1082 of the receiver below the guide and advancement structure 1072. Thereafter, the insert 1014 is rotated in a clockwise or counter-clockwise manner about the receiver axis B until the upper arm surfaces 1144 are directly below the guide and advancement structure 1072 as illustrated in FIG. 73 with the U-shaped channel 1141 of the insert 1014 aligned with the U-shaped channel 1064 of the receiver 1010. In some embodiments, the insert arms 1137 and collet extensions 1138 may need to be compressed slightly during rotation to clear inner surfaces of the receiver arms 1062. As shown in FIGS. 73-75, the outer cylindrical surfaces 1143 and 1152 of the insert 1014 are received within the cylindrical surfaces 1086 and 1090 of the receiver. With particular reference to FIGS. 74 and 75, the receiver thin walls of the sloping surface 1077 located about the arched through bore portion 1075 are then crimped inwardly toward the axis B by inserting a tool (not shown) into the receiver apertures 1074, the tool pressing the sloped surface walls 1077 until the inner wall surfaces 1087 engage the insert 1014 at the grooves 1160 and 1161 formed into the outer cylindrical surface 1143 of each of the insert arms 1137. The crimping of the opposed wall surfaces 1087 into the groves 1160 and 1161 keeps the insert 1014 U-shaped channel 1141 substantially aligned with the receiver U-shaped channel 1064, but allows for upward movement of the insert 1014 along the receiver axis B during bottom loading of the shank 1004 as shown in FIG. 77, for example. Thus, the crimping of the receiver walls 1077 prohibits rotation of the insert 1104 about the receiver axis B but allows for limited axial movement of the insert 1014 with respect to the receiver 1010 along the axis B when some force is exerted to slide the crimped surface 1087 up or down along the grooves 1160 and 1161. The insert 1014 arms 1137 are fully captured within the receiver 1010 by the guide and advancement structure 1072 prohibiting movement of the insert 1014 up and out through the receiver opening 1066 as well as by the retainer 1012 and the receiver annular surface 1104 located in the receiver 1010 base 1060 below the insert 1014.

In some embodiments of the invention, top or side surfaces of the insert 1014 may include a resilient projection or projections for temporarily frictionally engaging with an inner surface of the receiver 1010 to hold the insert 1014 in an upper portion of the receiver 1010 during some of the assembly steps, also providing a frictional but slidable fit between the insert 1014 and the receiver 1010. In the illustrated embodiment, the insert 1014 is substantially freely slidable in the upper portion of the receiver 1010 in an axial direction, and sized an shaped so that the insert 1014 is located above the cylindrical surface 1099 during expansion of the retainer 1012 about the shank head 1008, the surface 1099 functioning as an expansion chamber or recess for the retainer 1012.

At this time, the receiver, insert and retainer combination are ready for shipping to an end user, with both the compression insert 1014 and the retainer 1012 captured within the receiver 1010 in a manner that substantially prevents movement or loss of such parts out of the receiver 1010. The receiver 1010, compression insert 1014 and the retainer 1012 combination may now be assembled with the shank 1004 either at the factory, by surgery staff prior to implantation, or directly upon an implanted shank 1004 as shown, for example, in FIG. 76, with the shank axis A and the receiver axis B either being aligned during assembly as shown in FIG. 77 and most of the drawings figures illustrating the assembly process, or the axes being at an angle with respect to one another as shown in FIG. 76.

As illustrated in FIG. 76, the bone screw shank 1004 or an entire assembly 1001 made up of the assembled shank 1004, receiver 1010, retainer 1012 and compression insert 1014, is screwed into a bone, such as the vertebra 1017, by rotation of the shank 1004 using a suitable driving tool (not shown) that operably drives and rotates the shank body 1006 by engagement thereof at the internal drive 10046. Specifically, the vertebra 1017 may be pre-drilled to minimize stressing the bone and have a guide wire (not shown) inserted therein to provide a guide for the placement and angle of the shank 1004 with respect to the vertebra. A further tap hole may be made using a tap with the guide wire as a guide. Then, the bone screw shank 1004 or the entire assembly 1001 is threaded onto the guide wire utilizing the cannulation bore 1050 by first threading the wire into the opening at the bottom 1028 and then out of the top opening at the drive feature 1046. The shank 1004 is then driven into the vertebra using the wire as a placement guide. It is foreseen that the shank and other bone screw assembly parts, the rod 1021 (also having a central lumen in some embodiments) and the closure top 1018 (also with a central bore) can be inserted in a percutaneous or minimally invasive surgical manner, utilizing guide wires. When the shank 1004 is driven into the vertebra 1017 without the remainder of the assembly 1001, the shank 1004 may either be driven to a desired final location or may be driven to a location slightly above or proud to provide for ease in assembly with the pre-assembled receiver, compression insert and retainer.

Figure 78:
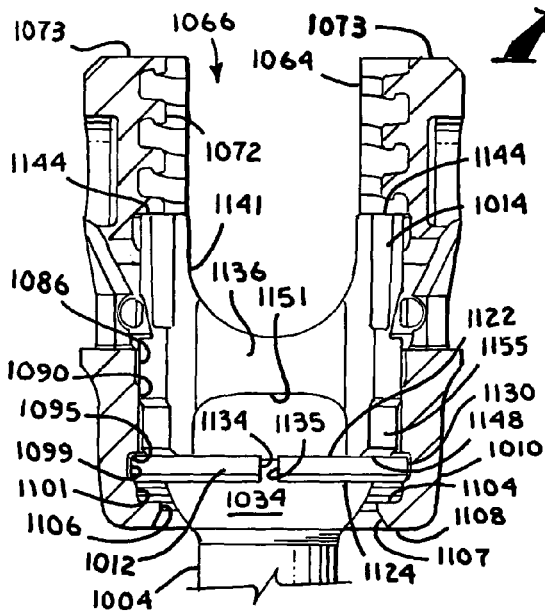
FIG. 78 is an enlarged partial front elevational view with portions broken away, similar to FIG. 77, showing the retainer in an expanded state about an upper portion of the shank, the shank upper portion in a stage of assembly with the insert.
Figure 79:
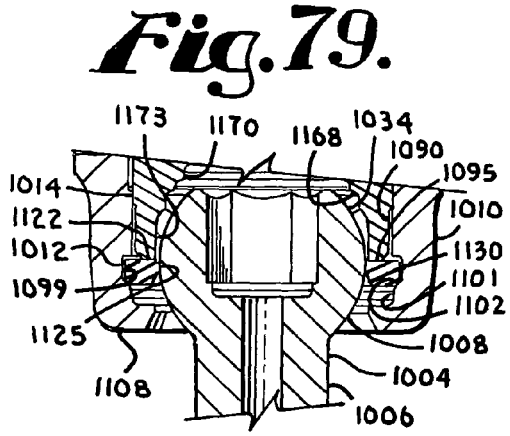
FIG. 79 is a reduced partial front elevational view of the assembly as shown in FIG. 78, with further portions broken away to show the stage of assembly between the shank upper portion, the retainer and the insert.
Figure 80:
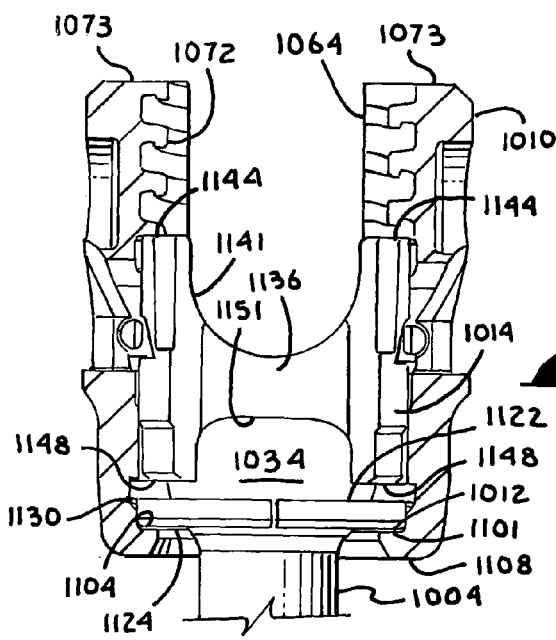
FIG. 80 is a reduced partial front elevational view with portions broken away, similar to FIG. 78, the shank upper portion in frictional engagement with the insert and the retainer in a substantially neutral state.

With reference to FIGS. 76 and 77, the pre-assembled receiver, insert and retainer are placed above the shank upper portion 1008 until the shank upper portion is received within the opening 1110. With particular reference to FIGS. 77 and 78, as the shank upper portion 1008 is moved into the interior 1061 of the receiver base, the shank upper portion 1008 presses the retainer 1012 upwardly into the recess partially defined by the cylindrical surface 1099 and partially by the annular surface 1095. With particular reference to FIGS. 78 and 79, as the portion 1008 continues to move upwardly toward the channel 1064, the top surface 1122 of the retainer 1012 abuts against the receiver annular surface 1095, stopping upward movement of the retainer 1012 and forcing outward movement of the retainer 1012 towards the cylindrical surface 1099 defining the receiver expansion recess as the spherical surface 1034 continues in an upward direction. With reference to FIGS. 80 and 81, the retainer 1012 begins to contract about the spherical surface 1034 as the center of the sphere of the head 1008 passes beyond the center of the retainer expansion recess defined by the surface 1099. At this time also, the spherical surface 1034 moves into engagement with the insert 1014 collet panels 1155 at the panel inner planar surfaces 1173, the panels 1155 initially expanding slightly outwardly to receive the surface 1034. The panels 1155 press outwardly toward the surface 1090 that provides enough clearance for the spherical surface 1034 to enter into full frictional engagement with the panel inner surfaces 1173 as shown in FIG. 81. At this time, the insert 1014 and the surface 1034 are in a fairly tight friction fit, the surface 1034 being pivotable with respect to the insert 1014 with some force. Thus, a tight, non-floppy ball and socket joint is now created between the insert 1014 and the shank upper portion 1008.

The shank 1004 and attached insert 1014 may then be manipulated further downwardly into a desired position for receiving the rod 1021 or other longitudinal connecting member by either an upward pull on the receiver 1010 or, in some cases, by driving the shank 1004 further into the vertebra 1017. Also, in some embodiments, when the receiver 1010 is pre-assembled with the shank 1004, the entire assembly 1001 may be implanted at this time by inserting the driving tool (not shown) into the receiver and the shank drive 1046 and rotating and driving the shank 1004 into a desired location of the vertebra 1017. Also, at this time, the receiver 1010 and may be articulated to a desired angular position with respect to the shank 1004, such as that shown in FIG. 83, but prior to insertion of the rod or closure top, that will be held, but not locked, by the frictional engagement between the retainer 1012 and the shank upper portion 1008.

With reference to FIGS. 82 and 83, the rod 1021 is eventually positioned in an open or percutaneous manner in cooperation with the at least two bone screw assemblies 1001. The closure structure 1018 is then inserted into and advanced between the arms 1062 of each of the receivers 1010. The closure structure 1018 is rotated, using a tool engaged with the inner drive 1186 until a selected pressure is reached at which point the rod 1021 engages the U-shaped seating surface 1142 of the compression insert 1014, pressing the insert stepped shank gripping surfaces 1170 against the shank spherical surface 1034, the edges of the stepped surfaces penetrating into the spherical surface 1034 and also pressing the shank upper portion 1008 into locked frictional engagement with the retainer 1012. Specifically, as the closure structure 1018 rotates and moves downwardly into the respective receiver 1010, the rim 1190 engages and penetrates the rod surface 1022, the closure structure 1018 pressing downwardly against and biasing the rod 1021 into compressive engagement with the insert 1014 that urges the shank upper portion 1008 toward the retainer 1012 and into locking engagement therewith, the retainer 1012 frictionally abutting the surface 1104 and expanding outwardly against the cylindrical surface 1101. For example, about 80 to about 120 inch pounds of torque on the closure top may be applied for fixing the bone screw shank 1006 with respect to the receiver 1010.

With reference to FIGS. 84-89, an alternative lock-and-release compression insert 1014' is illustrated for use with the shank 1004, receiver 1010, retainer 1012, closure top 1018 and rod 1021 previously described herein, the resulting assembly identified as an assembly 1001' in FIGS. 89 and 90, for example. The insert 1014' is identical or substantially similar to the insert 1014 previously described herein, with the exception that the insert 1014' is sized for a locking, frictional interference fit with the receiver 1010; specifically, a locking interference between the cylindrical inner surface 1090 of the receiver 1010 and a lower portion of the outer cylindrical surfaces 1143' of the insert arms 1137' as will be described in greater detail below. The illustrated insert 1014' also differs from the insert 1014 in that the insert 1014' includes a pair of opposed through bores 1159' for receiving tooling as will be described in greater detail below.

Figure 84:
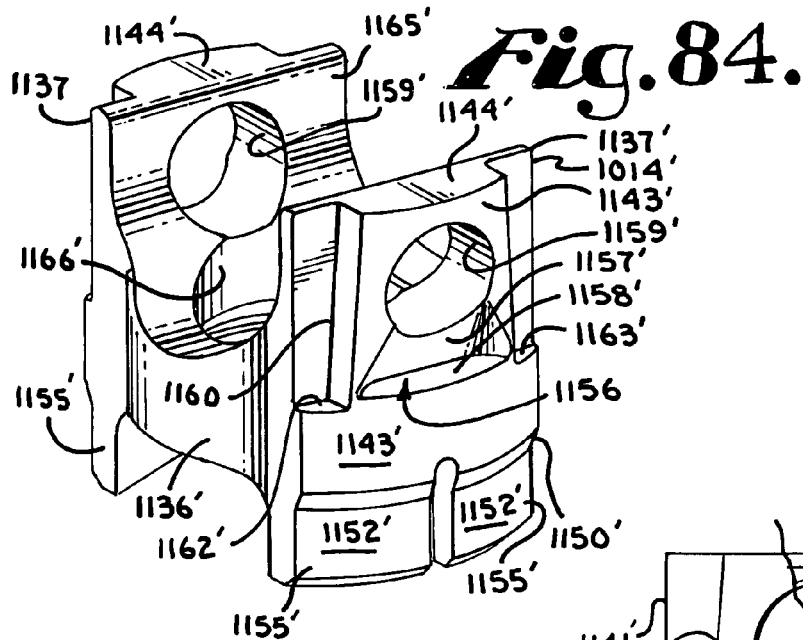
FIG. 84 is an enlarged perspective view of an alternative locking insert according to the invention for use in the assembly of FIG. 49 in lieu of the insert shown in FIG. 49.
Figure 85:
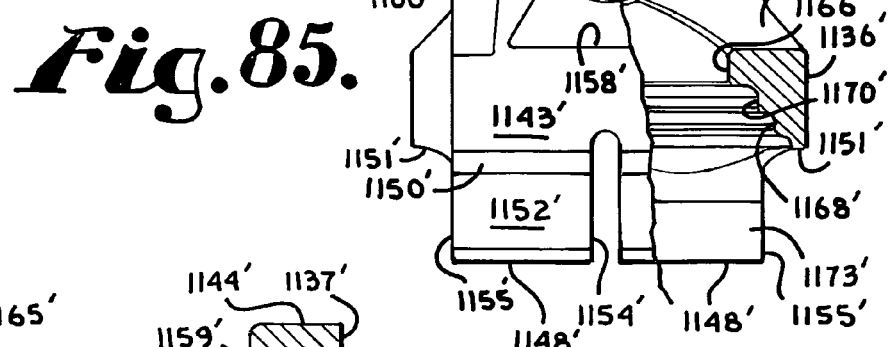
FIG. 85 is an enlarged side elevational view of the insert of FIG. 84 with portions broken away to show the detail thereof.
Figure 86:
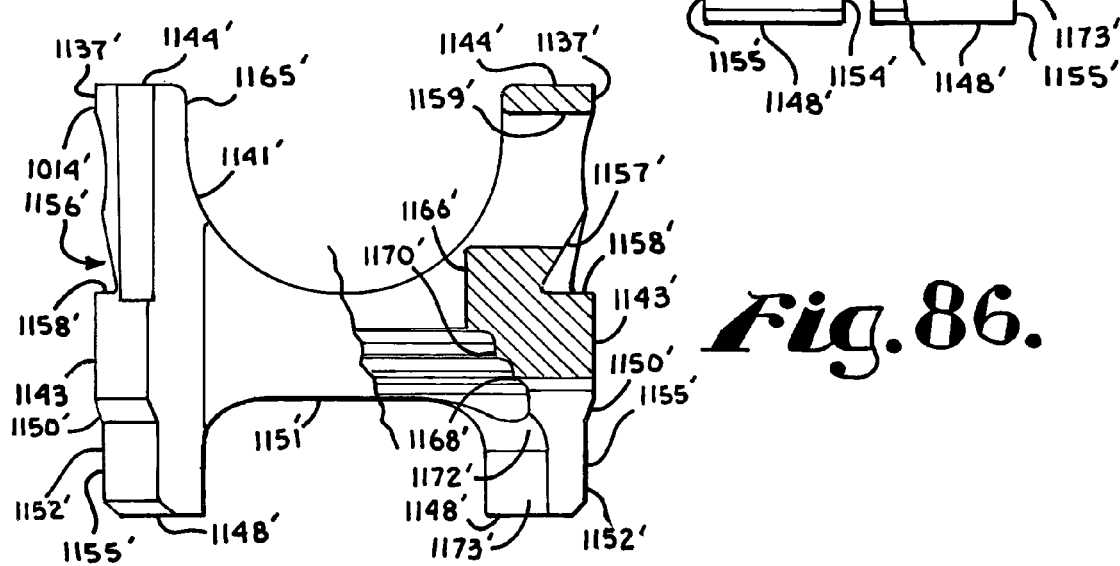
FIG. 86 is an enlarged front elevational view of the insert of FIG. 84 with portions broken away to show the detail thereof.

Thus, with reference to FIGS. 84-86, the locking insert 1014 includes a body 1136', a pair of opposed arms 1137', a pair of crown collet extensions 1138', a through bore 1140', a u-shaped saddle surface 1141' with a seat 1142', arm outer surfaces 1143', arm top surfaces 1144', collet extension bottom surfaces 1148', arms rim or ledge surfaces 1150', annular lower body surfaces 1151', lower outer cylindrical surfaces 1152', slots 1154', panels 1155' formed by the slots, notches 1156' having an upper sloping surface 1157' and a lower planar surface 1158', a pair of grooves 1160' and 1161', having respective bottom surfaces 1162' and 1163', inner planar opposed surfaces 1165', inner cylindrical surfaces 1166', an inner spherical profile 1168' with a gripping surface portion 1170', curved inner surfaces 1172' and collet planar inner gripping friction fit surfaces 1173' that are the same or substantially similar in form and function to the respective body 1136, pair of opposed arms 1137, pair of crown collet extensions 1138, through bore 1140, u-shaped saddle surface 1141 with seat 1142, arm outer surfaces 1143, arm top surfaces 1144, collet extension bottom surfaces 1148, arms rim or ledge surfaces 1150, annular lower body surfaces 1151, lower outer cylindrical surfaces 1152, slots 1154, panels 1155 formed by the slots, notches 1156 having upper sloping surfaces 1157 and a lower planar surface 1158, pair of grooves 1160 and 1161 having respective bottom surfaces 1162 and 1163, inner planar opposed surfaces 1615, inner cylindrical surfaces 1166, inner spherical profile 1168 with a gripping surface portion 1170, curved inner surfaces 1172 and planar friction fit gripping surfaces 1173 previously described herein with respect to the insert 1014.

The insert 1014' outer cylindrical surfaces 1143' that are located below the tooling notches 1156' and at or near the ledge or rim 1150' are sized and shaped for a locking interference fit with the receiver 1010 at the cylindrical surface 1090 that partially defines the inner cavity 1061. In other words, a width or diameter measured between arm surfaces 1143' at or directly above the rim 1150' is sized large enough to require that the insert 1014' must be forced into the space defined by the cylindrical surface 1090 starting at the edge defined by the receiver surface 1088 and the surface 1090 by a tool or tools or by the closure top 1018 forcing the rod 1021 downwardly against the insert 1014' with sufficient force to interferingly lock the insert 1014' into the receiver 1010 at the cylindrical surface 1090.

With reference to FIGS. 87-90, the insert 1014' is assembled with the receiver 1010, retainer 1012, shank 1004, rod 1021 and closure top 1018, in a manner the same as previously described above with respect to the assembly 1001, resulting in an assembly 1001', with the exception that the insert 1014' must be forced downwardly into a locking interference fit with the receiver 1010 when the shank 1004 is locked in place, as compared to the easily sliding relationship between the insert 1014 and the receiver 1010. In particular, prior to assembly with the rod 1021 and the closure top 1018, the compression insert 1014' outer cylindrical surfaces 1152' are slidingly received by receiver cylindrical surface 1090, but the surfaces 1143' are not. The insert 1014' is thus prohibited from moving any further downwardly at the receiver surface 1088 unless forced downwardly by a locking tool or by the closure top pressing downwardly on the rod that in turn presses downwardly on the insert 1014' as shown in FIGS. 89 and 90. With further reference to FIG. 89, at this time, the receiver 1010 may be articulated to a desired angular position with respect to the shank 1004, such as that shown in FIG. 96, for example, that will be held, but not locked, by the frictional engagement between the retainer 1012 collet panels and the shank upper portion 1008.

The rod 1021 is eventually positioned in an open or percutaneous manner in cooperation with the at least two bone screw assemblies 1001'. The closure structure 1018 is then inserted into and advanced between the arms 1062 of each of the receivers 1010. The closure structure 1018 is rotated, using a tool engaged with the inner drive 1186 until a selected pressure is reached at which point the rod 1021 engages the U-shaped seating surface 1142' of the compression insert 1014', pressing the insert stepped shank gripping surfaces 1170' against and into the shank spherical surface 1034, the edges of the stepped surfaces 1170' penetrating into the spherical surface 1034, pressing the shank upper portion 1008 into locked frictional engagement with the retainer 1012. Specifically, as the closure structure 18 rotates and moves downwardly into the respective receiver 1010, the rim 1190 engages and penetrates the rod surface 1022, the closure structure 1018 pressing downwardly against and biasing the rod 1021 into compressive engagement with the insert 1014' that urges the shank upper portion 1008 toward the retainer 1012 and into locking engagement therewith, the retainer 1012 frictionally abutting the surface 1104 and expanding outwardly against the cylindrical surface 1101. For example, about 80 to about 120 inch pounds of torque on the closure top may be applied for fixing the bone screw shank 1006 with respect to the receiver 1010. Tightening the helical flange form to approximately 100 inch pounds can create around 900 to 1000 pounds of force and it has been found that the interference fit created between the cylindrical surfaces 1143' of the insert 1014' and the cylindrical surface 1090 of the receiver can be overcome at between about 500 to 700 inch pounds depending on manufacturing tolerance issues between the parts. So, as the closure structure 1018 and the rod 1021 press the insert 1014' downwardly toward the base of the receiver 1010, the insert surfaces 1143' are forced into the receiver at the edge defined by the receiver annular surface 1088 and the cylindrical surface 1090, thus forcing and fixing the insert 1014 into frictional interference engagement with the receiver at and along the surface 1090, while not substantially affecting the locking of the polyaxial mechanism itself.

With reference to FIG. 91, at this time, the closure top 1018 may be loosened or removed and/or the rod 1021 may be adjusted and/or removed and the frictional engagement between the insert 1014' and the receiver 1010 at the insert surfaces 1143' will remain locked in place, advantageously maintaining a locked angular position of the shank 1004 with respect to the receiver 1010.

With further reference to FIGS. 91 and 92, at this time, another rod, such as the deformable rod 1221 and cooperating alternative closure top 1218 may be loaded onto the already locked-up assembly to result in an alternative assembly 1201'. As mentioned above, the closure drive 1286 may advantageously be made smaller than the drive of the closure 1018, such that the deformable rod 1221 is not unduly pressed or deformed during assembly since the polyaxial mechanism is already locked.

With reference to FIGS. 93-95, a two-piece tool, generally 1600, is illustrated for releasing the insert 1014' from the receiver 1010. The tool 1600 includes an inner flexible tube-like structure with opposed inwardly facing prongs 1612 located on either side of a through-channel 1616. The channel 1616 may terminate at a location spaced from the prongs 1612 or may extend further upwardly through the tool, resulting in a two-piece tool 1610. The tool 1600 includes an outer, more rigid tubular member 1620 having a smaller through channel 1622. The member 1620 slidingly fits over the tube 1610 after the flexible member 1610 prongs 1612 are flexed outwardly and then fitted over the receiver 1010 and then within through bores of the opposed apertures 1074 of the receiver 1010 and aligned opposed bores 1159' located on arms of the insert 1014'. In FIG. 93, the tool 1600 is shown during the process of unlocking the insert 1014' from the receiver 1010 with the outer member 1620 surrounding the inner member 1610 and holding the prongs 1612 within the receiver 1010 and insert 1014' apertures while the tool 1600 is pulled upwardly away from the shank 1004. It is foreseen that the tool 1600 may further include structure for pressing down upon the receiver 1010 while the prongs and tubular member are pulled upwardly, such structure may be located within the tool 1600 and press down upon the top surfaces 1073 of the receiver arms, for example.

Alternatively, another manipulation tool (not shown) may be used that is inserted into the receiver at the opening 1066 and into the insert channel formed by the saddle 1141', with prongs or extensions thereof extending outwardly into the insert through bores 1159'; a piston-like portion of the tool thereafter pushing directly on the shank upper portion 1008, thereby pulling the insert 1014' away from the receiver surface 1090 and thus releasing the polyaxial mechanism. At such time, the shank 1004 may be articulated with respect to the receiver 1010, and the desired friction fit returns between the retainer 1012 and the shank surface 1034, so that an adjustable, but non-floppy relationship still exists between the shank 1004 and the receiver 1010. If further disassembly if the assembly is desired, such is accomplished in reverse order to the procedure described previously herein for the assembly 1001.

With reference to FIGS. 96-98, another manipulation tool, generally 1700, is illustrated for independently locking the insert 1014', or, in some embodiments, temporarily locking the non-locking insert 1014, to the receiver 1010. The tool 1700 includes a pair of opposed arms 1712, each having an engagement extension 1716 positioned at an angle with respect to the respective arm 1712 such that when the tool is moved downwardly toward the receiver, one or more inner surfaces 1718 of the engagement extension 1716 slide along the surfaces 1077 of the receiver and along 1157' of the insert 1014' to engage the insert 1014', with a surface 1720 pressing downwardly on the insert surfaces 1158', pushing the cylindrical arm surfaces 1143' into an interference locking fit within the receiver cylindrical surface 1090. As shown in FIG. 98, when the insert 1014' is locked against the receiver 1010, the tool bottom surfaces 1720 do not bottom out on the receiver surfaces 7105', but remained spaced therefrom. In the illustrated embodiment, the surface 1718 is slightly rounded and each arm extension 1716 further includes a planar lower surface 1722 that creates an edge with the bottom surface 1720 for insertion and gripping of the insert 1014' at the juncture of the surface 1157' and the surface 1158'. The tool 1700 may include a variety of holding and pushing/pulling mechanisms, such as a pistol grip tool, that may include a ratchet feature, a hinged tool, or, a rotatably threaded device, for example.

It is to be understood that while certain forms of the present invention have been illustrated and described herein, it is not to be limited to the specific forms or arrangement of parts described and shown.

What is claimed and desired to be secured by Letters Patent is as follows:

1. A bone anchor assembly for securing a longitudinal connecting member to a bone, the bone anchor assembly comprising:
    a receiver having a through bore around a central vertical axis, the receiver including a lower body with a bottom opening and an internal cavity communicating with an upper portion having a pair of opposed arms defining a first channel therebetween opening onto a top thereof, the first channel having opposed inner surfaces and a transverse axis perpendicular to the central vertical axis, the first channel sized and shaped for receiving a portion of the longitudinal connecting member, the arms having a discontinuous helically wound guide and advancement structure thereon, and the receiver including interior opposed recesses having downwardly-facing top surfaces located entirely below the helically wound guide and advancement structure;
    a bone attachment structure having a body and an upper head portion having a substantially spherical surface above a hemisphere thereof, the body extending through the receiver bottom opening and pivotal with respect to the receiver; and
    an insert having a body with upright arms forming a second channel therebetween, the second channel being alienable with the receiver transverse axis to receive the portion of the longitudinal connecting member, the upright arms having uppermost top surfaces, the insert body further including a central through-and-through tool receiving opening and oppositely-directed opposed radial extending portions with outer surfaces in the direction of the receiver transverse axis engageable with the receiver first channel inner surfaces to inhibit rotation between the receiver and the insert, the opposed radial extending portions having top surfaces that extend radially outward and underneath a most bottom surface of the portion of the longitudinal connecting member positioned within the receiver first channel,
    wherein when the uppermost top surfaces of the upright arms of the insert are snapped under and engaging the downwardly-facing top surfaces of the receiver opposed recesses, the bone attachment structure has a non-floppy relationship with respect to the receiver, and the insert is prevented from moving back up within the receiver prior to the longitudinal connecting member being positioned within the receiver and the insert first and second channels and locked by a closure structure.

2. The bone anchor assembly of claim 1, wherein the insert upright arms further include upper portions projecting radially outward near the uppermost top surfaces thereof, with the top surfaces of the radially-projecting upper portions defining the uppermost top surfaces of the insert.

3. The bone anchor assembly of claim 1, wherein the bone attachment structure upper head portion is held in the receiver cavity by a separate retainer.

4. The bone anchor assembly of claim 1, wherein the insert body is above the bone attachment structure upper head portion so as to cooperate in providing a friction fit between the bone attachment structure and the receiver.

5. The bone anchor assembly of claim 1, wherein the bone attachment structure is positioned within the receiver prior to the insert uppermost top surfaces being snapped under the downwardly-facing top surfaces of the receiver opposed recesses.

6. The bone anchor assembly of claim 3, wherein the retainer is non-pivoting with respect to the receiver.

7. The bone anchor assembly of claim 1, wherein the insert further includes a lower extending portion in the direction of the bone attachment structure upper head portion so as to provide a friction fit with respect to the bone attachment structure and the receiver.

8. The bone anchor assembly of claim 1, wherein the closure structure has a corresponding continuous helically wound structure engageable with the discontinuous helically wound guide and advancement structure.

9. The bone anchor assembly of claim 8, wherein the closure structure is configured to abut the longitudinal connecting member positioned in the receiver first channel.

10. The bone anchor assembly of claim 8, wherein the closure structure corresponding continuous helically wound structure is threadably engagable with the discontinuous helically wound guide and advancement structure, thereby advancing the closure structure into the receiver first channel upon rotation of the closure structure relative to the receiver.

11. The bone anchor assembly of claim 8, wherein the closure structure remains spaced apart from the insert when the bone anchor assembly is in a locked configuration.

12. The bone anchor assembly of claim 1, wherein the receiver discontinuous helically wound guide and advancement structure inhibits the receiver arms from splaying open at the top thereof.

13. The bone anchor assembly of claim 1, wherein a width of the insert second channel at the level of the uppermost top surfaces of the insert upright arms, as measured perpendicular to both the transverse axis and the central vertical axis, is greater than a diameter of the longitudinal connecting member.

14. The bone anchor assembly of claim 1, wherein a length of the insert second channel between outer ends of the opposed radial extending portions, as measured along the transverse axis, is greater than the greatest width between inner surfaces of the insert upright arms forming the second channel therebetween, as measured perpendicular to both the transverse axis and the central vertical axis.

15. The bone anchor assembly of claim 1, wherein the insert uppermost top surfaces do not extend above a top of the longitudinal connecting member positioned within the receiver first channel and the insert second channel when the bone anchor assembly is in a locked configuration.

16. The bone anchor assembly of claim 1,
wherein the insert body and upright arms together form a saddle surface that defines a lower limit of the insert second channel, and
wherein top surfaces of the opposed radial extending portions extend the saddle surface in the direction of the transverse axis so as to be underneath the portion of the longitudinal connecting member positioned within the insert second channel.

17. The bone anchor assembly of claim 1, wherein the insert has a non-snap-fit engagement with the portion of the longitudinal connecting member positioned within the insert second channel.

18. The bone anchor assembly of claim 1, wherein bottom surfaces of the insert opposed radial extending portions overlie a receiver channel surface defined by an upper edge of the receiver body extending between the receiver arms.

19. The bone anchor assembly of claim 1, wherein the insert upright arms are snapped into the receiver opposed recesses after the bone attachment structure upper head portion is disposed within the receiver internal cavity.

20. The bone anchor assembly of claim 1, wherein the insert upright arms further include upper portions that flair radially outward and vertically upward, with the top surfaces of the upper portions defining the uppermost top surfaces of the insert.

21. The bone anchor assembly of claim 1, wherein the insert opposed radial extending portions top surfaces are opposite a lower most bottom facing surface of the portion of the longitudinal connecting member positioned within the receiver first channel.

22. The bone anchor assembly of claim 1, wherein the insert upright arms have exterior surfaces with a maximum width therebetween and the radial extending portions have a maximum length, as measured along the transverse axis, that is great than the maximum width.

23. A bone anchor assembly for securing a longitudinal connecting member to a bone, the bone anchor assembly comprising:
a receiver having a through bore around a central vertical axis, the receiver including a lower body with a bottom opening and an internal cavity communicating with an upper portion having a pair of opposed arms defining a first channel therebetween opening onto a top thereof, the first channel having a transverse axis perpendicular to the central vertical axis, the first channel sized and shaped for receiving a portion of the longitudinal connecting member, the arms having a discontinuous helically wound guide and advancement structure thereon, and the receiver including interior opposed recesses having downwardly-facing top surfaces located entirely below the helically wound guide and advancement structure;
a bone attachment structure having a body and an upper head portion with a substantially spherical surface above a hemisphere thereof, the body extending through the receiver bottom opening and pivotal with respect to the receiver; and
an insert having a body with upright arms forming a second channel therebetween, the second channel being alignable with the transverse axis to receive the portion of the longitudinal connecting member therein, the upright arms having uppermost top surfaces, the insert body further including a central through-and-through tool receiving opening and oppositely-directed opposed radial extensions in the direction of the transverse axis to extend a second channel supporting surface for the longitudinal connecting member in the direction of the transverse axis, the opposed radial extensions having top surfaces that extend radially outward and underneath a most bottom surface of the portion of the longitudinal connecting member, the extensions inhibiting rotation of the insert with respect to the receiver,
wherein after the bone attachment structure upper head portion is positioned within the internal cavity, the uppermost top surfaces of the upright arms are snapped under the downwardly-facing top surfaces of the receiver opposed recesses to prevent upward movement of the insert when the insert is fully disposed within the receiver first channel, so as to prevent the insert from moving back up within the receiver prior to the assembly being put into a locked orientation with a closure.

24. The bone anchor assembly of claim 23,
wherein the insert body and upright arms together form a saddle surface that defines a lower limit of the insert second channel, and
wherein the top surfaces of the opposed radial extensions extend the saddle surface in the direction of the transverse axis so as to be underneath the portion of the longitudinal connecting member positioned within the insert second channel.

25. The bone anchor assembly of claim 24, wherein the opposed radial extensions have lateral surfaces to engage an inner sidewall surface of the receiver arms so as to block rotation between the insert and the receiver.

26. The bone anchor assembly of claim 23, wherein a length of the insert second channel between outer ends of the opposed radial extensions, as measured along the transverse axis, is greater than the greatest width between inner surfaces of the insert upright arms forming the second channel therebetween, as measured perpendicular to both the transverse axis and the central vertical axis.

27. The bone anchor assembly of claim 23, wherein the insert upright arms further include upper portions that flair radially outward and vertically upward, with the top surfaces of the upper portions defining the uppermost top surfaces of the insert.

28. The bone anchor assembly of claim 23, wherein the closure has a corresponding continuous helically wound structure engageable with the discontinuous helically wound guide and advancement structure.

29. The bone anchor assembly of claim 23, further comprising a resilient retainer located in the cavity, the retainer being expandable in the cavity about the bone attachment structure upper head portion and receiving the upper head portion therethrough to capture the upper head portion in the cavity, the bone attachment structure being pivotable with respect to the retainer prior to locking of the bone attachment structure with respect to the receiver.

30. A bone anchor assembly for securing an elongate rod to a bone, the bone anchor assembly comprising:
a receiver having a vertical axis, a lower body defining an internal cavity communicating with a bottom surface of the receiver through a bottom opening, and a first pair of upright arms extending upwardly from the lower body to define a first channel opening onto a top thereof for receiving the elongate rod, the first channel having a transverse axis perpendicular to the vertical axis and communicating with the internal cavity to define a through bore centered around the vertical axis, the upright arms having interior surfaces with a discontinuous guide and advancement structure formed therein, the receiver having opposed recesses with downwardly-facing top surfaces located entirely below the discontinuous guide and advancement structure;

a bone attachment structure having a body and an upper head portion with a substantially spherical surface above a hemisphere thereof, the body extending through the receiver bottom opening and pivotal with respect to the receiver; and an insert having a body with a second pair of upright arms centered around a vertically-extending midsection of the body and forming a second channel therebetween, the second channel being alignable with the receiver transverse axis to receive the elongate rod, the insert upright arms having uppermost portions protruding laterally at the vertically-extending midsection of the insert body and terminating at uppermost top surfaces, the insert body further including a central through-and-through tool receiving opening and oppositely-directed opposed radial extensions in the direction of the receiver transverse axis to inhibit rotation between the receiver and the insert, wherein top surfaces of the insert opposed radial extensions extend radially outward so as to be underneath a most bottom surface of the elongate rod, and wherein the uppermost top surfaces of the upright arms are snapped under and engaging the downwardly-facing top surfaces of the receiver opposed recesses to prevent upward movement of the insert when the insert is fully disposed within the receiver first channel, so as to prevent the insert from moving back up within the receiver prior to the insert being further pushed down within the receiver into a locked orientation by a closure.

31. The bone anchor assembly of claim 30, wherein the insert upright arm uppermost portions protruding laterally extend radially outward near the uppermost top surfaces thereof, with the top surfaces of the radially-outward protruding uppermost portions defining the uppermost top surfaces of the insert.

32. The bone anchor assembly of claim 30, wherein the bone attachment structure upper head portion is engaged in the receiver by a separate cylindrical shaped member having a central opening.

33. The bone anchor assembly of claim 30, wherein when the insert body upright arm uppermost top surfaces are snapped under and engaged with the downwardly-facing top surfaces of the receiver opposed recesses and the upper head portion of the bone attachment structure is positioned under the insert body, the insert cooperates to provide a friction fit between the bone attachment structure and the receiver.

34. The bone anchor assembly of claim 30, further comprising a resilient retainer located in the cavity, the retainer being expandable in the cavity about the bone attachment structure upper head portion and receiving the upper head portion therethrough to capture the upper head portion in the cavity, the bone attachment structure being pivotable with respect to the retainer prior to the bone attachment structure coming into the locked orientation with respect to the receiver by the closure.

35. The bone anchor assembly of claim 34, wherein the insert remains spaced from the retainer and the retainer is non-pivoting with respect to the receiver.

36. The bone anchor assembly of claim 30, wherein the insert further includes a lower extending portion in the direction of the bone attachment structure upper head portion so as to cooperate in providing a friction fit for the bone attachment structure with respect to the receiver prior to the assembly coming into the locked orientation by the closure.

37. The bone anchor assembly of claim 30, wherein the closure has a corresponding continuous helically wound structure engageable with the receiver discontinuous guide and advancement structure.

38. The bone anchor assembly of claim 37, wherein the closure is configured to abut the elongate rod received in the receiver first channel.

39. The bone anchor assembly of claim 37, wherein the corresponding continuous helically wound structure is threadably engageable with the receiver discontinuous guide and advancement structure, thereby advancing the closure into the receiver first channel upon rotation of the closure relative to the receiver.

40. The bone anchor assembly of claim 37, wherein the closure remains spaced apart from the insert when the bone anchor assembly is in the locked orientation.

41. The bone anchor assembly of claim 30, wherein the receiver discontinuous guide and advancement structure further comprises a splay resisting construction.

42. The bone anchor assembly of claim 30, wherein a width between inner surfaces of the insert second channel at the level of the uppermost top surfaces of the insert upright arms, as measured perpendicular to both the transverse axis and the vertical axis, is greater than a diameter of the elongate rod.

43. The bone anchor assembly of claim 30, wherein a length of the insert second channel between outer ends of the opposed radial extensions, as measured along the transverse axis, is greater than the greatest width between inner surfaces of the insert upright arms at their uppermost portions, as measured perpendicular to both the transverse axis and the vertical axis.

44. The bone anchor assembly of claim 30, wherein the insert uppermost top surfaces do not extend above a top of the elongate rod positioned within the receiver first channel and the insert second channel when the bone anchor assembly is in the locked orientation.

45. The bone anchor assembly of claim 30,
wherein the insert body and upright arms together form a saddle surface that defines a lower limit of the insert second channel, and
wherein the top surfaces of the opposed radial extensions extend the saddle surface in the direction of the transverse axis so as to be underneath the most bottom surface of the portion of the elongate rod positioned within the insert second channel.

46. The bone anchor assembly of claim 45, wherein the top surfaces of the opposed radial extensions extend the saddle surface beyond an inner sidewall surface of the receiver arms.

47. The bone anchor assembly of claim 30, wherein bottom surfaces of the opposed radial extensions overlie a receiver channel surface defined by an upper edge of the receiver body extending between the receiver arms.

48. The bone anchor assembly of claim 30, wherein the insert upright arms are snapped into the receiver opposed recesses after the bone attachment structure upper head portion is disposed within the receiver internal cavity.

49. The bone anchor assembly of claim 30, wherein the insert upright arm uppermost portions flair radially outward and vertically upward, with the top surfaces of the uppermost portions defining the uppermost top surfaces of the insert.

50. The bone anchor assembly of claim 30, wherein the insert opposed radial extensions have a top surface that is opposite a lower most bottom facing surface of the elongate rod positioned within the receiver channel.

51. The bone anchor assembly of claim 30, wherein the insert upright arms centered around the vertically-extending midsection of the insert body have exterior surfaces with a maximum width therebetween and the radial extensions have a maximum length, as measured along the transverse axis, that is great than the maximum width.

52. The bone anchor assembly of claim 30, wherein the insert engages the bone attachment structure upper head portion.

53. The bone anchor assembly of claim 30, wherein the insert has a non-snap-on engagement to receive the portion of the longitudinal connecting member therein.

54. The bone anchor assembly of claim 30, wherein the bone attachment structure has a friction fit relationship with respect to the receiver.

55. The bone anchor assembly of claim 30, wherein when the bone attachment structure upper head portion is positioned within the receiver internal cavity and the insert is positioned within the receiver and spaced above the upper head portion, the bone attachment structure has a non-floppy pivotal relationship with respect to the receiver.

* * * * *

UNITED STATES PATENT AND TRADEMARK OFFICE
CERTIFICATE OF CORRECTION

PATENT NO. : 9,980,753 B2
APPLICATION NO. : 13/374439
DATED : May 29, 2018
INVENTOR(S) : Roger P. Jackson Page 1 of 1

It is certified that error appears in the above-identified patent and that said Letters Patent is hereby corrected as shown below:

On the Title Page
- In the Title (54) and in the Specification, Column 1, Line 1, following "PIVOTAL" insert --BONE--.

In the Claims
- In Claim 1, in Column 43, Line 48, delete "alienable" and insert --alignable-- therefor.

Signed and Sealed this
Ninth Day of October, 2018

Andrei Iancu
*Director of the United States Patent and Trademark Office*